US009907459B2

(12) United States Patent
Blanquart

(10) Patent No.: US 9,907,459 B2
(45) Date of Patent: *Mar. 6, 2018

(54) IMAGE SENSOR WITH TOLERANCE OPTIMIZING INTERCONNECTS

(71) Applicant: Depuy Synthes Products, Inc., Raynham, MA (US)

(72) Inventor: Laurent Blanquart, Westlake Village, CA (US)

(73) Assignee: DePuy Synthes Products, Inc., Raynham, MA (US)

(*) Notice: Subject to any disclaimer, the term of this patent is extended or adjusted under 35 U.S.C. 154(b) by 174 days.

This patent is subject to a terminal disclaimer.

(21) Appl. No.: 14/875,591

(22) Filed: Oct. 5, 2015

(65) Prior Publication Data

US 2016/0155765 A1 Jun. 2, 2016

Related U.S. Application Data

(63) Continuation of application No. 13/471,274, filed on May 14, 2012, now Pat. No. 9,153,609.

(Continued)

(51) Int. Cl.
*H01L 27/00* (2006.01)
*A61B 1/05* (2006.01)
(Continued)

(52) U.S. Cl.
CPC .......... *A61B 1/051* (2013.01); *A61B 1/00009* (2013.01); *A61B 1/0676* (2013.01);
(Continued)

(58) Field of Classification Search
CPC ......... H01L 27/14634; H01L 27/14636; H01L 25/0657
See application file for complete search history.

(56) References Cited

U.S. PATENT DOCUMENTS 3,796,220 A 3/1974 Bredemeier
3,858,577 A 1/1975 Bass et al.
(Continued)

FOREIGN PATENT DOCUMENTS

AU 2012253261 6/2016
CN 1953193 A 4/2007
(Continued)

OTHER PUBLICATIONS

H.Kurino et al., Intelligent image sensor chip with three dimensional structure, Technical Digest, International Electron Devices Meeting 1999, Dec. 5, 1999, pp. 879-882.

*Primary Examiner* — Thanh Luu

(74) *Attorney, Agent, or Firm* — Terrence J. Edwards; TechLaw Ventures, PLLC

(57) ABSTRACT

Embodiments of a hybrid imaging sensor that optimizes a pixel array area on a substrate using a stacking scheme for placement of related circuitry with minimal vertical interconnects between stacked substrates and associated features are disclosed. Embodiments of maximized pixel array size/die size (area optimization) are disclosed, and an optimized imaging sensor providing improved image quality, improved functionality, and improved form factors for specific applications common to the industry of digital imaging are also disclosed. Embodiments of the above may include systems, methods and processes for staggering ADC or column circuit bumps in a column or sub-column hybrid image sensor using vertical interconnects are also disclosed.

20 Claims, 39 Drawing Sheets

Related U.S. Application Data

(60) Provisional application No. 61/485,432, filed on May 12, 2011, provisional application No. 61/485,435, filed on May 12, 2011, provisional application No. 61/485,440, filed on May 12, 2011, provisional application No. 61/485,426, filed on May 12, 2011.

(51) Int. Cl.

| | | |
|---|---|---|
| *H01L 27/146* | (2006.01) | |
| *A61B 1/00* | (2006.01) | |
| *H04N 5/374* | (2011.01) | |
| *H04N 5/3745* | (2011.01) | |
| *H04N 5/378* | (2011.01) | |
| *H01L 23/00* | (2006.01) | |
| *A61B 1/06* | (2006.01) | |
| *H04N 5/225* | (2006.01) | |
| *H01L 31/028* | (2006.01) | |
| *H01L 31/0296* | (2006.01) | |
| *H01L 31/0304* | (2006.01) | |

(52) U.S. Cl.
CPC ............ *H01L 24/17* (2013.01); *H01L 27/146* (2013.01); *H01L 27/1464* (2013.01); *H01L 27/1469* (2013.01); *H01L 27/14601* (2013.01); *H01L 27/14603* (2013.01); *H01L 27/14618* (2013.01); *H01L 27/14634* (2013.01); *H01L 27/14636* (2013.01); *H01L 27/14638* (2013.01); *H01L 27/14641* (2013.01); *H01L 27/14643* (2013.01); *H01L 27/14689* (2013.01); *H04N 5/2256* (2013.01); *H04N 5/378* (2013.01); *H04N 5/3742* (2013.01); *H04N 5/37455* (2013.01); *H04N 5/37457* (2013.01); *H01L 31/028* (2013.01); *H01L 31/0296* (2013.01); *H01L 31/0304* (2013.01); *H01L 2924/0002* (2013.01); *H01L 2924/381* (2013.01); *H04N 2005/2255* (2013.01)

(56) References Cited

U.S. PATENT DOCUMENTS

| | | |
|---|---|---|
| 4,011,403 A | 3/1977 | Epstein et al. |
| 4,153,356 A | 5/1979 | Hama |
| 4,350,150 A | 9/1982 | Kubota et al. |
| 4,363,963 A | 12/1982 | Ando |
| 4,429,686 A | 2/1984 | Hosoda |
| 4,433,675 A | 2/1984 | Konoshima |
| 4,436,095 A | 3/1984 | Kruger |
| 4,561,430 A | 12/1985 | Walsh |
| 4,572,164 A | 2/1986 | Yoshida et al. |
| 4,589,404 A | 5/1986 | Barath et al. |
| 4,600,940 A | 7/1986 | Sluyter |
| 4,604,992 A | 8/1986 | Sato |
| 4,670,653 A | 6/1987 | McConkle et al. |
| 4,740,837 A | 4/1988 | Yanagisawa et al. |
| 4,741,327 A | 5/1988 | Yabe |
| 4,745,471 A | 5/1988 | Takamura et al. |
| 4,773,396 A | 9/1988 | Okazaki |
| 4,786,965 A | 11/1988 | Yabe |
| 4,800,424 A | 1/1989 | Noguchi |
| 4,831,444 A | 5/1989 | Kato |
| 4,832,003 A | 5/1989 | Yabe |
| 4,845,555 A | 7/1989 | Yabe et al. |
| 4,853,772 A | 8/1989 | Kikuchi |
| 4,866,526 A | 9/1989 | Ams et al. |
| 4,888,639 A | 12/1989 | Yabe et al. |
| 4,918,521 A | 4/1990 | Yabe et al. |
| 4,938,205 A | 7/1990 | Nudelman |
| 4,942,473 A | 7/1990 | Zeevi et al. |
| 4,953,539 A | 9/1990 | Nakamura et al. |
| 4,954,878 A | 9/1990 | Fox et al. |
| 5,010,038 A | 4/1991 | Fox et al. |
| 5,010,876 A | 4/1991 | Henley et al. |
| 5,016,975 A | 5/1991 | Sasaki et al. |
| 5,021,888 A | 6/1991 | Kondou et al. |
| 5,042,915 A | 8/1991 | Akutsu et al. |
| 5,065,444 A | 11/1991 | Garber |
| RE33,854 E | 3/1992 | Adair |
| 5,103,497 A | 4/1992 | Hicks |
| 5,111,804 A | 5/1992 | Funakoshi |
| 5,115,309 A | 5/1992 | Hang |
| 5,133,035 A | 7/1992 | Hicks |
| 5,168,361 A | 12/1992 | Hackmann |
| 5,168,863 A | 12/1992 | Kurtzer |
| 5,187,572 A | 2/1993 | Nakamura et al. |
| 5,188,094 A | 2/1993 | Adair |
| 5,200,838 A | 4/1993 | Nudelman et al. |
| 5,220,198 A | 6/1993 | Tsuji |
| 5,227,662 A | 7/1993 | Ohno et al. |
| 5,228,430 A | 7/1993 | Sakamoto |
| 5,237,403 A | 8/1993 | Sugimoto et al. |
| 5,241,170 A | 8/1993 | Field, Jr. et al. |
| 5,277,172 A | 1/1994 | Sugimoto |
| 5,289,555 A | 2/1994 | Sanso |
| 5,307,804 A | 5/1994 | Bonnet |
| 5,313,306 A | 5/1994 | Kuban et al. |
| 5,325,847 A | 7/1994 | Matsuno |
| 5,339,275 A | 8/1994 | Hyatt |
| 5,381,784 A | 1/1995 | Adair |
| 5,400,267 A | 3/1995 | Denen et al. |
| 5,402,768 A | 4/1995 | Adair |
| 5,411,020 A | 5/1995 | Ito |
| 5,427,087 A | 6/1995 | Ito et al. |
| 5,454,366 A | 10/1995 | Ito et al. |
| 5,461,425 A | 10/1995 | Fowler et al. |
| 5,471,515 A | 11/1995 | Fossum et al. |
| 5,489,801 A | 2/1996 | Blish, II |
| 5,494,483 A | 2/1996 | Adair |
| 5,522,006 A | 5/1996 | Takeuchi et al. |
| 5,550,595 A | 8/1996 | Hannah |
| 5,576,781 A | 11/1996 | Deleeuw |
| 5,594,282 A | 1/1997 | Otsuki |
| 5,594,497 A | 1/1997 | Ahern et al. |
| 5,614,763 A | 3/1997 | Womack |
| 5,665,959 A | 9/1997 | Fossum et al. |
| 5,734,418 A | 3/1998 | Danna |
| 5,748,234 A | 5/1998 | Lippincott |
| 5,754,313 A | 5/1998 | Pelchy et al. |
| 5,757,075 A | 5/1998 | Kitaoka |
| 5,784,099 A | 7/1998 | Lippincott |
| 5,787,298 A | 7/1998 | Broedner et al. |
| 5,841,126 A | 11/1998 | Fossum et al. |
| 5,857,963 A | 1/1999 | Pelchy et al. |
| 5,879,289 A | 3/1999 | Yarush et al. |
| 5,887,049 A | 3/1999 | Fossum |
| 5,896,166 A | 4/1999 | D'Alfonso et al. |
| 5,907,178 A | 5/1999 | Baker et al. |
| 5,929,901 A | 7/1999 | Adair et al. |
| 5,949,483 A | 9/1999 | Fossum et al. |
| 5,986,693 A | 11/1999 | Adair et al. |
| 5,990,506 A | 11/1999 | Fossum et al. |
| 6,005,619 A | 12/1999 | Fossum |
| 6,021,172 A | 2/2000 | Fossum et al. |
| 6,027,955 A | 2/2000 | Lee et al. |
| 6,028,330 A | 2/2000 | Lee et al. |
| 6,043,839 A | 3/2000 | Adair et al. |
| 6,059,776 A | 5/2000 | Gatto |
| 6,059,793 A | 5/2000 | Pagedas |
| 6,073,043 A | 6/2000 | Schneider |
| 6,096,573 A | 8/2000 | Chen |
| 6,101,232 A | 8/2000 | Fossum et al. |
| 6,118,142 A | 9/2000 | Chen et al. |
| 6,139,489 A | 10/2000 | Wampler et al. |
| 6,142,930 A | 11/2000 | Ito et al. |
| 6,166,367 A | 12/2000 | Cho |
| 6,166,768 A | 12/2000 | Fossum et al. |
| 6,180,969 B1 | 1/2001 | Yang et al. |
| 6,184,055 B1 | 2/2001 | Yang et al. |
| 6,194,260 B1 | 2/2001 | Chien et al. |
| 6,198,087 B1 | 3/2001 | Boon |
| 6,207,984 B1 | 3/2001 | Chang |

(56) References Cited

U.S. PATENT DOCUMENTS

| | | |
|---|---|---|
| 6,211,904 B1 | 4/2001 | Adair et al. |
| 6,215,517 B1 | 4/2001 | Takahashi et al. |
| 6,239,456 B1 | 5/2001 | Berezin et al. |
| 6,242,277 B1 | 6/2001 | Lin et al. |
| 6,255,681 B1 | 7/2001 | Osadchy et al. |
| 6,272,269 B1 | 8/2001 | Naum |
| 6,275,255 B1 | 8/2001 | Adair et al. |
| 6,294,775 B1 | 9/2001 | Seibel et al. |
| 6,303,421 B1 | 10/2001 | Chang |
| 6,310,642 B1 | 10/2001 | Adair et al. |
| 6,313,868 B1 | 11/2001 | D'Alfonso et al. |
| 6,320,630 B1 | 11/2001 | Yamashita et al. |
| 6,327,493 B1 | 12/2001 | Ozawa et al. |
| 6,331,156 B1 | 12/2001 | Haefele et al. |
| 6,333,205 B1 | 12/2001 | Rhodes |
| 6,369,812 B1 | 4/2002 | Iyriboz et al. |
| 6,387,043 B1 | 5/2002 | Yoon |
| 6,388,243 B1 | 5/2002 | Berezin et al. |
| 6,390,972 B1 | 5/2002 | Speier et al. |
| 6,400,824 B1 | 6/2002 | Mansoorian et al. |
| 6,404,048 B2 | 6/2002 | Akram |
| 6,410,377 B1 | 6/2002 | Hwang et al. |
| 6,416,463 B1 | 7/2002 | Tsuzuki et al. |
| 6,419,626 B1 | 7/2002 | Yoon |
| 6,419,627 B1 | 7/2002 | Ben Nun |
| 6,424,369 B1 | 7/2002 | Adair et al. |
| 6,436,032 B1 | 8/2002 | Eto et al. |
| 6,441,482 B1 | 8/2002 | Foster |
| 6,452,626 B1 | 9/2002 | Adair et al. |
| 6,456,326 B2 | 9/2002 | Fossum et al. |
| 6,469,739 B1 | 10/2002 | Bechtel et al. |
| 6,485,414 B1 | 11/2002 | Neuberger |
| 6,512,280 B2 | 1/2003 | Chen et al. |
| 6,515,321 B1 | 2/2003 | Jwo |
| 6,549,235 B1 | 4/2003 | Fossum et al. |
| 6,555,842 B1 | 4/2003 | Fossum et al. |
| 6,570,617 B2 | 5/2003 | Fossum et al. |
| 6,588,884 B1 | 7/2003 | Furlani et al. |
| 6,606,122 B1 | 8/2003 | Shaw et al. |
| 6,610,557 B2 | 8/2003 | Lee et al. |
| 6,627,474 B2 | 9/2003 | Barna et al. |
| 6,659,940 B2 | 12/2003 | Adler |
| 6,665,013 B1 | 12/2003 | Fossum et al. |
| 6,690,466 B2 | 2/2004 | Miller et al. |
| 6,692,431 B2 | 2/2004 | Kazakevich |
| 6,704,049 B1 | 3/2004 | Fossum |
| 6,720,810 B1 | 4/2004 | New |
| 6,726,620 B2 | 4/2004 | Shibata et al. |
| 6,730,900 B2 | 5/2004 | Hsish et al. |
| 6,740,870 B1 | 5/2004 | Doudoumopoulos |
| 6,744,068 B2 | 6/2004 | Fossum et al. |
| 6,773,392 B2 | 8/2004 | Kikuchi et al. |
| 6,784,940 B1 | 8/2004 | Takazawa et al. |
| 6,796,939 B1 | 9/2004 | Hirata et al. |
| 6,799,065 B1 | 9/2004 | Niemeyer |
| 6,809,358 B2 | 10/2004 | Hsieh et al. |
| 6,812,949 B1 | 11/2004 | Switzer et al. |
| 6,838,653 B2 | 1/2005 | Campbell et al. |
| 6,838,716 B2 | 1/2005 | Asada et al. |
| 6,856,712 B2 | 2/2005 | Fauver et al. |
| 6,862,036 B2 | 3/2005 | Adair et al. |
| 6,879,340 B1 | 4/2005 | Chevallier |
| 6,897,082 B2 | 5/2005 | Rhodes et al. |
| 6,899,675 B2 | 5/2005 | Cline et al. |
| 6,921,920 B2 | 7/2005 | Kazakevich |
| 6,943,838 B2 | 9/2005 | Komoro et al. |
| 6,947,090 B2 | 9/2005 | Komoro et al. |
| 6,961,461 B2 | 11/2005 | MacKinnon et al. |
| 6,970,195 B1 | 11/2005 | Bidermann et al. |
| 6,976,954 B2 | 12/2005 | Takahashi |
| 6,982,740 B2 | 1/2006 | Adair et al. |
| 6,982,742 B2 | 1/2006 | Adair et al. |
| 6,997,871 B2 | 2/2006 | Sonnenschein et al. |
| 6,999,118 B2 | 2/2006 | Suzuki |
| 7,002,231 B2 | 2/2006 | Rhodes et al. |
| 7,002,621 B2 | 2/2006 | Adair et al. |
| 7,009,634 B2 | 3/2006 | Iddan et al. |
| 7,009,646 B1 | 3/2006 | Fossum et al. |
| 7,018,331 B2 | 3/2006 | Chang et al. |
| 7,027,092 B2 | 4/2006 | Altree |
| 7,030,904 B2 | 4/2006 | Adair et al. |
| 7,037,259 B2 | 5/2006 | Hakamata et al. |
| 7,061,117 B2 | 6/2006 | Yang et al. |
| 7,068,878 B2 | 6/2006 | Crossman-Bosworth et al. |
| 7,070,560 B2 | 7/2006 | Takashi et al. |
| 7,088,398 B1 | 8/2006 | Wolf et al. |
| 7,102,682 B2 | 9/2006 | Baer |
| 7,105,371 B2 | 9/2006 | Fossum et al. |
| 7,106,367 B2 | 9/2006 | Sarwari |
| 7,106,377 B2 | 9/2006 | Bean et al. |
| 7,115,091 B2 | 10/2006 | Root et al. |
| 7,129,108 B2 | 10/2006 | Jang |
| 7,183,129 B2 | 2/2007 | Lee |
| 7,184,084 B2 | 2/2007 | Glenn |
| 7,189,226 B2 | 3/2007 | Auld et al. |
| 7,193,519 B2 | 3/2007 | Root et al. |
| 7,202,899 B2 | 4/2007 | Lin et al. |
| 7,217,967 B2 | 5/2007 | Han |
| 7,227,469 B2 | 6/2007 | Varner et al. |
| 7,230,247 B2 | 6/2007 | Shibayama |
| 7,230,615 B2 | 6/2007 | Wang et al. |
| 7,232,712 B2 | 6/2007 | Han |
| 7,244,920 B2 | 7/2007 | Kim et al. |
| 7,250,594 B2 | 7/2007 | Lin et al. |
| 7,258,546 B2 | 8/2007 | Beier et al. |
| 7,258,663 B2 | 8/2007 | Doguchi et al. |
| 7,261,687 B2 | 8/2007 | Yang |
| 7,273,452 B2 | 9/2007 | Barbato et al. |
| 7,274,390 B2 | 9/2007 | Sevat et al. |
| 7,276,785 B2 | 10/2007 | Bauer et al. |
| 7,280,139 B2 | 10/2007 | Pahr et al. |
| 7,282,025 B2 | 10/2007 | Abe |
| 7,283,566 B2 | 10/2007 | Siemens et al. |
| 7,295,578 B1 | 11/2007 | Lyle et al. |
| 7,303,528 B2 | 12/2007 | Couvillon, Jr. |
| 7,317,955 B2 | 1/2008 | McGreevy |
| 7,319,478 B2 | 1/2008 | Dolt et al. |
| 7,331,523 B2 | 2/2008 | Meier et al. |
| 7,338,832 B2 | 3/2008 | Park et al. |
| 7,339,982 B2 | 3/2008 | Wood, Jr. |
| 7,354,841 B2 | 4/2008 | Jeon |
| 7,365,768 B1 | 4/2008 | Ono et al. |
| 7,368,771 B2 | 5/2008 | Roh et al. |
| 7,369,166 B2 | 5/2008 | Fossum et al. |
| 7,369,176 B2 | 5/2008 | Sonnenschein et al. |
| 7,386,084 B2 | 6/2008 | Yin |
| 7,391,013 B2 | 6/2008 | Johnston et al. |
| 7,397,076 B2 | 7/2008 | Jang |
| 7,402,811 B2 | 7/2008 | Hatanaka et al. |
| 7,443,296 B2 | 10/2008 | Mezhinsky et al. |
| 7,470,893 B2 | 12/2008 | Suzuki et al. |
| 7,488,637 B2 | 2/2009 | Kim |
| 7,511,257 B2 | 3/2009 | Lee et al. |
| 7,517,351 B2 | 4/2009 | Culp et al. |
| 7,522,341 B2 | 4/2009 | Mouli |
| 7,525,168 B2 | 4/2009 | Hsieh |
| 7,534,645 B2 | 5/2009 | Choi |
| 7,535,037 B2 | 5/2009 | Lyu |
| 7,540,645 B2 | 6/2009 | Kazakevich |
| 7,542,069 B2 | 6/2009 | Tashiro |
| 7,544,163 B2 | 6/2009 | MacKinnon et al. |
| 7,545,434 B2 | 6/2009 | Bean et al. |
| 7,551,059 B2 | 6/2009 | Farrier |
| 7,564,935 B2 | 7/2009 | Suzuki |
| 7,567,291 B2 | 7/2009 | Bechtel et al. |
| 7,568,619 B2 | 8/2009 | Todd et al. |
| 7,573,516 B2 | 8/2009 | Krymski et al. |
| 7,578,786 B2 | 8/2009 | Boulais et al. |
| 7,583,872 B2 | 9/2009 | Seibel et al. |
| 7,589,349 B2 | 9/2009 | Hong |
| 7,595,210 B2 | 9/2009 | Shim |
| 7,598,686 B2 | 10/2009 | Lys et al. |
| 7,599,439 B2 | 10/2009 | Lavelle et al. |
| 7,605,016 B2 | 10/2009 | Min |

(56) References Cited

U.S. PATENT DOCUMENTS

| | | |
|---|---|---|
| 7,608,874 B2 | 10/2009 | Lee et al. |
| 7,612,318 B2 | 11/2009 | Jeon |
| 7,615,808 B2 | 11/2009 | Pain et al. |
| 7,615,838 B2 | 11/2009 | Kim |
| 7,616,986 B2 | 11/2009 | Seibel et al. |
| 7,630,008 B2 | 12/2009 | Sarwari |
| 7,646,407 B2 | 1/2010 | Fossum et al. |
| 7,663,115 B2 | 2/2010 | Korthout et al. |
| 7,744,528 B2 | 6/2010 | Wallace et al. |
| 7,749,799 B2 | 7/2010 | Pain |
| 7,768,562 B2 | 8/2010 | Boemler |
| 7,794,394 B2 | 9/2010 | Frangioni |
| 7,795,650 B2 | 9/2010 | Eminoglu et al. |
| 7,800,192 B2 | 9/2010 | Venezia et al. |
| 7,801,584 B2 | 9/2010 | Iddan et al. |
| 7,830,434 B2 | 11/2010 | Li et al. |
| 7,868,283 B2 | 1/2011 | Mabuchi |
| 7,871,373 B2 | 1/2011 | Yamada |
| 7,880,662 B2 | 2/2011 | Bogaerts |
| 7,901,974 B2 | 3/2011 | Venezia et al. |
| 7,914,447 B2 | 3/2011 | Kanai |
| 7,916,193 B2 | 3/2011 | Fossum |
| 7,923,763 B2 | 4/2011 | Lauxtermann |
| 7,935,050 B2 | 5/2011 | Luanava et al. |
| 7,936,394 B2 | 5/2011 | Wu |
| 7,944,566 B2 | 5/2011 | Xie |
| 7,952,096 B2 | 5/2011 | Rhodes |
| 7,973,342 B2 | 7/2011 | Jeon |
| 7,995,123 B2 | 8/2011 | Lee et al. |
| 8,089,542 B2 | 1/2012 | Chevallier |
| 8,100,826 B2 | 1/2012 | MacKinnon et al. |
| 8,101,903 B2 | 1/2012 | Mokhnatyuk |
| 8,154,055 B2 | 4/2012 | Ha |
| 8,159,584 B2 | 4/2012 | Iwabuchi et al. |
| 8,193,541 B2 | 6/2012 | Maehara |
| 8,212,884 B2 | 7/2012 | Seibel et al. |
| 8,300,111 B2 | 10/2012 | Iwane |
| 8,317,689 B1 | 11/2012 | Remijan et al. |
| 8,382,662 B2 | 2/2013 | Soper et al. |
| 8,384,814 B2 | 2/2013 | Chevallier |
| 8,396,535 B2 | 3/2013 | Wang et al. |
| 8,405,748 B2 | 3/2013 | Mao et al. |
| 8,423,110 B2 | 4/2013 | Barbato et al. |
| 8,471,938 B2 | 6/2013 | Altice, Jr. et al. |
| 8,476,575 B2 | 7/2013 | Mokhnatyuk |
| 8,493,474 B2 | 7/2013 | Richardson |
| 8,493,564 B2 | 7/2013 | Brukilacchio et al. |
| 8,523,367 B2 | 9/2013 | Ogura |
| 8,537,203 B2 | 9/2013 | Seibel et al. |
| 8,582,011 B2 | 11/2013 | Dosluoglu |
| 8,602,971 B2 | 12/2013 | Farr |
| 8,614,754 B2 | 12/2013 | Fossum |
| 8,625,016 B2 | 1/2014 | Fossum et al. |
| 8,629,023 B2 | 1/2014 | Lee |
| 8,638,847 B2 | 1/2014 | Wang |
| 8,648,287 B1 | 2/2014 | Fossum |
| 8,649,848 B2 | 2/2014 | Crane et al. |
| 8,668,339 B2 | 3/2014 | Kabuki et al. |
| 8,675,125 B2 | 3/2014 | Cossairt et al. |
| 8,698,887 B2 | 4/2014 | Makino et al. |
| 8,733,660 B2 | 5/2014 | Wang et al. |
| 8,754,358 B2 | 6/2014 | Chou et al. |
| 8,797,434 B2 | 8/2014 | Lee et al. |
| 8,830,340 B2 | 9/2014 | Burt et al. |
| 8,836,834 B2 | 9/2014 | Hashimoto et al. |
| 8,858,425 B2 | 10/2014 | Farr et al. |
| 8,885,034 B2 | 11/2014 | Adair et al. |
| 8,896,730 B2 | 11/2014 | Fossum |
| 8,952,312 B2 * | 2/2015 | Blanquart ......... H01L 27/14601 |
| | | 250/208.1 |
| 9,066,677 B2 | 6/2015 | Seto |
| 9,123,602 B2 * | 9/2015 | Blanquart ......... H01L 27/14601 |
| 9,153,609 B2 * | 10/2015 | Blanquart ......... H01L 27/14601 |
| 9,343,489 B2 | 5/2016 | Blanquart et al. |
| 2001/0030744 A1 | 10/2001 | Chang |
| 2001/0041825 A1 | 11/2001 | Shibata et al. |
| 2001/0052930 A1 | 12/2001 | Adair et al. |
| 2002/0011809 A1 | 1/2002 | Hartge et al. |
| 2002/0017611 A1 | 2/2002 | Tashiro et al. |
| 2002/0044207 A1 | 4/2002 | Dielhof et al. |
| 2002/0067408 A1 | 6/2002 | Adair et al. |
| 2002/0080248 A1 | 6/2002 | Adair et al. |
| 2002/0158986 A1 | 10/2002 | Baer |
| 2002/0163578 A1 | 11/2002 | Adair et al. |
| 2002/0180867 A1 | 12/2002 | Adair et al. |
| 2003/0007087 A1 | 1/2003 | Hakamata et al. |
| 2003/0043264 A1 | 3/2003 | Furuya et al. |
| 2003/0052983 A1 | 3/2003 | Altree |
| 2003/0107664 A1 | 6/2003 | Suzuki |
| 2003/0163029 A1 | 8/2003 | Sonnenschein et al. |
| 2003/0187586 A1 | 10/2003 | Katzenmaier et al. |
| 2003/0189663 A1 | 10/2003 | Dolt et al. |
| 2003/0218120 A1 | 11/2003 | Shibayama |
| 2004/0010196 A1 | 1/2004 | Wang et al. |
| 2004/0036010 A1 | 2/2004 | Hsieh et al. |
| 2004/0049215 A1 | 3/2004 | Snow et al. |
| 2004/0078494 A1 | 4/2004 | Lennox et al. |
| 2004/0082833 A1 | 4/2004 | Adler et al. |
| 2004/0095495 A1 | 5/2004 | Inokuma et al. |
| 2004/0111012 A1 | 6/2004 | Whitman |
| 2004/0169771 A1 | 9/2004 | Washington et al. |
| 2004/0249267 A1 | 12/2004 | Gilboa |
| 2005/0027164 A1 | 2/2005 | Barbato et al. |
| 2005/0038322 A1 | 2/2005 | Banik |
| 2005/0075538 A1 | 4/2005 | Banik et al. |
| 2005/0131279 A1 | 6/2005 | Boulais et al. |
| 2005/0148819 A1 | 7/2005 | Noguchi et al. |
| 2005/0168941 A1 | 8/2005 | Sokol et al. |
| 2005/0174428 A1 | 8/2005 | Abe |
| 2005/0206755 A1 | 9/2005 | Yokoyarna et al. |
| 2005/0222499 A1 | 10/2005 | Banik et al. |
| 2005/0231591 A1 | 10/2005 | Abe |
| 2005/0234302 A1 | 10/2005 | MacKinnon et al. |
| 2005/0288546 A1 | 12/2005 | Sonnenschein et al. |
| 2006/0007507 A1 | 1/2006 | Inaba et al. |
| 2006/0022234 A1 | 2/2006 | Adair et al. |
| 2006/0023109 A1 | 2/2006 | Mabuchi et al. |
| 2006/0035415 A1 | 2/2006 | Wood et al. |
| 2006/0069314 A1 | 3/2006 | Farr |
| 2006/0164533 A1 | 7/2006 | Hsieh et al. |
| 2006/0181627 A1 | 8/2006 | Farrier |
| 2006/0221230 A1 | 10/2006 | Dutta et al. |
| 2006/0249765 A1 | 11/2006 | Hsieh |
| 2006/0250513 A1 | 11/2006 | Yamamoto et al. |
| 2006/0293563 A1 | 12/2006 | Banik et al. |
| 2006/0293565 A1 | 12/2006 | Uchimura et al. |
| 2007/0002134 A1 | 1/2007 | Ishihara et al. |
| 2007/0030345 A1 | 2/2007 | Amling et al. |
| 2007/0046803 A1 | 3/2007 | Ahn |
| 2007/0078328 A1 | 4/2007 | Ozaki et al. |
| 2007/0091190 A1 | 4/2007 | Iwabuchi et al. |
| 2007/0094303 A1 | 4/2007 | Zwingenberger et al. |
| 2007/0129601 A1 | 6/2007 | Johnston et al. |
| 2007/0138375 A1 | 6/2007 | Lee et al. |
| 2007/0153337 A1 | 7/2007 | Kim |
| 2007/0159526 A1 | 7/2007 | Abe |
| 2007/0182842 A1 | 8/2007 | Sonnenschein et al. |
| 2007/0185549 A1 | 8/2007 | Zdeblick |
| 2007/0187703 A1 | 8/2007 | Erchak |
| 2007/0197873 A1 | 8/2007 | Birnkrant |
| 2007/0225556 A1 | 9/2007 | Ortiz et al. |
| 2007/0244364 A1 | 10/2007 | Luanava et al. |
| 2007/0244365 A1 | 10/2007 | Wiklof |
| 2007/0276187 A1 | 11/2007 | Wiklof et al. |
| 2007/0297190 A1 | 12/2007 | Ng |
| 2008/0021271 A1 | 1/2008 | Pasero et al. |
| 2008/0042046 A1 | 2/2008 | Mabuchi |
| 2008/0045800 A2 | 2/2008 | Farr |
| 2008/0076967 A1 | 3/2008 | Couvillon, Jr. |
| 2008/0122031 A1 | 5/2008 | DeNatale et al. |
| 2008/0128740 A1 | 6/2008 | Yamashita et al. |
| 2008/0136319 A1 | 6/2008 | Yoon |
| 2008/0136945 A1 | 6/2008 | Blanquart et al. |
| 2008/0165360 A1 | 7/2008 | Johnston |

(56) References Cited

U.S. PATENT DOCUMENTS

| | | |
|---|---|---|
| 2008/0185314 A1 | 8/2008 | Tomasello et al. |
| 2008/0200758 A1 | 8/2008 | Orbay et al. |
| 2008/0208006 A1 | 8/2008 | Farr |
| 2008/0211634 A1 | 9/2008 | Hopkins et al. |
| 2008/0218609 A1 | 9/2008 | Blanquart et al. |
| 2008/0218615 A1 | 9/2008 | Huang et al. |
| 2008/0239070 A1 | 10/2008 | Westwick et al. |
| 2008/0239124 A1 | 10/2008 | Mori et al. |
| 2008/0249369 A1 | 10/2008 | Seibel et al. |
| 2008/0255416 A1 | 10/2008 | Gilboa |
| 2008/0258042 A1 | 10/2008 | Krymski |
| 2008/0287798 A1 | 11/2008 | Lee et al. |
| 2008/0309810 A1 | 12/2008 | Smith et al. |
| 2008/0316319 A1 | 12/2008 | Nomoto |
| 2009/0012361 A1 | 1/2009 | MacKinnon et al. |
| 2009/0012368 A1 | 1/2009 | Banik |
| 2009/0015301 A1 | 1/2009 | Marchesini et al. |
| 2009/0021628 A1 | 1/2009 | Yamakoshi |
| 2009/0040783 A1 | 2/2009 | Krupa et al. |
| 2009/0054908 A1 | 2/2009 | Zand et al. |
| 2009/0062656 A1 | 3/2009 | Hyuga |
| 2009/0074265 A1 | 3/2009 | Huang et al. |
| 2009/0076329 A1 | 3/2009 | Su et al. |
| 2009/0082630 A1 | 3/2009 | Tulley |
| 2009/0091641 A1 | 4/2009 | Hattori |
| 2009/0108176 A1 | 4/2009 | Blanquart |
| 2009/0141156 A1 | 6/2009 | Rossi et al. |
| 2009/0141180 A1 | 6/2009 | Kondo et al. |
| 2009/0154886 A1 | 6/2009 | Lewis et al. |
| 2009/0160976 A1 | 6/2009 | Chen et al. |
| 2009/0160979 A1 | 6/2009 | Xu et al. |
| 2009/0173974 A1 | 7/2009 | Shah et al. |
| 2009/0184349 A1 | 7/2009 | Dungan |
| 2009/0186780 A1 | 7/2009 | Lee et al. |
| 2009/0192390 A1 | 7/2009 | Berguer et al. |
| 2009/0200624 A1 | 8/2009 | Dai et al. |
| 2009/0203966 A1 | 8/2009 | Mizuyoshi |
| 2009/0208143 A1 | 8/2009 | Yoon et al. |
| 2009/0212397 A1 | 8/2009 | Tuttle |
| 2009/0216080 A1 | 8/2009 | Nakamura |
| 2009/0225548 A1 | 9/2009 | Narita |
| 2009/0230287 A1 | 9/2009 | Anderson et al. |
| 2009/0236500 A1 | 9/2009 | Shah et al. |
| 2009/0256905 A1 | 10/2009 | Tashiro |
| 2009/0265490 A1 | 10/2009 | Setya et al. |
| 2009/0268147 A1 | 10/2009 | Tang et al. |
| 2009/0278963 A1 | 11/2009 | Shah et al. |
| 2009/0292168 A1 | 11/2009 | Farr |
| 2009/0306478 A1 | 12/2009 | Mizuyoshi |
| 2009/0316116 A1 | 12/2009 | Melville et al. |
| 2009/0322911 A1 | 12/2009 | Blanquart |
| 2009/0322912 A1 | 12/2009 | Blanquart |
| 2010/0026824 A1 | 2/2010 | Chen |
| 2010/0039156 A1 | 2/2010 | Yamaguchi |
| 2010/0059802 A1 | 3/2010 | Chen |
| 2010/0118932 A1 | 5/2010 | Luo et al. |
| 2010/0121142 A1 | 5/2010 | OuYang et al. |
| 2010/0134662 A1 | 6/2010 | Bub |
| 2010/0137684 A1 | 6/2010 | Shibasaki et al. |
| 2010/0157037 A1 | 6/2010 | Iketani et al. |
| 2010/0157039 A1 | 6/2010 | Sugai |
| 2010/0178722 A1 | 7/2010 | de Graff et al. |
| 2010/0182446 A1 | 7/2010 | Matsubayashi |
| 2010/0198009 A1 | 8/2010 | Farr et al. |
| 2010/0204546 A1 | 8/2010 | Hassidov et al. |
| 2010/0228089 A1 | 9/2010 | Hoffman et al. |
| 2010/0276572 A1 | 11/2010 | Iwabuchi et al. |
| 2010/0290100 A1 | 11/2010 | Karasawa |
| 2010/0295978 A1 | 11/2010 | Nakamura et al. |
| 2010/0305406 A1 | 12/2010 | Braun et al. |
| 2011/0028790 A1 | 2/2011 | Farr et al. |
| 2011/0034769 A1 | 2/2011 | Adair et al. |
| 2011/0034770 A1 | 2/2011 | Endo et al. |
| 2011/0037876 A1 | 2/2011 | Talbert et al. |
| 2011/0049591 A1 | 3/2011 | Nakatani et al. |
| 2011/0050874 A1 | 3/2011 | Reshef et al. |
| 2011/0055447 A1 | 3/2011 | Costa |
| 2011/0063428 A1 | 3/2011 | Sonnenschein et al. |
| 2011/0115663 A1 | 5/2011 | Bogaerts |
| 2011/0181840 A1 | 7/2011 | Cobb |
| 2011/0208004 A1 | 8/2011 | Feingold et al. |
| 2011/0237882 A1 | 9/2011 | Saito |
| 2011/0237884 A1 | 9/2011 | Saito |
| 2011/0238977 A1 | 9/2011 | Talbert et al. |
| 2011/0245605 A1 | 10/2011 | Jacobsen et al. |
| 2011/0263941 A1 | 10/2011 | Wright et al. |
| 2011/0288374 A1 | 11/2011 | Hadani et al. |
| 2011/0295061 A1 | 12/2011 | Haramaty et al. |
| 2012/0004508 A1 | 1/2012 | McDowall et al. |
| 2012/0029279 A1 | 2/2012 | Kucklick |
| 2012/0035419 A1 | 2/2012 | Ashida et al. |
| 2012/0035434 A1 | 2/2012 | Ferren et al. |
| 2012/0041267 A1 | 2/2012 | Benning et al. |
| 2012/0041534 A1 | 2/2012 | Clerc et al. |
| 2012/0050592 A1 | 3/2012 | Oguma |
| 2012/0078052 A1 | 3/2012 | Cheng |
| 2012/0113506 A1 | 5/2012 | Gmitro et al. |
| 2012/0120282 A1 | 5/2012 | Goris |
| 2012/0140302 A1 | 6/2012 | Xie et al. |
| 2012/0147229 A1 | 6/2012 | Shah et al. |
| 2012/0265196 A1 | 10/2012 | Turner et al. |
| 2012/0293699 A1 | 11/2012 | Blanquart et al. |
| 2012/0307030 A1 | 12/2012 | Blanquart |
| 2013/0010166 A1 | 1/2013 | Morisaki et al. |
| 2013/0126707 A1 | 5/2013 | Blanquart |
| 2013/0126708 A1 | 5/2013 | Blanquart |
| 2013/0126709 A1 | 5/2013 | Blanquart |
| 2013/0144122 A1 | 6/2013 | Adair et al. |
| 2013/0158346 A1 | 6/2013 | Soper et al. |
| 2013/0176409 A1 | 7/2013 | Kotani et al. |
| 2013/0222165 A1 | 8/2013 | David et al. |
| 2013/0242069 A1 | 9/2013 | Kobayashi |
| 2013/0292854 A1 | 11/2013 | Lua et al. |
| 2013/0300837 A1 | 11/2013 | DiCarlo et al. |
| 2014/0052004 A1 | 2/2014 | D'Alfonso et al. |
| 2014/0073852 A1 | 3/2014 | Banik et al. |
| 2014/0104466 A1 | 4/2014 | Fossum |
| 2014/0160259 A1 | 6/2014 | Blanquart et al. |
| 2014/0175591 A1 | 6/2014 | Tian et al. |
| 2014/0198240 A1 | 7/2014 | Rhoads |
| 2014/0203084 A1 | 7/2014 | Wang |
| 2014/0217268 A1 | 8/2014 | Schleipen et al. |
| 2014/0267851 A1 | 9/2014 | Rhoads |
| 2014/0275783 A1 | 9/2014 | Blanquart |
| 2014/0285645 A1 | 9/2014 | Blanquart et al. |
| 2014/0300698 A1 | 10/2014 | Wany |
| 2014/0354788 A1 | 12/2014 | Yano |
| 2014/0364689 A1 | 12/2014 | Adair et al. |
| 2015/0215560 A1 | 7/2015 | Blanquart et al. |
| 2016/0190197 A1 | 6/2016 | Blanquart |

FOREIGN PATENT DOCUMENTS

| | | |
|---|---|---|
| CN | 1953193 A | 4/2007 |
| CN | 100407433 C | 7/2008 |
| CN | 101214154 A | 7/2008 |
| CN | 100502024 C | 6/2009 |
| CN | 101640211 A | 2/2010 |
| CN | 101715644 A | 5/2010 |
| CN | 101848344 A | 9/2010 |
| CN | 101848344 A | 9/2010 |
| CN | 101978598 A | 2/2011 |
| CN | 103636000 A | 3/2014 |
| CN | 103650476 A | 3/2014 |
| EP | 1618833 A1 | 1/2006 |
| EP | 1628348 A1 | 2/2006 |
| EP | 2108305 A1 | 10/2009 |
| EP | 2234387 A1 | 9/2010 |
| EP | 2302905 A1 | 3/2011 |
| EP | 2442558 A1 | 4/2012 |
| IL | 229396 | 7/2016 |
| IL | 229397 | 7/2016 |
| JP | 2001339057 | 7/2001 |
| JP | 2002-329851 | 11/2002 |

(56) References Cited

FOREIGN PATENT DOCUMENTS

| | | |
|---|---|---|
| JP | 2006-025852 | 2/2006 |
| JP | 2006-049361 | 2/2006 |
| JP | 2007-228460 | 9/2007 |
| JP | 2008-48313 | 2/2008 |
| JP | 2008-235478 | 10/2008 |
| JP | 2008-290817 | 12/2008 |
| JP | 2009206958 A | 9/2009 |
| JP | 2010-252396 | 11/2010 |
| JP | 2010-273757 | 12/2010 |
| WO | 9413191 | 6/1994 |
| WO | 1996005693 A1 | 2/1996 |
| WO | 200108549 A1 | 2/2001 |
| WO | 2004093438 | 10/2004 |
| WO | 2006080015 A2 | 8/2006 |
| WO | 2006129762 A1 | 12/2006 |
| WO | 2009135255 | 11/2009 |
| WO | 2012155142 A1 | 11/2012 |
| WO | 2012155143 A1 | 11/2012 |
| WO | 2012155150 A1 | 11/2012 |
| WO | 2012155152 A1 | 11/2012 |
| WO | 2014018948 A2 | 1/2014 |
| WO | 2014145246 A1 | 9/2014 |
| WO | 2014145248 A1 | 9/2014 |

* cited by examiner

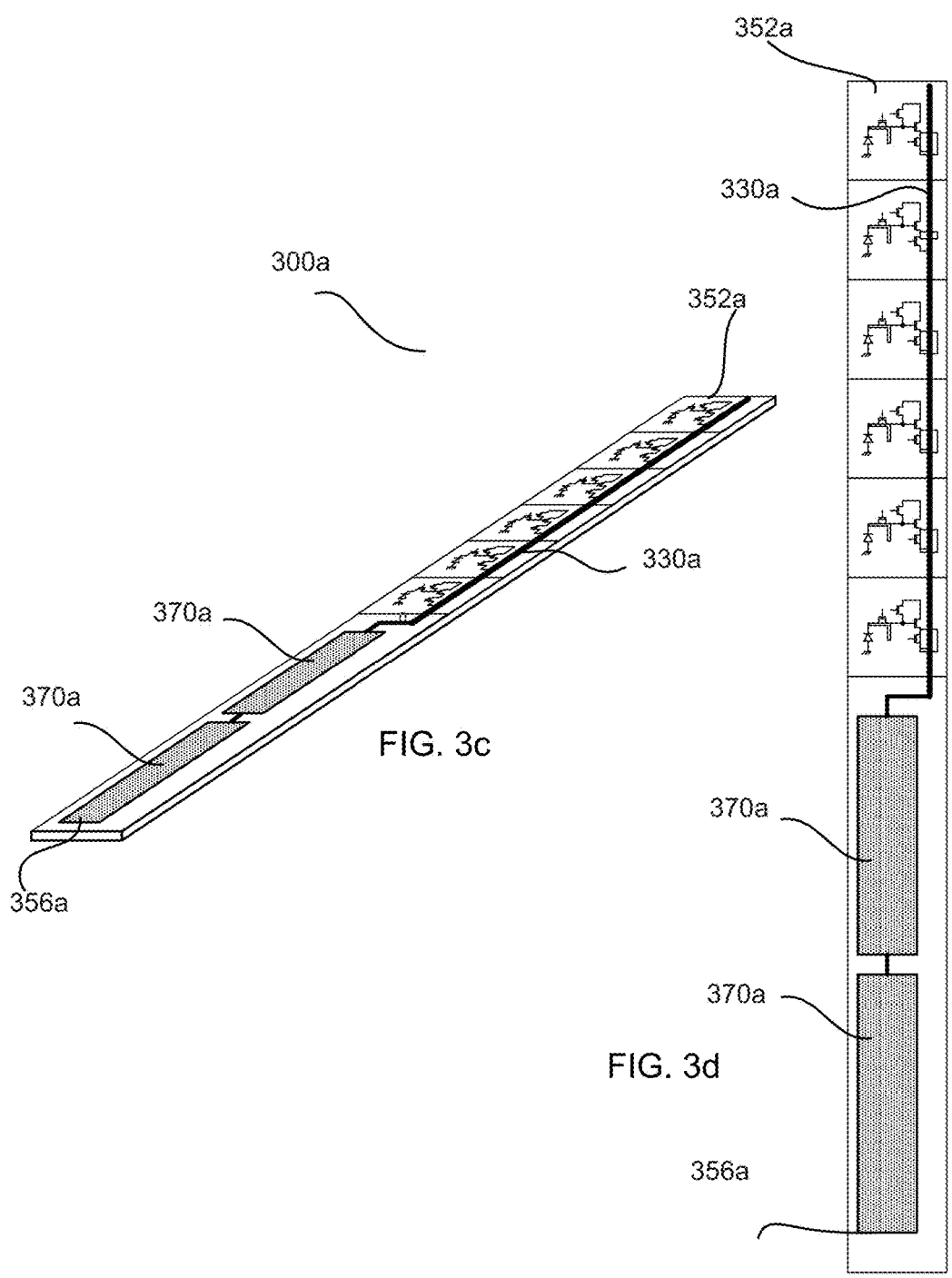

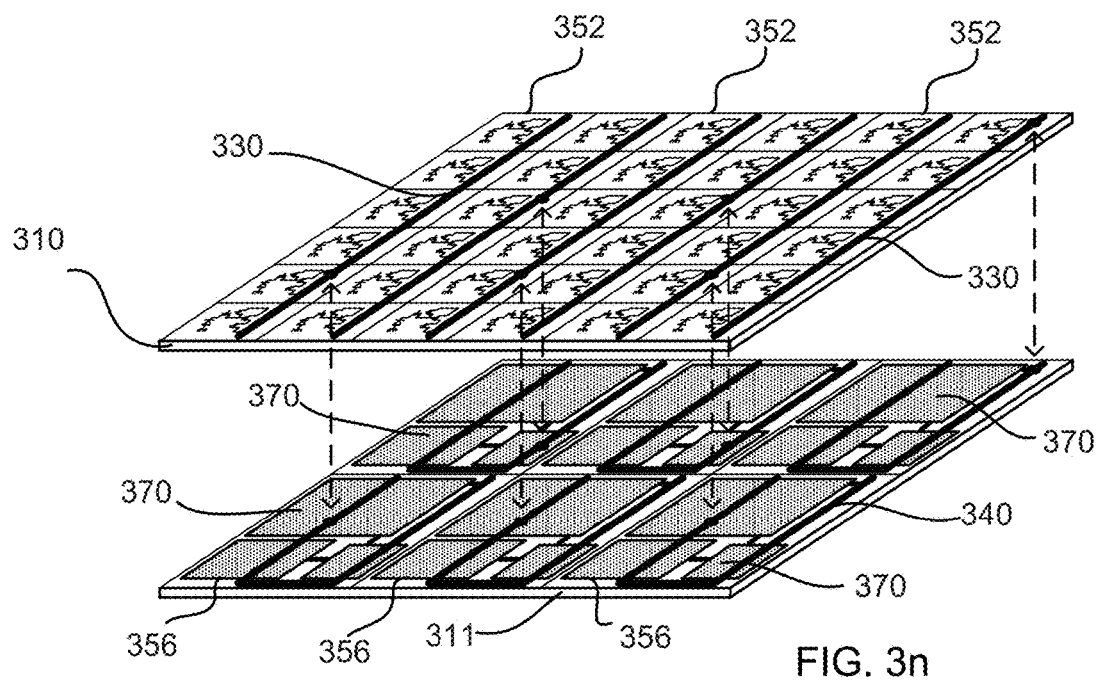
FIG. 3n
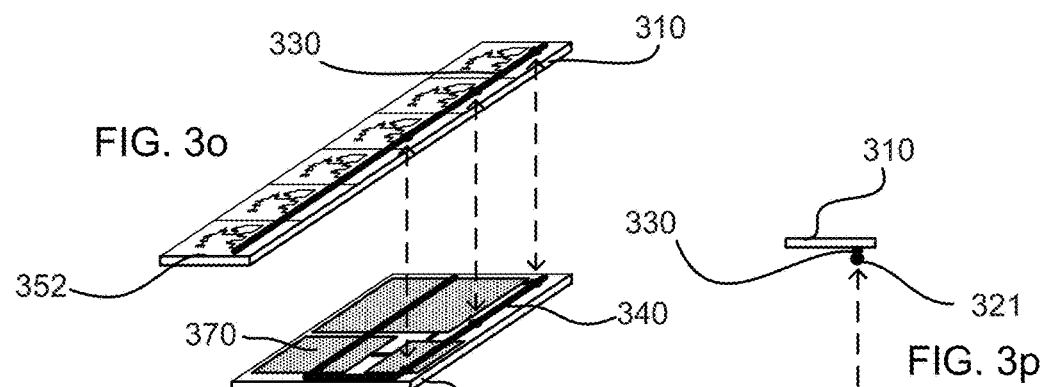
FIG. 3o
FIG. 3p
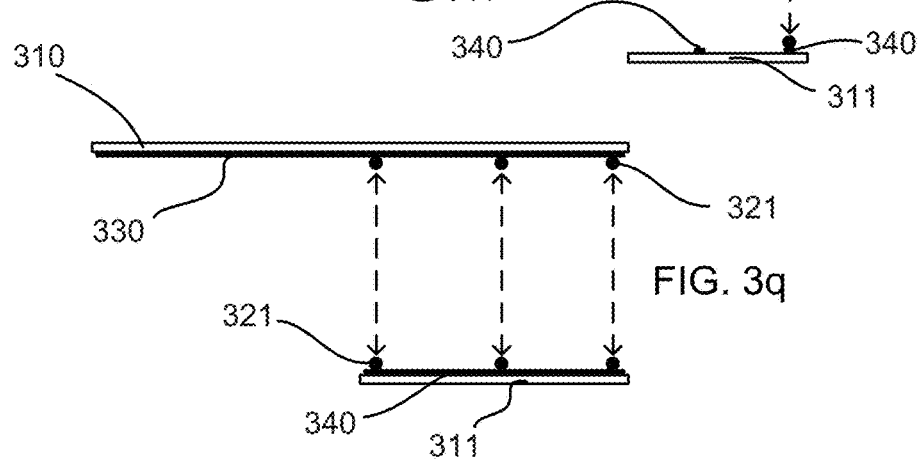
FIG. 3q

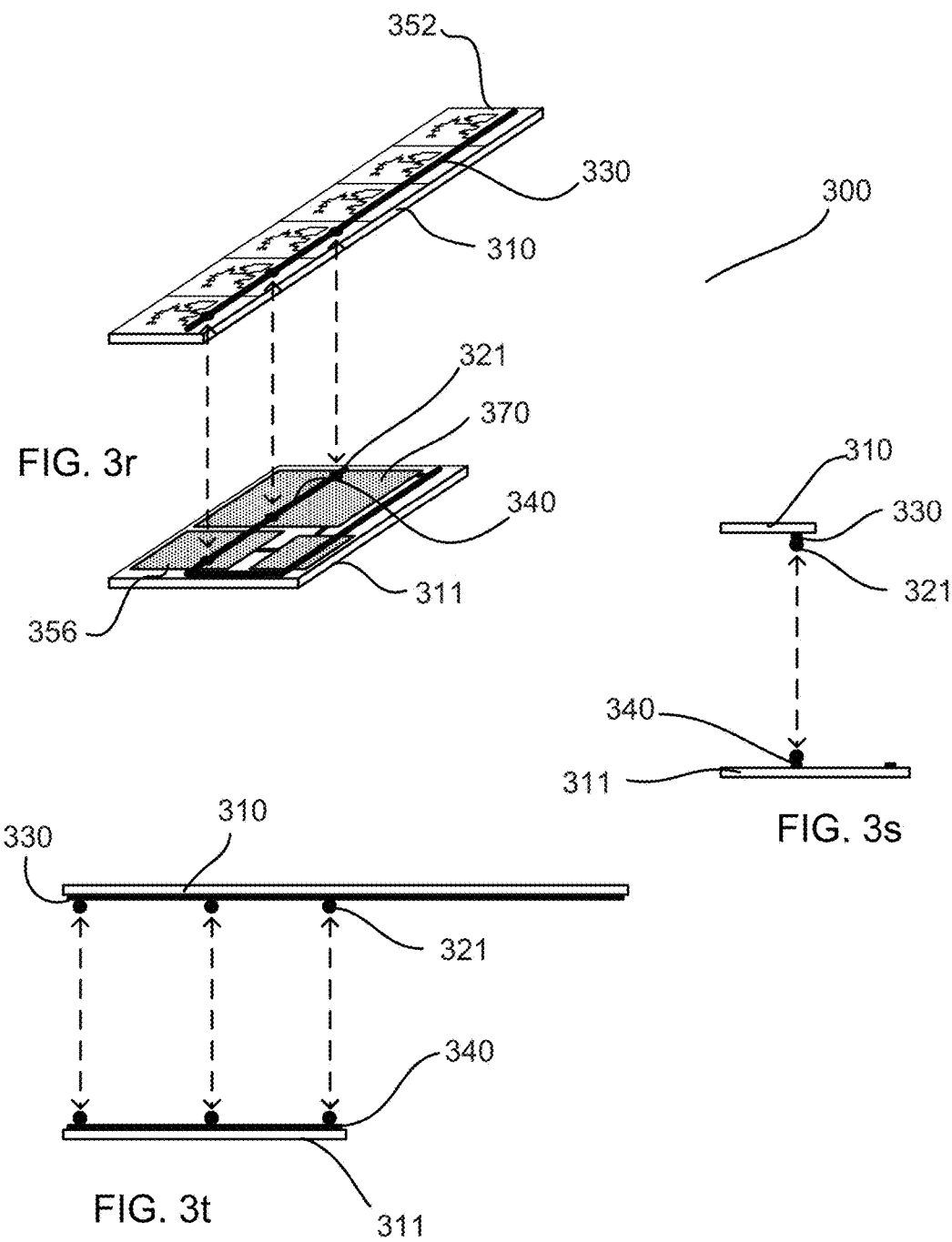

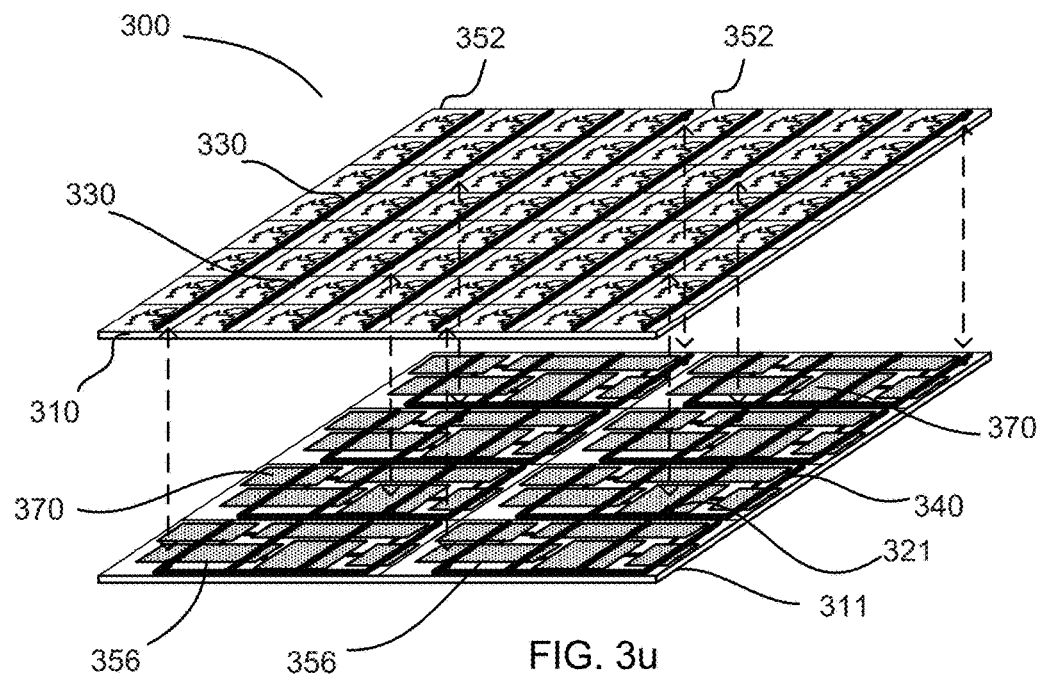
FIG. 3u
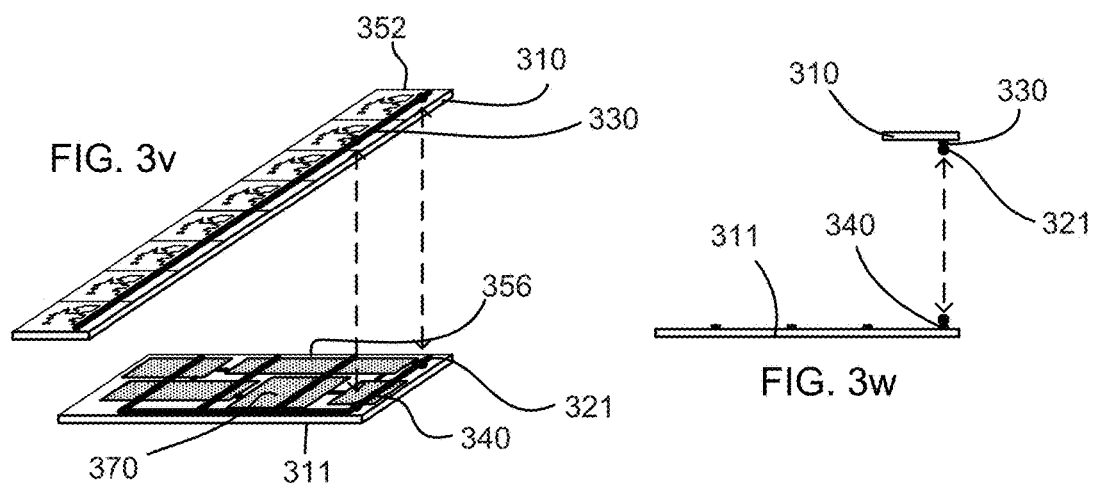
FIG. 3v
FIG. 3w
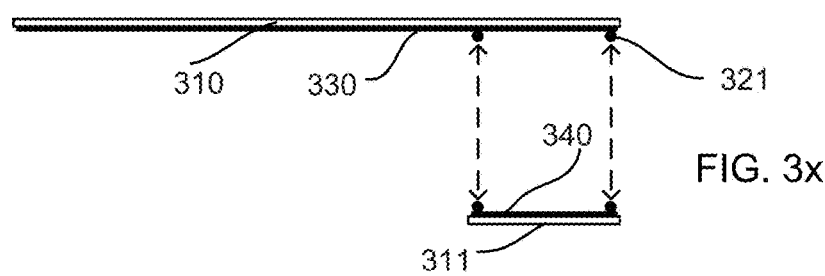
FIG. 3x

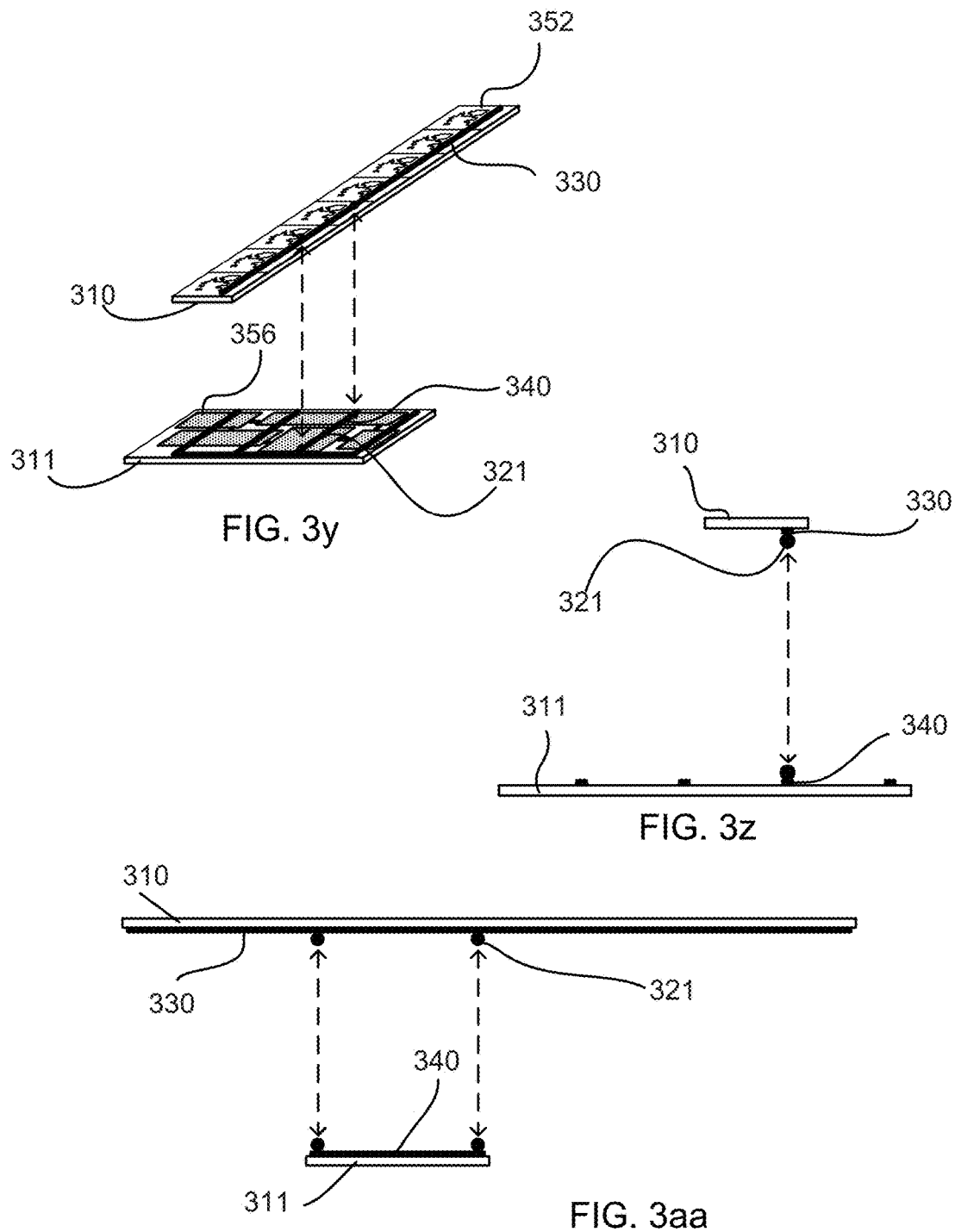

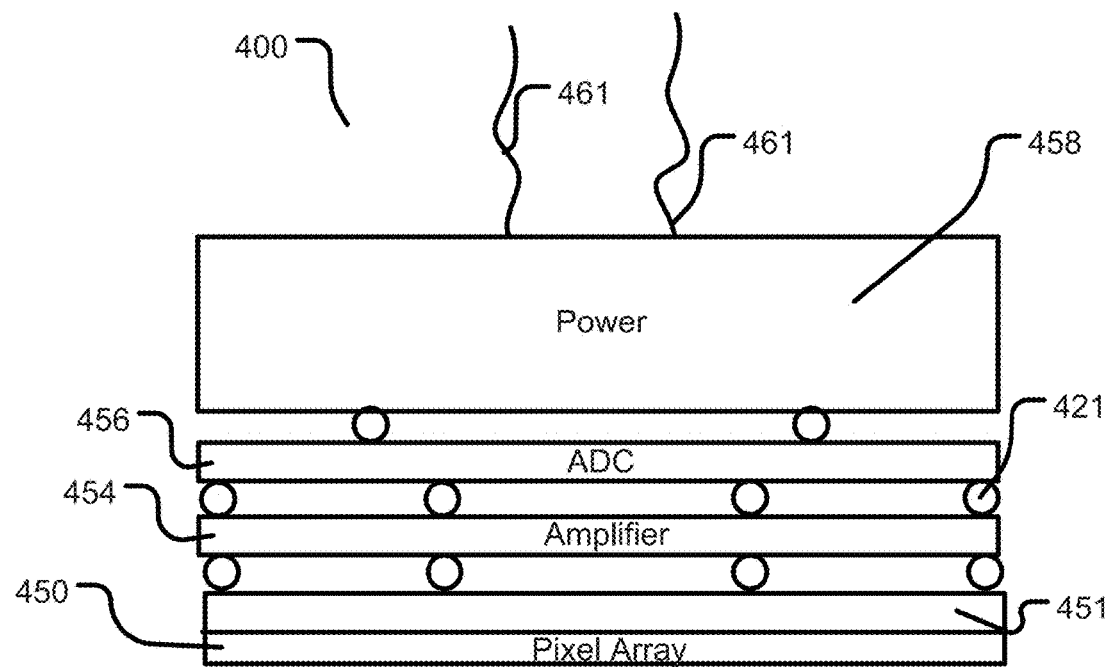
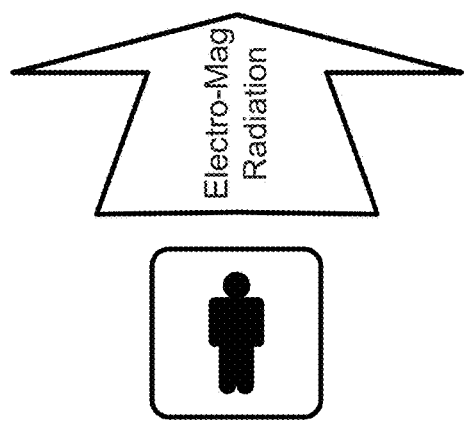
FIG. 4

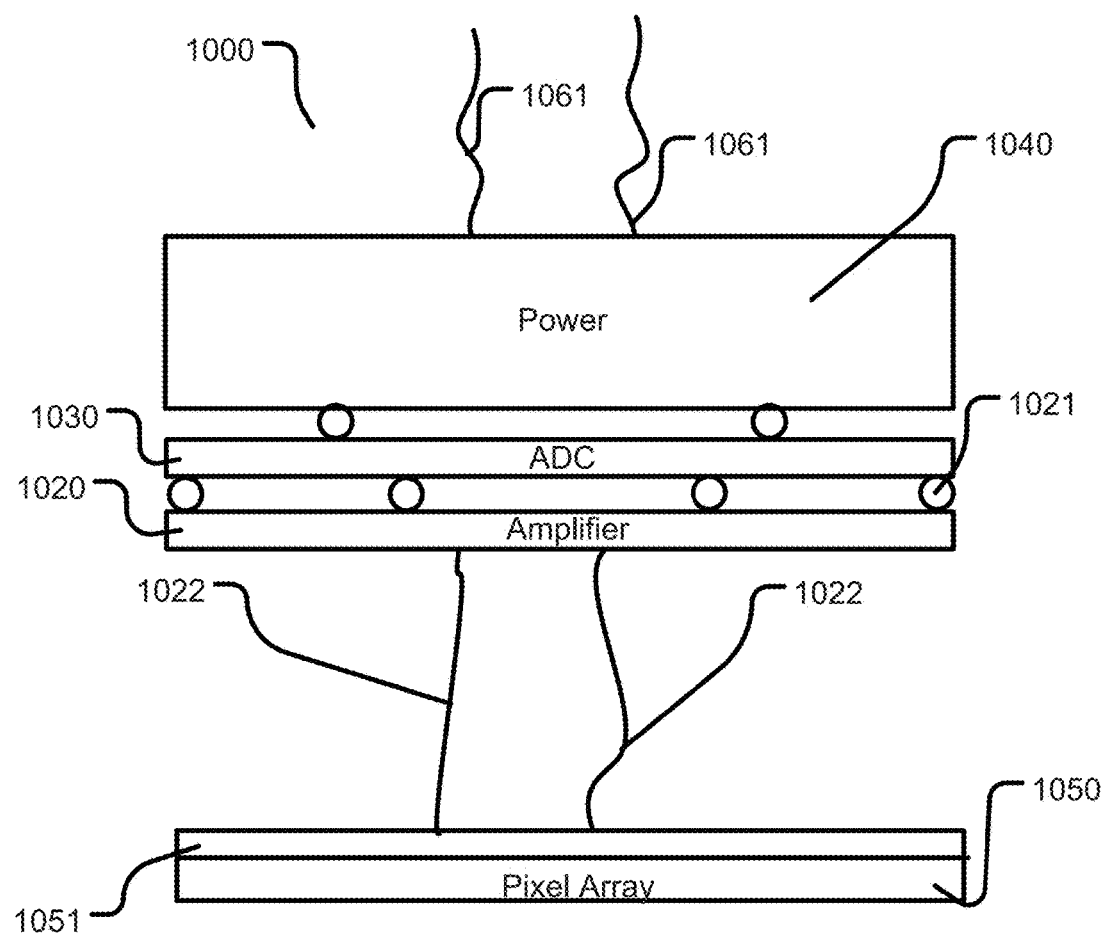
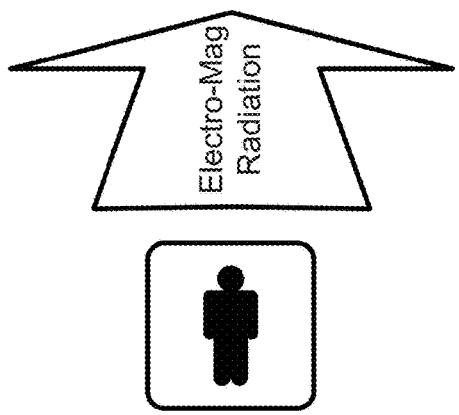
FIG. 10

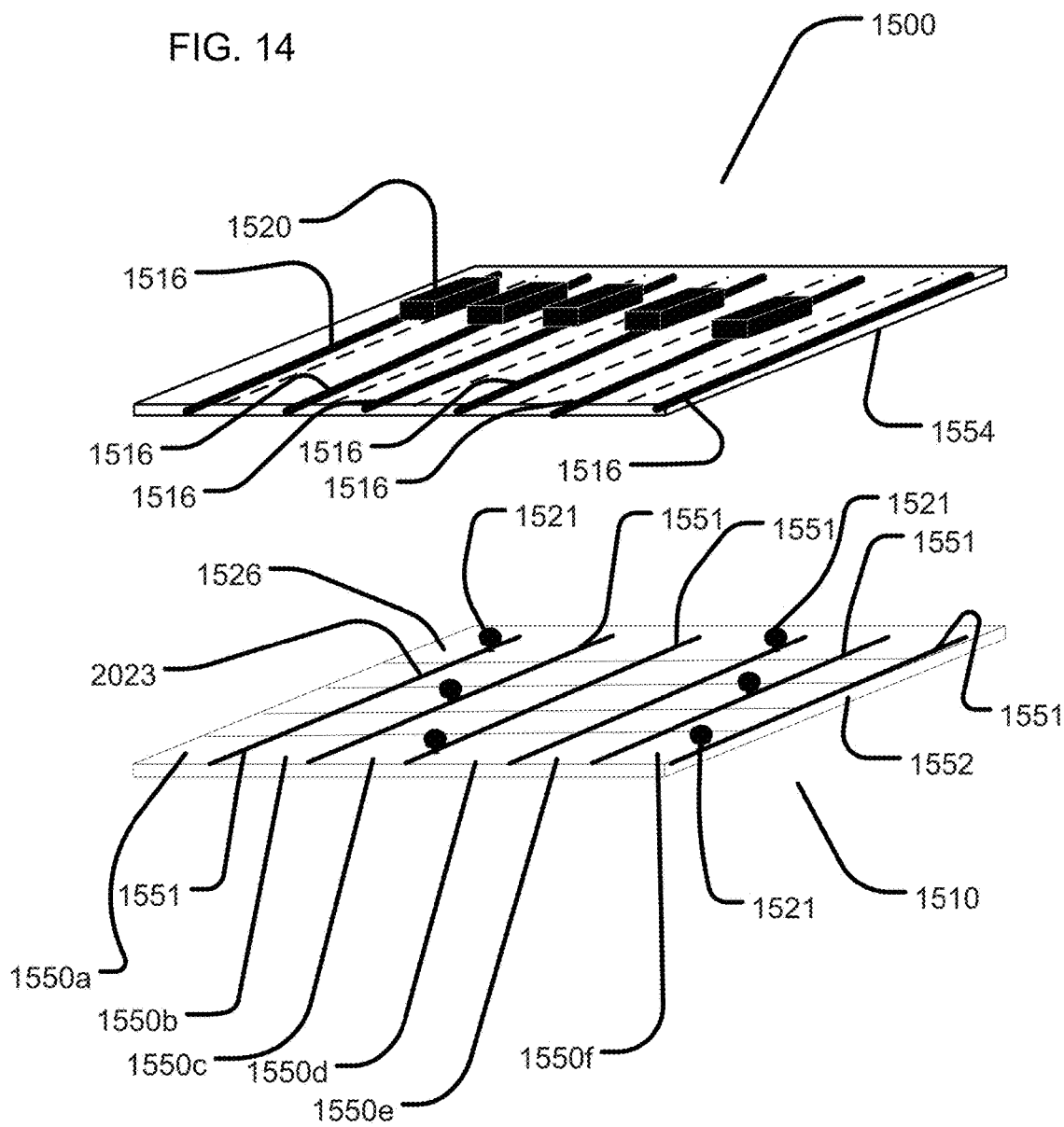

IMAGE SENSOR WITH TOLERANCE OPTIMIZING INTERCONNECTS

CROSS-REFERENCE TO RELATED APPLICATIONS

This application is a continuation of U.S. patent application Ser. No. 13/471,274, filed May 14, 2012, entitled "IMAGE SENSOR WITH TOLERANCE OPTIMIZING INTERCONNECTS," now U.S. Pat. No. 9,153,609, which claims the benefit of: (1) U.S. Provisional Application No. 61/485,432, filed May 12, 2011; (2) U.S. Provisional Application No. 61/485,435, filed May 12, 2011; (3) U.S. Provisional Application No. 61/485,440, filed May 12, 2011; and, (4) U.S. Provisional Application No. 61/485,426, filed May 12, 2011, which are all hereby incorporated by reference herein in their entireties, including but not limited to those portions that specifically appear hereinafter, the incorporation by reference being made with the following exception: In the event that any portion of the above-referenced provisional applications are inconsistent with this application, this application supersedes said above-referenced provisional applications.

STATEMENT REGARDING FEDERALLY SPONSORED RESEARCH OR DEVELOPMENT

Not Applicable.

BACKGROUND

The disclosure relates generally to electromagnetic sensing and sensors and also relates to low energy electromagnetic input conditions as well as low energy electromagnetic throughput conditions. The disclosure relates more particularly, but not necessarily entirely, to optimizing the tolerances desired for using a stacking scheme for a hybrid image sensor with minimal vertical interconnects between substrates and associated systems, methods and features.

There has been a popularization of the number of electronic devices that utilize and include the use of imaging/camera technology in general. For example, smartphones, tablet computers, and other handheld computing devices all include and utilize imaging/camera technology. The use of imaging/camera technology is not limited to the consumer electronics industry. Various other fields of use also utilize imaging/camera technology, including various industrial applications, medical applications, home and business security/surveillance applications, and many more. In fact, imaging/camera technology is utilized in nearly all industries.

Due to such popularization, the demand for smaller and smaller high definition imaging sensors has increased dramatically in the marketplace. High resolution and high definition means that more data and must be moved in a relatively smaller space. The device, system and methods of the disclosure may be utilized in any imaging application where size and form factor are considerations. Several different types of imaging sensors may be utilized by the disclosure, such as a charged-couple device (CCD), or a complementary metal-oxide semiconductor (CMOS), or any other image sensor currently known or that may become known in the future.

CMOS image sensors typically mount the entire pixel array and related circuitry, such as analog-digital converters and/or amplifiers, on a single chip. The size limitations of a CMOS image sensor often require that increasing more data is being moved within increasingly smaller confines. The contact pads between circuits can be manufactured smaller and smaller between the sensor and other important functions, such as signal processing, due to the number of considerations that must be accounted for in the design and manufacture of a CMOS image sensor. Thus, for example, increasing the pixel array area may come with a trade-off in other areas, such as A/D conversion or other signal processing functions, because of the decreased area in which the related circuitry may occupy.

The disclosure optimizes and maximizes the pixel array without sacrificing quality of the signal processing by optimizing and maximizing the pixel array on a first substrate and stacking related circuitry on subsequent substrates. The disclosure utilizes advancements in back-side illumination and other areas to take advantage of optimizing the area of the pixel array on a substrate. The stacking scheme and structure allow highly functional, large-scale circuits to be utilized while maintaining a small chip size.

The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out in the appended claims.

BRIEF DESCRIPTION OF THE DRAWINGS

The features and advantages of the disclosure will become apparent from a consideration of the subsequent detailed description presented in connection with the accompanying drawings in which:

FIG. 3c illustrates a perspective view of a single column comprising pixels and supporting circuitry taken from FIG. 3a;

FIG. 3d illustrates a top view of a single column comprising pixels and supporting circuitry taken from FIG. 3b;

FIG. 3n illustrates a perspective view of an embodiment of an imaging sensor built on a plurality of substrates wherein a plurality of pixel columns forming the pixel array are located on the first substrate and a plurality of circuit columns are located on a second substrate, wherein the circuit columns are two pixels in width and half of the length of the pixel column, and showing a plurality of electrical connections and communication between the plurality of pixel columns and associated or corresponding columns of circuitry;

FIG. 3o illustrates a perspective view of a single column of pixels and a single column of circuitry taken from the right most column of FIG. 3n showing an electrical connection therebetween;

FIG. 3p illustrates a front view of the single column of pixels and the single column of circuitry taken from FIGS. 3n and 3o showing an electrical connection therebetween;

FIG. 3q illustrates a side view of the single column of pixels and the single column of circuitry taken from FIGS. 3n and 3o showing an electrical connection therebetween;

FIG. 3r illustrates a perspective view of a single column of pixels and a single column of circuitry taken from the left most column of FIG. 3n showing an electrical connection therebetween;

FIG. 3s illustrates a front view of the single column of pixels and the single column of circuitry taken from FIGS. 3n and 3r showing an electrical connection therebetween;

FIG. 3t illustrates a side view of the single column of pixels and the single column of circuitry taken from FIGS. 3n and 3r showing an electrical connection therebetween;

FIG. 3u illustrates a perspective view of an embodiment of an imaging sensor built on a plurality of substrates wherein a plurality of pixel columns forming the pixel array are located on the first substrate and a plurality of circuit columns are located on a second substrate, wherein the circuit columns are four pixels in width, and showing a plurality of electrical connections and communication between the plurality of pixel columns and associated or corresponding columns of circuitry;

FIG. 3v illustrates a perspective view of a single column of pixels and a single column of circuitry taken from the right most column of FIG. 3u showing an electrical connection therebetween;

FIG. 3w illustrates a front view of the single column of pixels and the single column of circuitry taken from FIGS. 3u and 3v showing an electrical connection therebetween;

FIG. 3x illustrates a side view of the single column of pixels and the single column of circuitry taken from FIGS. 3u and 3v showing an electrical connection therebetween;

FIG. 3y illustrates a perspective view of a single column of pixels and a single column of circuitry taken from the column to the left of adjacent to the right most column of FIG. 3u showing an electrical connection therebetween;

FIG. 3z illustrates a front view of the single column of pixels and the single column of circuitry taken from FIGS. 3u and 3y showing an electrical connection therebetween;

FIG. 3aa illustrates a side view of the single column of pixels and the single column of circuitry taken from FIGS. 3u and 3y showing an electrical connection therebetween;

FIG. 4 illustrates an embodiment of an imaging sensor built on a plurality of substrates and also illustrating an embodiment of the specific placement of support circuits in accordance with the teachings and principles of the disclosure;

FIG. 10 illustrates an embodiment of an image sensor wherein the pixel array is more remotely located from all said supporting circuits in accordance with the teachings and principles of the disclosure;

FIG. 14 illustrates an embodiment of an imaging sensor built on a plurality of substrates having a front illuminated pixel array in accordance with the teachings and principles of the disclosure;

FIG. 15 illustrates an embodiment of an imaging sensor having pixel array divided into read areas containing a plurality of pixels;

DETAILED DESCRIPTION

Figure 1A:
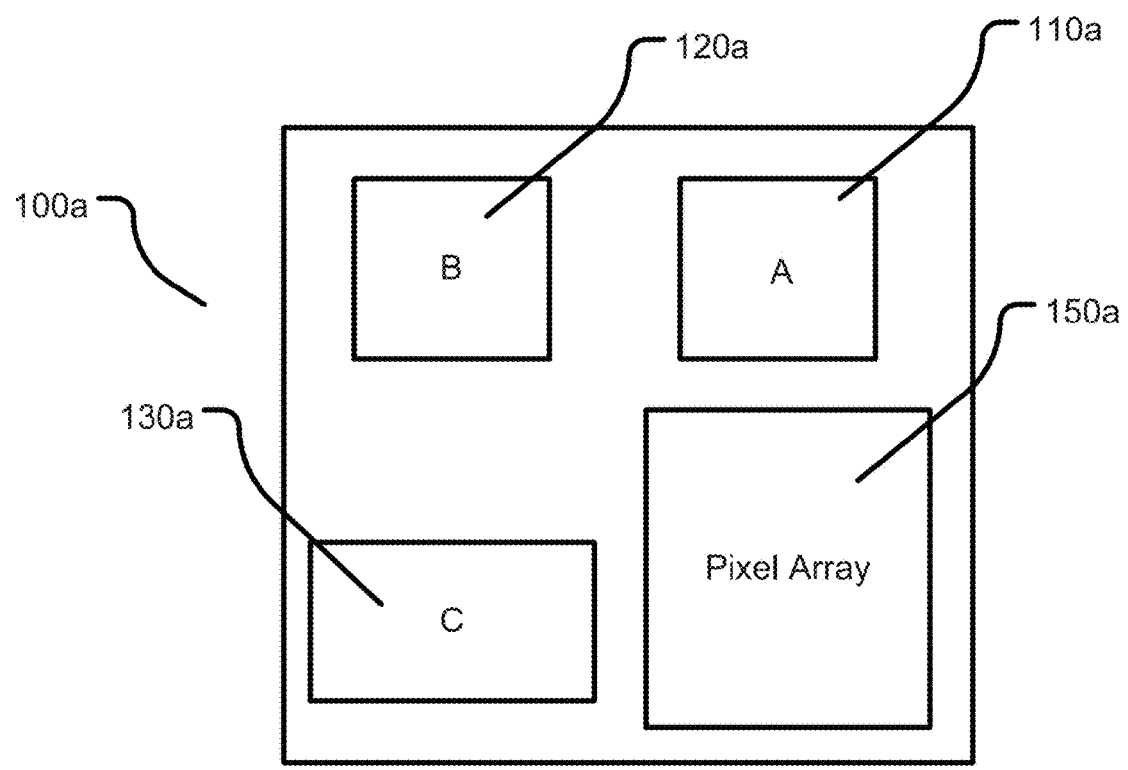
FIG. 1a is a schematic view of an embodiment of an imaging sensor constructed on a single substrate.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the devices, systems, methods and processes for staggering ADC or column circuit bumps in a column or sub-column hybrid image sensor using vertical interconnects are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

It must be noted that, as used in this specification and the appended claims, the singular forms Aa,@ Aan,@ and Athe@ include plural referents unless the context clearly dictates otherwise.

In describing and claiming the subject matter of the disclosure, the following terminology will be used in accordance with the definitions set out below.

As used herein, the terms Acomprising,@ Aincluding,@ Acontaining,@ Acharacterized by,@ and grammatical equivalents thereof are inclusive or open-ended terms that do not exclude additional, unrecited elements or method steps.

As used herein, the phrase Aconsisting of@ and grammatical equivalents thereof exclude any element or step not specified in the claim.

As used herein, the phrase Aconsisting essentially of@ and grammatical equivalents thereof limit the scope of a claim to the specified materials or steps and those that do not materially affect the basic and novel characteristic or characteristics of the claimed disclosure.

As used herein, the term Aproximal@ shall refer broadly to the concept of a portion nearest an origin.

As used herein, the term Adistal@ shall generally refer to the opposite of proximal, and thus to the concept of a portion farther from an origin, or a furthest portion, depending upon the context.

Digital imaging, whether still or movie, has many constraints placed upon it with regard to the devices used to record the image data. As discussed herein, an imaging sensor may include a pixel array and supporting circuits that are disposed on at least one substrate. Devices usually have practical and optimal constraints on the form factor of the imaging sensor depending upon the application. With most applications, especially for commercial use, size is usually a constraint. Even in outer space applications where size would seemingly be the least constrained, size is still an issue because the imaging device needs to be orbitally launched and overcome the force of gravity. Additionally, and especially in consumer electronics, any bulk added by the imaging device/camera takes away from possible other functional hardware or battery capacity/life. Thus, size is nearly always a constraint that must be addressed in any application using an imaging sensor.

In many cases, the form factor of an imaging device is constrained. There may be unlimited area or real estate laterally/horizontally, relative to the pixel array, or there may be an abundance of space directly behind a pixel array vertically. Often it is not the pixel array that is the only consideration for fitment, but it is the supporting circuitry that needs to be accommodated. The supporting circuits may be, but are not necessarily limited to, analog to digital converters, power circuits, power harvesters, amplifier circuits, dedicated signal processors and filters, serializers for data transmission, etc. In addition to circuits, physical property elements may be required, such as light filters and lenses. All of the above must be considered when deciding on and designing the form factor of an imaging device and traditionally the industry has chosen lateral or horizontal placement of supporting circuits when designing the image sensors of the day. Yet, there are many applications that would benefit from a more vertical rather than lateral or horizontal form factor.

An example of an application that would benefit from an imaging device having a relatively vertical (relative to the pixel array) form factor would be in the fields of use requiring the use of a scope. For example, industrial scopes and medical endoscopes would benefit from an image sensor that could be housed within a lumen of the device. In such a scope application, an image sensor that could be disposed in the lumen of the scope may be advantageous. The inside diameter (if round) of the lumen would then define maximum diameter (round) of the image sensor. With a popular lumen size range of 3 mm to 15 mm, it will be appreciated that the image sensor will be greatly limited in form factor considerations in the lateral direction due to the inside diameter constraints. Accordingly, a more vertical configuration may be advantageous.

Although size is an issue as stated above, pixel count numbers continue to climb industry wide no matter the specific application, and often eclipse the mediums that are used to actually view the images after they have been recorded, such as a computer monitor or television. However, it should be understood that all pixels are not created equal. In the example above, a scope configuration may be used in a limited light application. As such, a scope based image sensor that functions well in low light situations may be advantageous. Large pixels have the ability to collect more light than small pixels simply because of their different sizes. However, the trend in the marketplace has been to increase the number of pixels in a given form factor. Logically more pixels in a given area generally mean smaller pixel size. Smaller pixels have the shortfalls of not working well in lower light and creating noise because of the electronic crowding. Additionally, more pixels equates to more boundary space relative to light gathering space. Larger pixels tend to produce better images and higher image quality because they simply have a larger ratio of light sensing portion to border portion. Both of those issues lend to the poor image quality of today small image sensors.

As pixel counts continue to grow in a given space pixel pitch decreases thereby requiring greater precision for interconnect electrical contact. Accordingly, the cost of image sensor production can increase as the need for greater precision in data handling is required for the increased pixel pitch. Current technologies may be used to achieve image sensors with increased capabilities but at increased cost as yields fall during manufacture.

The techniques and structures disclosed herein with respect to a ratio of the pixel pitch to bump pitch will allow for the following:
  Improved manufacturing reliability due to increased ability to provided alternate interconnects, i.e., interconnect redundancy;
  Maximize bump pitch size in a cost effective manner per application or field of use;
  Allows for more economical CMOS process due to the ability to use larger pixel pitch;
  Allows for more efficient bump technology access, i.e., read data from multiple buses or directly off of a pixel array;
  Allows for redundancy in CMOS process to improve yield;
  Use of localized ADC in a pre-determined or defined pixel area; and
  Allows for multiple pixel array geometries, plurality of buses, and column bump configurations to be utilized.

The above-identified issues describe the current state of the art relative to a few needs within the industry. What is needed is an image sensor having adequate resolution by way of pixel count, a vertical architecture and form factor, and as large as possible pixel size, all while constrained in a limited space. The disclosure contemplates and will discuss embodiments and methods of design that address these and potentially other issues by optimizing the size of the pixel array on a substrate/chip and remotely locating supporting circuits in a generally vertical configuration on one or more supporting substrates/chips.

High performance image sensors that use on-chip analog to digital convertors (ADC), on-chip digital and analog algorithms, on-chip complex timings, and on-chip complex analog functions provide high quality images because of the following reasons (the list below is not a complete list, but is given merely for exemplary purposes):
  No pick-up noise due to long off-chip analog data lines (if no on-chip ADC, then analog signals need to be sent off-chip);
  Lower temporal noise because digital conversion is carried out early in the data path (no extra amplifier, buffer that will add extra noise);
  Local timing optimization using complex on-chip timing generator. Because of pad count limitation, only simple timing can be performed using external system;
  Lower noise generated by I/O. On-chip systems allow for reduced pad count; and
  Faster operation can be achieved (more serial on-chip operation, reduced stray capacitances and resistances).

However the elaborated functions and processes used to provide such high quality images occupy a very large area around the pixel array and significantly lower the ratio of the pixel array size to die size. It is common to have a ratio of pixel array size to die size below 25% in an imaging system that uses on-chip processes and circuitry, including ADCs and the other elaborated functions noted above. Thus, there is a trade-off between ratio of pixel array size to die size and on-chip functions.

Therefore, most of the applications of the technology that need to use an optimized ratio of pixel array size to die size use customized image sensors without digital conversion (analog out) or with reduced analog/digital functionality and lower grade analog to digital conversion. Even in that case, the ratios of pixel array size to die size that are greater than 50% are difficult to achieve.

The disclosure demonstrates and contemplates a system and method of increasing the ratio of pixel array size to die size without sacrificing image quality. The disclosure contemplates imaging applications using a given die size and where maximized pixel array size is required or imaging applications using a given pixel array size, but where smaller die size is required.

One of the key issues of the three dimensional stacking technology is the bump pitch. Current technologies achieve a bump pitch of around 50 µm to 100 µm. In the next three to ten years, it is expected that developing technologies will permit the bump pitch to be decreased in size in a range that is equal or nearly the same size as pixel pitch.

Moreover stacked substrates/chips yield depends directly upon the bump pitch. The most frequent failure in stacked substrates/chips is an electrical short between two interconnects or bumps. As bump pitch decreases in size and becomes smaller, the planarization specification of the wafers has to be tighter. In order to absorb the wafer planarization errors, the interconnects or bumps are made or grown taller. However, excess metal in taller interconnects/bumps tends to move to the side(s) during the wafer bonding process, which may short neighboring or adjacent bumps. Higher yield and lower costs due to a relaxed wafer alignment process can be achieved by relaxing the interconnect or bump pitch.

The disclosure proposes a device, system, method of relaxing the bump pitch while working on a tighter pixel pitch.

The disclosure also contemplates an image sensor that might otherwise be manufactured with its pixel array and supporting circuitry on a single, monolithic substrate/chip and separating the pixel array from all or a majority of the supporting circuitry. The disclosure may use at least two substrates/chips, which will be stacked together using three-dimensional stacking technology. The first of the two substrates/chips may be processed using an image CMOS process. The first substrate/chip may be comprised either of a pixel array exclusively or a pixel array surrounded by limited circuitry. The second or subsequent substrate/chip may be processed using any process, and does not have to be from an image CMOS process. The second substrate/chip may be, but is not limited to, a highly dense digital process in order to integrate a variety and number of functions in a very limited space or area on the substrate/chip, or a mixed-mode or analog process in order to integrate for example precise analog functions, or a RF process in order to implement wireless capability, or MEMS (Micro-Electro-Mechanical Systems) in order to integrate MEMS devices. The image CMOS substrate/chip may be stacked with the second or subsequent substrate/chip using any three-dimensional technique. The second substrate/chip may support most, or a majority, of the circuitry that would have otherwise been implemented in the first image CMOS chip (if implemented on a monolithic substrate/chip) as peripheral circuits and therefore have increased the overall system area while keeping the pixel array size constant and optimized to the fullest extent possible. The electrical connection between the two substrates/chips may be done through interconnects, which may be wirebonds, μbump and/or TSV (Through Silicon Via).

Figure 1B:
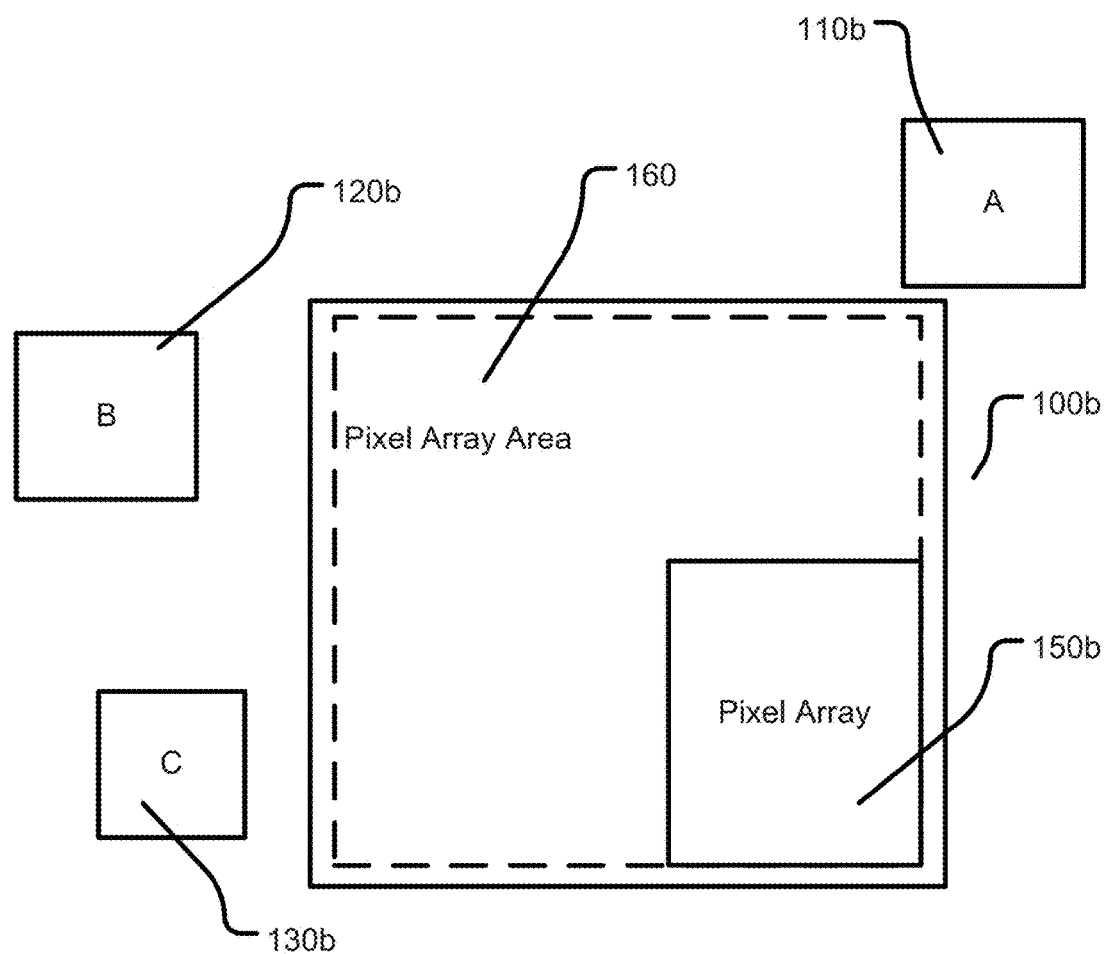
FIG. 1b is a schematic view of an embodiment of an imaging sensor, demonstrating the remote placement of processing circuits relative to a pixel array in accordance with the teachings and principles of the disclosure.

Referring now to FIGS. 1a and 1b, FIG. 1a an example of an imaging sensor of monolithic design wherein a single substrate is used as the basis of chip construction. As can be seen in FIG. 1a, a substrate 100a may comprise a pixel array 150a that is configured to receive electromagnetic energy, convert it to data, and then pass that data on to supporting circuits 110a, 120a, 130a for processing that will ultimately result in a digital image or video. The supporting circuits may include signal processing circuits such analog to digital converters 110a, amplifier circuits 130a, filter circuits, power supplying and harvesting circuits 120a, and serial processors to name only a few. Some of the supporting circuits may be located nearer to the pixel array than other circuits and connected to each pixel of the pixel array via buses. For example, amplification circuits and digital conversion circuits may be preferred to be located closer to the pixel array because that architecture may increase the clarity of the data stream and introduce minimal noise to the system. As can be seen in FIG. 1a, image sensor 100a is a schematic illustration of what is typically available in the marketplace with regard to image sensors. FIG. 1a illustrates a generally lateral placement of the supporting circuits relative to the pixel array 150a, which dominates the marketplace today because of cost and manufacture limitations. Lateral placement of the supporting circuits on the same substrate as, and with respect to, the pixel array 150a simplifies the architecture and reduces the cost of production. However, the use of a single substrate has some drawbacks and limitations, such as form factor issues, because not all applications lend themselves to a lateral or horizontal circuit placement as discussed above. As is illustrated in FIG. 1b, when the support circuits, such as 110a, 120a, 130a, are removed from the first substrate 160 there remains considerable room for a larger pixel array 150a to be located on the first substrate 160, which means more or larger pixels can be used. Given the same physical limitations in an electronic device using an imaging sensor, using the techniques and combination of features disclosed herein allows either increased pixel resolution or increased pixel size to be used. In such cases, the image sensor substrates can be reduced in size and used in more devices where size is of primary concern and yet a high quality image is desired. Specifically, the FIG. (1b) illustrates the design concept of remotely locating support circuits 110b, 120b and 130b relative to the pixel array.

Figure 2:
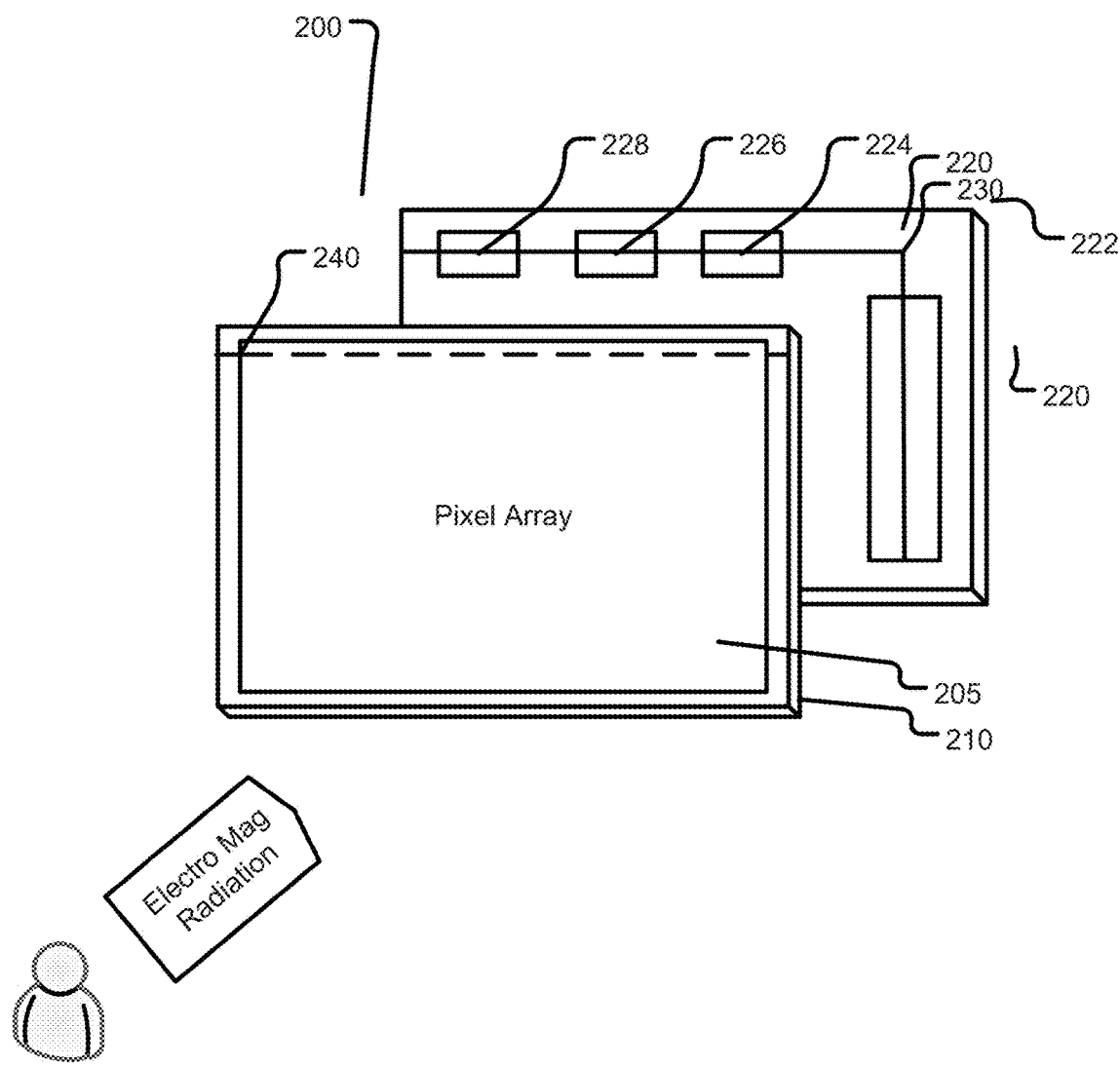
FIG. 2 illustrates a schematic view of an embodiment of an imaging sensor built on a plurality of substrates in accordance with the teachings and principles of the disclosure.

Referring primarily to FIG. 2, the use of supporting substrates to carry supporting circuits will be discussed. In an embodiment of an exemplary image sensor 200, a pixel array 205, which may comprise a plurality of pixels that are formed into a plurality of pixel columns, are positioned on a surface of a first substrate 210. Each of the plurality of pixel columns located on the first substrate 210 may be electrically connected to a read bus 240. Signal processing and image enhancement may be performed by supporting circuits located on a second substrate 220. The circuits may include signal processing circuits, such as analog to digital converters 228, amplifier circuits 226, filter circuits 224, power supplying and harvesting circuits 222, which may be formed into a plurality of circuit columns that correspond with the plurality of pixel columns on the first substrate 210. Each circuit column may be comprised of a plurality of supporting circuits that is in electronic communication with a read bus 230 or plurality of read buses corresponding to each circuit column. In other words, the signal processing circuits may be located on a second substrate or supporting substrate 220. Each of the plurality of circuit columns on the second substrate 220 may then be electronically connected to a corresponding pixel column located on the first substrate 210 through an interconnect, such as a solder bump, solder ball or via, which may be located anywhere along the physical path where the read buses 230, 240 are superimposed or overlap. It is also within the scope of this disclosure to contemplate the use of a plurality of secondary substrates, each substrate housing any needed circuits for an image sensor and in any order or combination of supporting circuits depending upon the desired function of the image sensor.

Figure 3A:
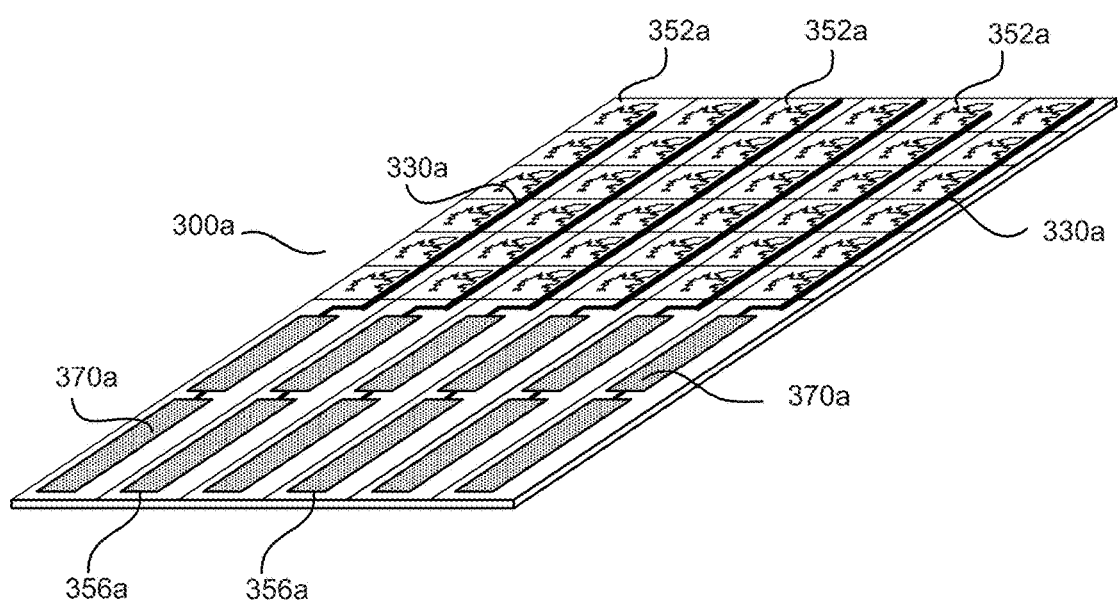
FIG. 3a illustrates a perspective view of an embodiment of an imaging sensor made on a monolithic and illustrating a plurality of columns comprising pixels and supporting circuitry, where the supporting circuitry is one pixel in width.
Figure 3B:
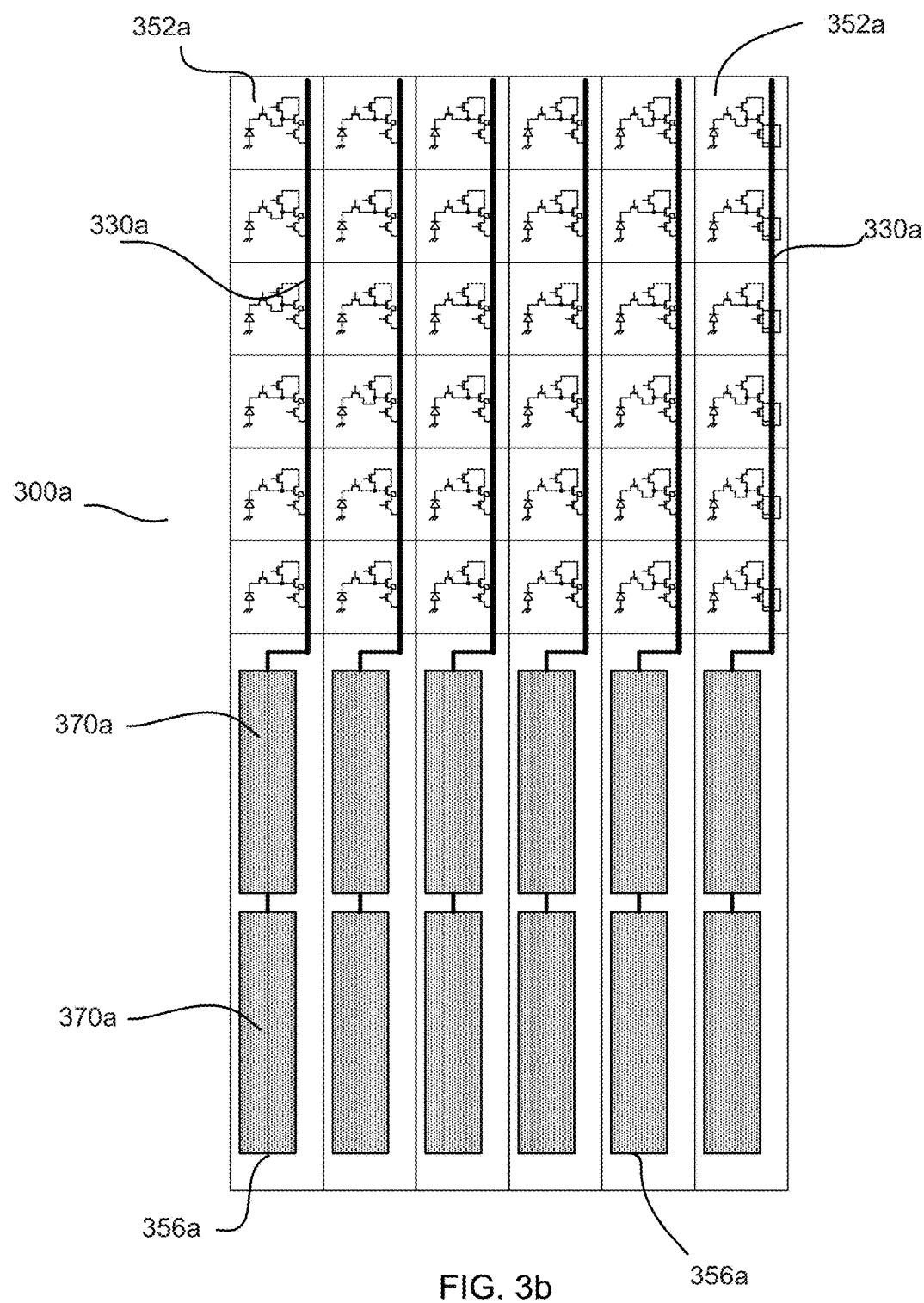
FIG. 3b illustrates a top view of an embodiment of an imaging sensor made on a monolithic and illustrating a plurality of columns comprising pixels and supporting circuitry, where the supporting circuitry is one pixel in width.

As illustrated in FIGS. 3a through 3f, an image sensor 300a may generally comprise a pixel array 350a and supporting circuitry 370a, which may comprise an analog to digital converter 317a, an amplifier 315a, a filter 314a and a clock 316a all of which may be disposed on a monolithic substrate 310a. In FIGS. 3a and 3b, a monolithic image sensor is illustrated in a perspective view and a top view, respectively. The pixel array 350a may be comprised of a plurality of pixel columns, wherein each of the plurality of pixel columns 352a comprises a plurality of individual pixels. The supporting circuitry 370a may comprise a plurality of circuit columns 356a, wherein each of the circuit columns 356a comprises circuitry to support a corresponding pixel column 352a. As illustrated in the figures, the monolithic circuit columns 356a are each one pixel in width and are locally located relative to a pixel column to which they correspond. The figures illustrate a pixel array of unshared pixels with one read bus per pixel column electrically connected to the corresponding column circuitry on one side of the image sensor only. It will be appreciated that the corresponding circuitry is one pixel wide in the embodiment, however, other configurations of support circuitry as discussed below are contemplated within the scope of this disclosure and may be used to increase the image sensor design options.

Referring now to FIGS. 3c and 3d, a single pixel column 352a comprising a plurality of pixels and a single circuit column 356a are illustrated in a perspective view and a top view, respectively. It will be appreciated that the single pixel column 352a and the corresponding circuit column 356a illustrated in the figures are taken from the image sensor 300a illustrated in FIGS. 3a and 3b and simply denote a single pixel column 352a electrically connected to a single circuit column 356a.

Figure 3E:
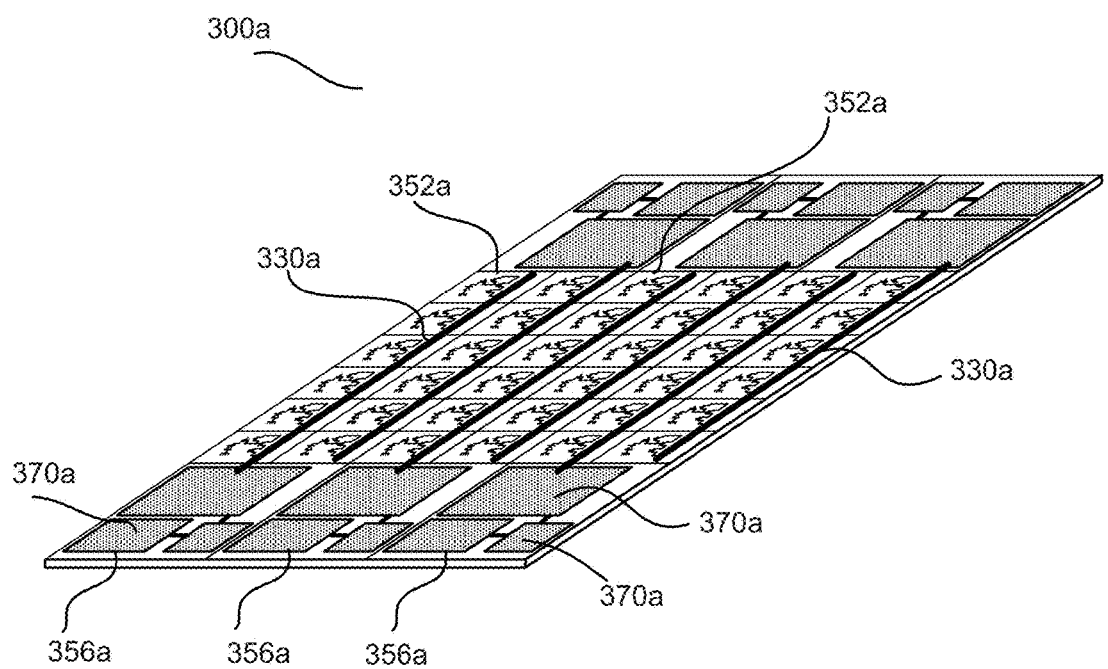
FIG. 3e illustrates a perspective view of an embodiment of an imaging sensor made on a monolithic and illustrating a plurality of columns comprising pixels and supporting circuitry, where the supporting circuitry is two pixels in width.
Figure 3F:
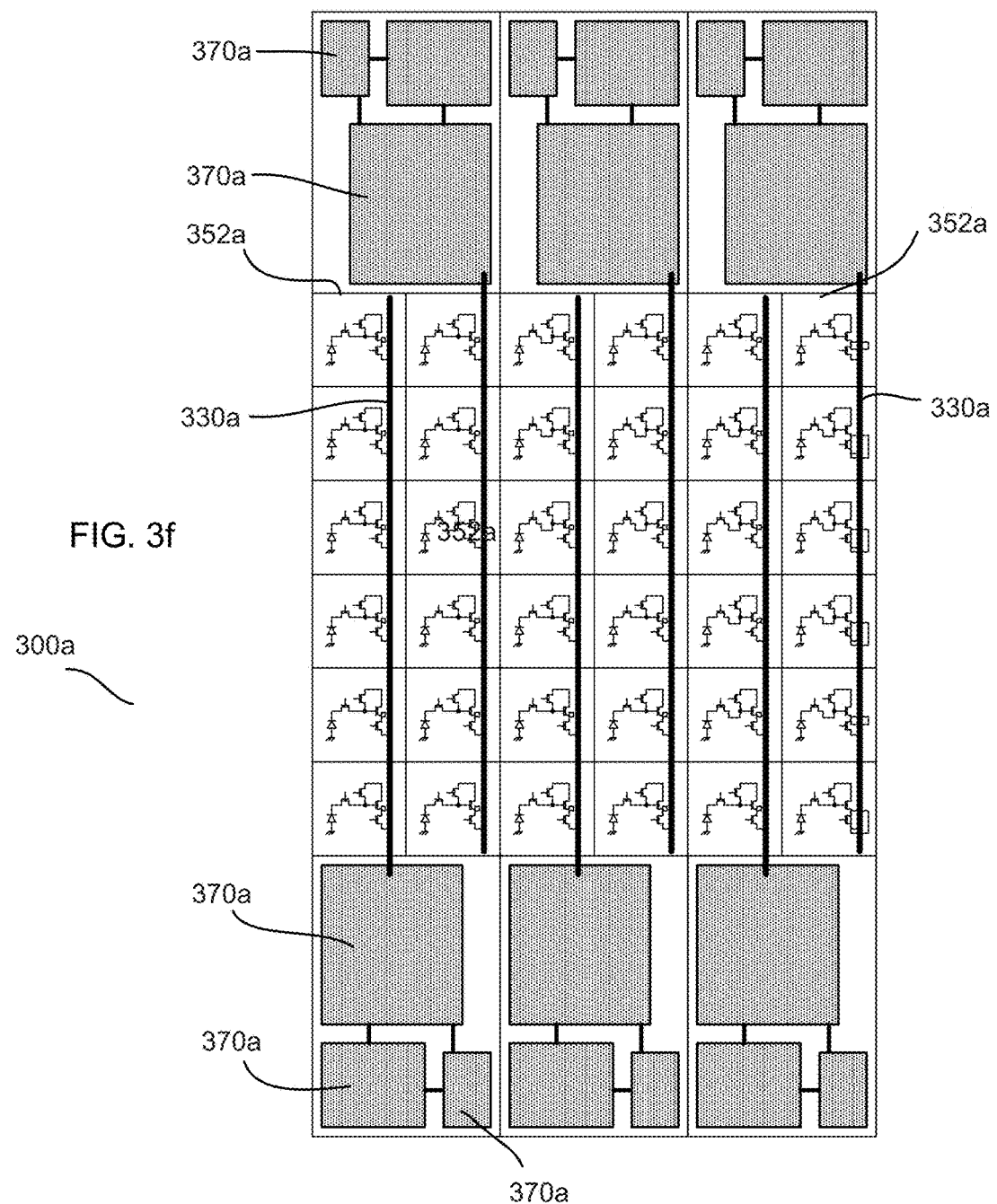
FIG. 3f illustrates a top view of an embodiment of an imaging sensor made on a monolithic and illustrating a plurality of columns comprising pixels and supporting circuitry, where the supporting circuitry is two pixels in width.

FIGS. 3e and 3f illustrate a perspective view and a top view of an embodiment of an imaging sensor 300a made on a monolithic substrate and illustrating a plurality of columns comprising pixels and supporting circuitry. In contrast to FIGS. 3a and 3b, FIGS. 3e and 3f illustrate the supporting circuitry as being two pixels in width. In the figures it can be seen that alternating pixel columns 352a read to corresponding circuitry located at opposing ends of the pixel columns 352a. Such a configuration offers variations in aspect ratios of corresponding circuit column 356a areas. Because the buses 330a read to alternating ends of the pixel array 350a, the circuit column 356a can be two pixels wide. Contrasting the sensors illustrated in FIGS. 3b and 3f, the pixel column 352a illustrated in FIG. 3b has an aspect ratio of six pixels (units) long by one pixel wide (6/1) and the circuit column 356a has a similar aspect ratio. Conversely, the image sensor illustrated in FIG. 3f has a pixel column 352a that has an aspect ratio of six pixels (units) long by one pixel wide (6/1) and the circuit column 356a has an aspect ratio of two pixels wide and three pixels long (2/3).

Figure 3G:
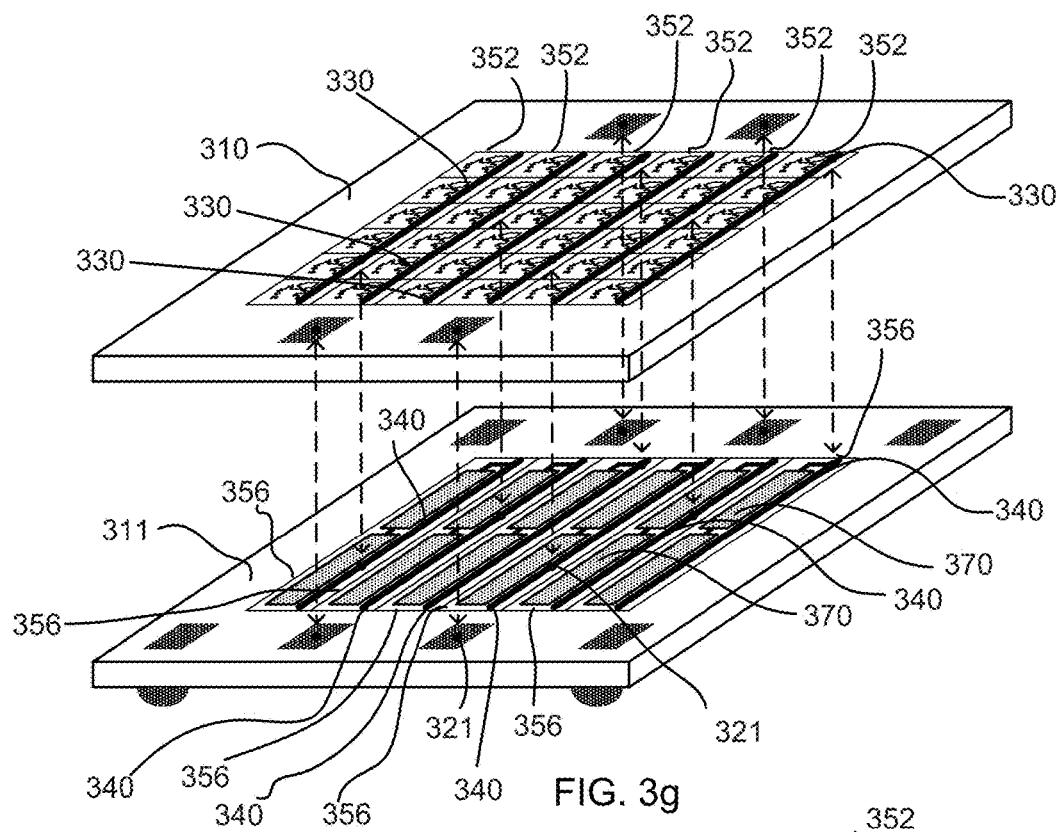
FIG. 3g illustrates a perspective view of an embodiment of an imaging sensor built on a plurality of substrates with a pixel array on the first substrate and supporting circuitry located on a second or subsequent substrate with interconnects and vias being shown connecting the plurality of substrates in accordance with the teachings and principles of the disclosure.

In contrast, the same functionality of an imaging sensor 300a built on a monolithic substrate (shown in FIGS. 3a-3f) can be provided and supplied in an imaging sensor 300 that has a much smaller dimension (in at least the lateral direction and having a much smaller area and form factor) than a monolithic substrate or chip. Referring now to FIGS. 3g through 3aa, an imaging sensor 300 will be discussed that may comprise a pixel array 350 that may be disposed on a first substrate 310, while all of the supporting circuits 370 may be remotely located (with respect to the pixel array 350 and first substrate 310) to one or more supporting substrates, such as a second substrate 311 and a third substrate 312.

It should be noted that the image sensor may be built and manufactured on a plurality of substrates. Each of the plurality of substrates may be located with respect to each other in a stacked configuration or formation, where all of the supporting substrates are stacked or aligned behind the first substrate 310, which comprises the pixel array 350, and relative to an object to be imaged. Each of the substrates in the stack may be electrically connected through interconnects 321, such as solder bumps or solder balls, vias or other forms of electrical communication. It will be appreciated that the interconnects 321 may include any known means or method for conducting electrical signals to various circuits on the same or different substrates without departing from the scope of the disclosure.

In FIGS. 3g, 3i, 3m, 3n, and 3u, each of the plurality of substrates comprising the pixel array 350 and the various supporting circuits 370 of the image sensor 300 may be of similar size in the stack, such that the plurality of substrates may be substantially aligned within the stack. In an embodiment, the first substrate 310 and the plurality of subsequent supporting substrates 311 may be stacked in substantial alignment so that a plurality of communication columns are formed in a multi-layer stack of substantially the same length and width.

Figure 11:
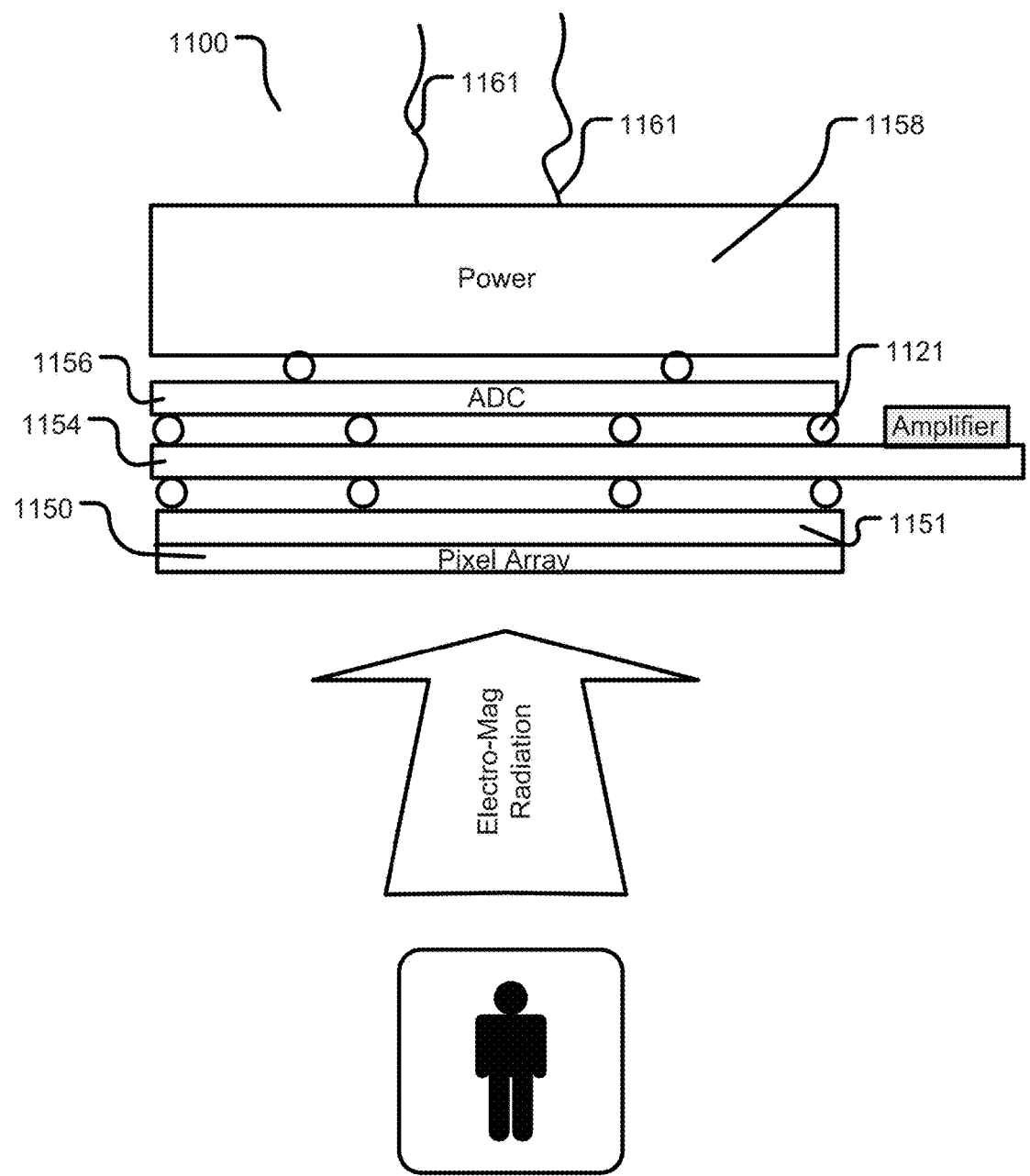
FIG. 11 illustrates an embodiment of an image sensor having stacked substrates of differing size in accordance with the teachings and principles of the disclosure.

It should be noted that in other embodiments, where the form factor will allow it, different sized substrates having different lengths and widths may be used and may be preferred in the stack. Considerations such as heat dissipation and noise, along with many more considerations, may be accounted for when designing a stacked configuration. For example, in an embodiment, a high heat circuit, such as an amplifying circuit, may be placed on a protruding portion of one of the supporting substrates within a stack (illustrated best in FIG. 11).

It should be noted that a pixel array 350 may be formed in a plurality of rows of pixels and a plurality of columns of pixels. Each pixel column 352 may comprise a plurality of pixels in a linear form factor, which is one pixel wide and AN@ pixels long. It should be further noted that each pixel column 352 will have an area value that is generally as wide as the pixel pitch and as long as is predetermined by sensor design.

Conversely, a circuit column 356, as referred to herein, is an allocated space on a substrate, other than a first substrate 310 comprising the pixel array 350, which comprises at least one support circuit 370 that is dedicated and electrically connected to, or in electrical communication with, a corresponding pixel column 352. It will be appreciated that the space occupied by the pixel column 352 may be the same as, or substantially the same as, the space occupied by the circuit column 356 that corresponds with that pixel column 352. Thus, the second or supporting substrate 311 may comprise a plurality of circuit columns 356, wherein each circuit column 356 comprises substantially the same or similar real estate area on the second substrate 311 as a corresponding pixel column 352 has area on the first substrate 310.

Additionally, each pixel column 352 is or may be in electronic communication with a read bus 330 on the first substrate 310, while the circuit column 356 is or may be in electronic communication with a read bus 340 on the second substrate 311. The two aforementioned buses 330, 340 may be electrically connected by at least one interconnect 321 that is located anywhere along the path created by, or within, the superimposition of or between the two buses 330, 340 as illustrated in FIGS. 3g through 3aa. In an embodiment, a plurality of interconnects 321 may be used to connect a single pixel column 352 to a single corresponding circuit column 356. In such an embodiment, the redundancy in the number of interconnects 321 used may provide for increased production yield or increased functionality.

As referred to herein, aspect ratio will be used to refer to the general shape of an area on a substrate. For example, an area defined as being 4 pixel units wide and 5 pixel units long will have an aspect ratio of 4/5 or 5/4. The term aspect ratio may be used generically to denote a situation where the shape of an area is considered important. For example, the concept of aspect ratio may be used to denote differences in the aspect ratios of two corresponding areas that are located on differing substrates. It should be noted that the aspect ratios of the pixel columns 352 and the circuit columns 356 illustrated in FIGS. 3g-3aa may be the same or may be different, the area of the footprint of the pixel column 352 and its corresponding circuit column 356 may be substantially the same or equal. Several examples of different aspect ratios are illustrated in FIGS. 3g through 3aa, but it should be noted that the principles of this disclosure may be applied to any number of aspect ratio configurations. However, as illustrated in the figures, the area of the circuit column 356 footprint or real estate is substantially the same as or equal to the area of the footprint or real estate of the pixel column 352. As manufacturing techniques improve or design parameters change more or less area may be needed for the supporting circuits 370 of the circuit column 356.

Figure 3H:
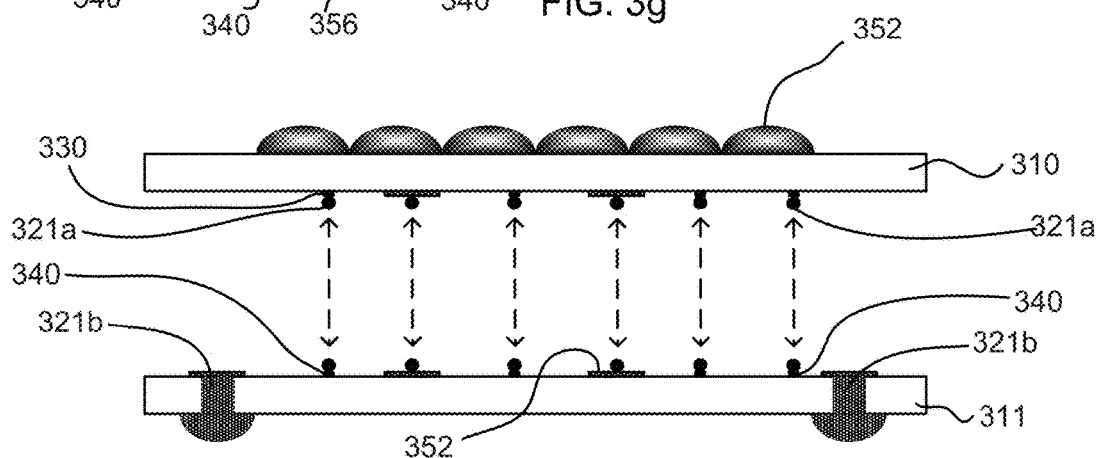
FIG. 3h illustrates a front view of the embodiment of an imaging sensor built on a plurality of substrates of FIG. 3g.

Referring specifically to FIGS. 3g and 3h, the supporting circuitry 370, which may include an amplifier, a filter, a clock or other circuitry needed to support an image sensor, may all be disposed on one or more supporting substrates, such as a second substrate 311. However, it will be appreciated that such circuits may be dispersed on one or more substrates, such as the second substrate 311, or a third substrate. Additionally, an analog to digital converter may be remotely located on one of the supporting substrates. It will be appreciated that the order and location of the supporting circuits 370 may be changed and may be located on any of the supporting substrates as desired.

As can be seen in the figures, each pixel column 352 may be associated and electrically connected to one read bus 330 on the first substrate 310, while each of the circuit columns 356 may be associated and electrically connected to one read bus 340 on the supporting substrate 311 by one or more interconnects 321, which may include both ubumps 321a and vias 321b (illustrated best in FIG. 3h). At least one interconnect 321 may be used to connect a pixel column bus 330 on the first substrate 310 to a circuit column bus 340 on the supporting substrate 311 as illustrated. The dashed arrows in FIGS. 3i, 3j, 3l, 3o, 3q, 3r, 3t, 3v, 3x, 3y and 3aa illustrate that the interconnects 321 may be located anywhere along the superimposition path of the two read buses 330 and 340 per corresponding pixel column 352 and circuit column 356.

Figure 3I:
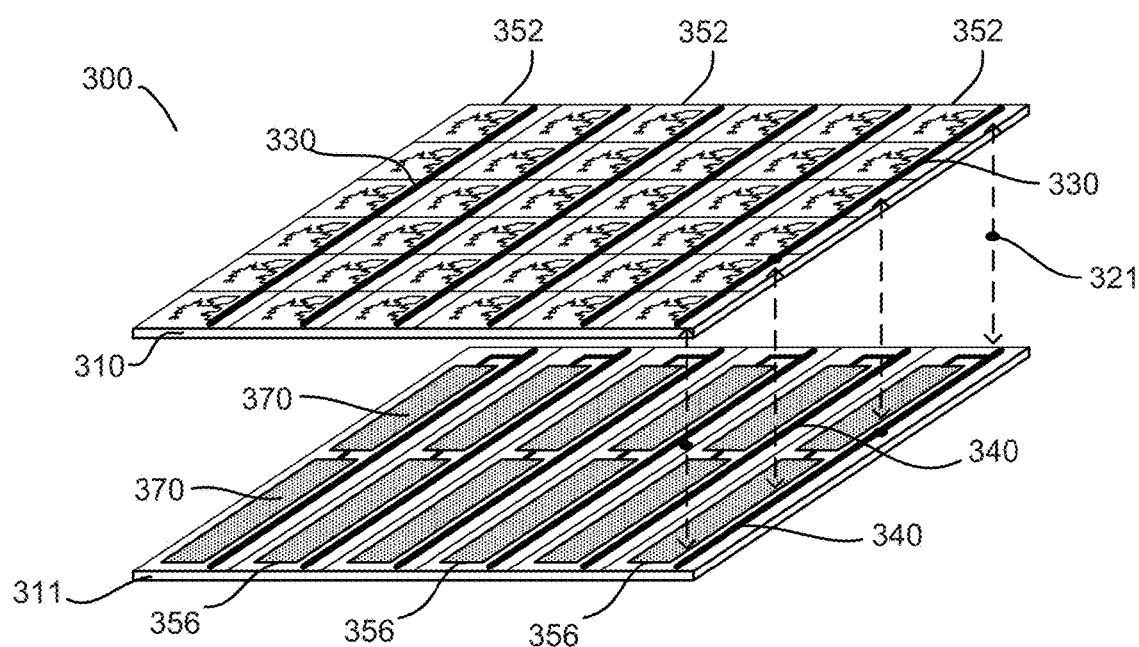
FIG. 3i illustrates a perspective view of an embodiment of an imaging sensor built on a plurality of substrates wherein a plurality of pixel columns forming the pixel array are located on the first substrate and a plurality of circuit columns are located on a second substrate and showing an electrical connection and communication between one column of pixels to its associated or corresponding column of circuitry.
Figure 3J:
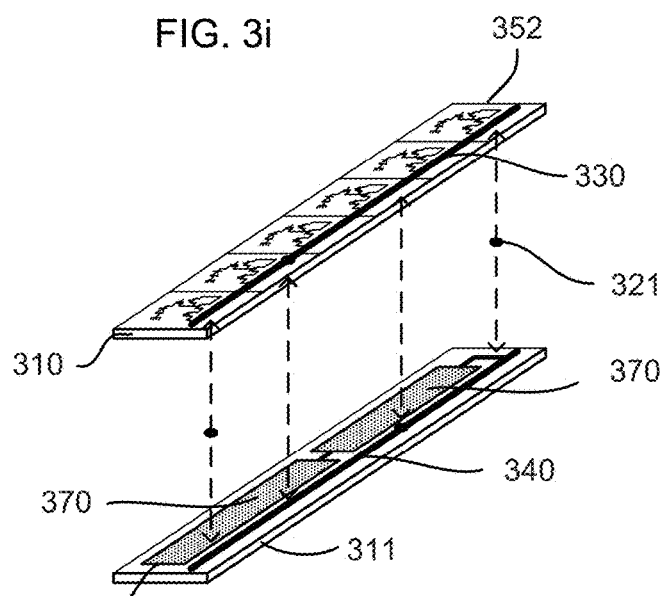
FIG. 3j illustrates a perspective view of a single column of pixels and a single column of circuitry taken from FIG. 3i showing an electrical connection therebetween.
Figures 3K, 3L:
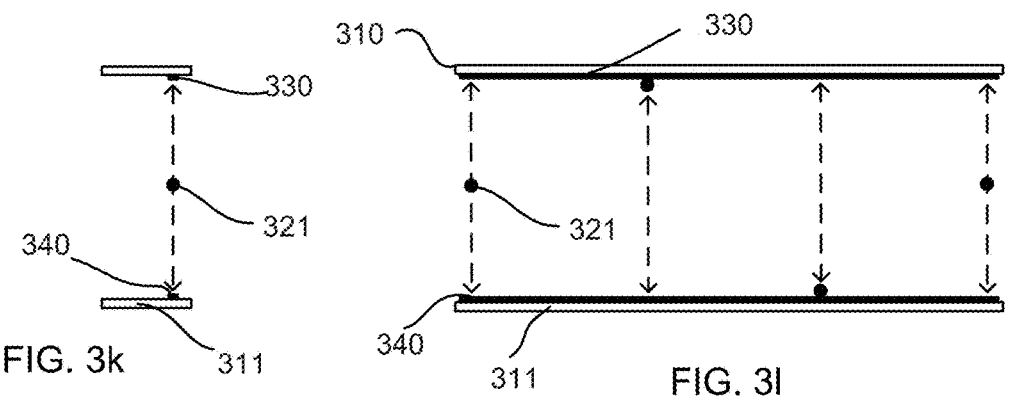
FIG. 3k illustrates a front view of the single column of pixels and the single column of circuitry taken from FIGS. 3i and 3j showing an electrical connection therebetween.
FIG. 3l illustrates a side view of the single column of pixels and the single column of circuitry taken from FIGS. 3i and 3j showing an electrical connection therebetween.
Figure 3M:
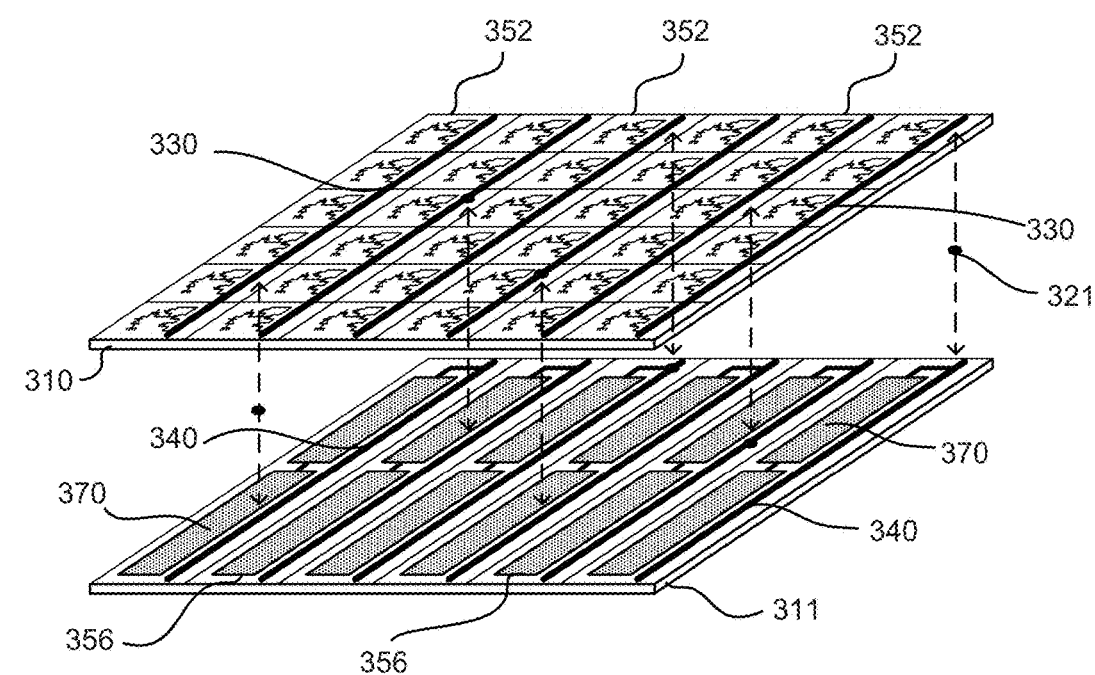
FIG. 3m illustrates a perspective view of an embodiment of an imaging sensor built on a plurality of substrates wherein a plurality of pixel columns forming the pixel array are located on the first substrate and a plurality of circuit columns are located on a second substrate and showing a plurality of electrical connections and communication between the plurality of pixel columns and associated or corresponding columns of circuitry.

Referring now to FIGS. 3i through 3m, there is illustrated various views of an embodiment of an imaging sensor 300 built on a plurality of substrates. FIGS. 3i and 3m illustrate a plurality of pixel columns 352 forming the pixel array 350 on the first substrate 310 and a plurality of circuit columns 356 (that represent the supporting circuitry 370) on the second substrate 311. As illustrated, the circuit columns 356 may be one pixel in width and AN@ number of pixels long to correspond directly with the pixel column 352 to which the circuit column 356 is associated. The figures show an example of a connection between each pixel column 352 to its associated circuitry 370 in a circuit column 356. The figures also show one read bus 330 per pixel column 352 and one read bus 340 per circuit column 356, where the associated circuitry 370 in a circuit column 356 is one pixel column wide.

As noted herein above, each pixel column 352 may be electrically associated or connected to one pixel column bus 330, and each circuit column 356 may be electrically associated or connected to one circuit column bus 340. FIGS. 3j through 3l illustrate a perspective view, a front view and a side view, respectively, of a single pixel column 352 and a single circuit column 356 separated from the plurality of pixel columns 352 and plurality of circuit columns 356 illustrated in FIG. 3i. FIGS. 3j through 3l further illustrate the electrical connection between the buses 330 and 340 of the pixel column 352 and the circuit column 356 using one or more interconnects 321. While the buses 330 and 340 may be electrically connected using one or more interconnects 321, the figures illustrate that the interconnect 321 may be located anywhere along the superimposed path of the buses 330 and 340 without departing from the spirit or scope of the disclosure.

Referring now to FIG. 3n through 3t, there is illustrated various views of an embodiment of an imaging sensor 300 built on a plurality of substrates, wherein a plurality of pixel columns 352 forming the pixel array 350 are located on the first substrate 310 and a plurality of circuit columns 356 are located on a second substrate 311. In this embodiment, the circuit columns 356 may be two pixels or two pixel columns in width. In this example, the connection between each pixel column 352 to its associated circuitry 370 in a corresponding circuit column 356 may be one read bus 330, 340 per pixel column 352 and circuit column 356. As can be seen in the figure, the area consumed by the pixel column 352 on the first substrate 310 corresponds to an area consumed by a corresponding circuit column 356. Such correspondence allows for direct overlay of the substrates, for example 310 and 311, such that support circuits 370 in a circuit column 356 are directly stacked with the pixel column 352 they support.

It should also be noted that in such a configuration, the aspect ratio of the pixel column 352 will be substantially equal to the aspect ratio of the circuit column 356, however such aspect ratio equality is not required as discussed further below. As can be seen in FIG. 3m the pixel column is one pixel column wide and six pixels long, so the aspect ratio is 1/6. The circuit column also has the same aspect ratio of 1/6. In contrast, FIG. 3n illustrates a design wherein the circuit column aspect ratio is twice as wide as the pixel column aspect ratio, but is only half as long, thereby providing a possibly more usable footprint in which to place supporting circuits. In both FIGS. 3m and 3n, the area of the footprint of both the pixel column 352 and the circuit column 356 is substantially equal to each other even though the aspect ratios are different.

FIG. 3n also illustrates how differing aspect ratios between the substrates can allow for flexibility in bus contact points. In the embodiment, the column circuit bus 340 has been designed with a general Au@ shape that so as to occupy the area of the circuit column 356 more evenly, thereby providing options for connecting the interconnect 321 throughout the entire circuit column 356. Note that the pixel column bus 330 is not generally u-shaped, but the circuit column bus 340 may be generally u-shaped, so that the same column circuit 356 may be used with the two different pixel column configurations of FIGS. 3o and 3r. The first leg of the u-shaped circuit column bus 340 may be superimposed to the read bus 330 of the first pixel column 352 (as illustrated in FIG. 3o) and the second leg of the u-shaped circuit column bus 340 may be superimposed to the read bus 330 of the next, adjacent pixel column 352 (as illustrated in FIG. 3r). FIG. 3o and FIG. 3r illustrate pixel columns 352 taken from the pixel array 350 of FIG. 3n. FIG. 3o and FIG. 3r illustrate three options for interconnect 321 positioning within the circuit column 356 footprint. In should be noted, as illustrated in FIG. 3q, that because the aspect ratio of the circuit column 356 is illustrated as being twice as wide, but one half the length of the corresponding pixel column 352, the interconnect 321 location options are only available for a portion of the pixel column 352 length. FIG. 3p illustrates that for a complex bus shape there may be two interconnect location path options along a bus 340 in a circuit column 356 having twice the width of the pixel column 352 it supports. FIG. 3p illustrates a front view of the superimposition of the first leg of the u-shaped circuit column bus 340 to the read bus 330 of the first pixel column 352 and uses the outer most portion of the bus 340 for locating the interconnect 321 as opposed to the innermost portion of the bus 340 as illustrated in FIGS. 3r and 3s for locating the interconnect 321 to the next, adjacent pixel column 352. FIG. 3r illustrates the next pixel column 352 located to the left of and relative to the first pixel column illustrated in FIGS. 3n (right most pixel column) and 3o. The bus 330 of the second pixel column 352 illustrated in FIG. 3r may be electrically connected to the second leg of the bus 340 as illustrated. It should be noted that because the footprint of the circuit column 356 has an aspect ratio of 2/3, the superimposition of the pixel column bus 330 to the circuit column bus 340 requires the second leg of the circuit column bus 340 to be generally u-shaped to thereby allow a natural match or superimposition of the buses 330 and 340 with respect to the next pixel column 352 illustrated in FIGS. 3r and 3s.

FIG. 3u illustrates a perspective view of an embodiment of an imaging sensor 300 built on a plurality of substrates wherein a plurality of pixel columns 352 forming the pixel array 350 are located on the first substrate 310 and a plurality of circuit columns 356 are located on a second substrate 311, wherein the circuit columns 356 are four pixels in width, but are also one fourth the length. The figure also illustrates a plurality of electrical connections and communication paths between the plurality of pixel columns 352 and associated or corresponding columns 356 of circuitry.

FIG. 3v illustrates a perspective view of a single column of pixels 352 and a single column of circuitry 356 taken from the right most column of FIG. 3u showing an electrical connection therebetween and an illustrative bus configuration to accommodate the architecture. As can be seen in the figure, an embodiment may comprise a pixel column 352 (and associated bus 330) that has a minimal portion of overlay with a corresponding circuit column 356 (and associated bus 340). In other words, very little bus superimposition is required between substrates. However, as illustrated in FIG. 3u, there may be superimposition on the substrate level.

FIG. 3w illustrates a front view of the single column of pixels 352 and the single column of circuitry 356 taken from FIG. 3v showing an electrical connection therebetween. As can be seen in the figure, only a small lateral portion of bus superimposition is needed to connect the pixel column 352 to the circuit column 356.

FIG. 3x illustrates a side view of the single column of pixels 352 and the single column of circuitry 356 taken from FIG. 3v showing an electrical connection therebetween. As can be seen in the figure, one or more interconnects 321 can be used in some embodiments and the figure also illustrates that the placement of the interconnects 321 may be anywhere along the superimposition of the buses 330 and 340.

FIG. 3y illustrates a perspective view of a single column of pixels 352 and a single column of circuitry 356 taken from the column to the left of, and adjacent to, the right most column 356 of FIG. 3u showing an electrical connection therebetween. FIG. 3z illustrates a front view of the single column of pixels 352 and the single column of circuitry 356 taken from FIG. 3y showing an electrical connection therebetween. FIG. 3v and FIG. 3y illustrate pixel columns 352 taken from the pixel array 350 of FIG. 3u. FIG. 3v and FIG. 3y illustrate two options for interconnect 321 positioning within the circuit column 356 footprint. It should be noted, as illustrated in FIG. 3aa, that because the aspect ratio of the circuit column is wider, but shorter than that of the corresponding pixel column 352, the interconnect location options are only available for a portion of the pixel column 352 length. FIG. 3z illustrates that for a complex bus shape there may be four interconnect location path options along a bus 340 in a circuit column 356 having four times the width and one fourth the length of the pixel column 352 it supports. Thus, it can be seen that while the aspect ratio of the circuit column 356 is different than the aspect ratio of the pixel column 352, the areas of the respective footprints are substantially the same or equal. As manufacturing techniques improve or design parameters change more or less area may be needed for the supporting circuits of the circuit column 356.

FIGS. 3v and 3w illustrate the superimposition of the first pixel column read bus 330 with the first leg of the circuit column read bus 340. FIG. 3y illustrates the next, adjacent pixel column relative to the pixel column illustrated in FIG. 3v. It should be noted that because the footprint of the circuit column 356 has an aspect ratio of 4/2, the superimposition of the pixel column bus 330 to the circuit column bus 340 requires the second leg of the circuit column bus 340 to be shaped accordingly to thereby allow a natural match or superimposition of the buses 330 and 340 with respect to the next pixel column 352 illustrated in FIGS. 3y and 3z FIG. 3aa illustrates a side view of the single column of pixels and the single column of circuitry taken from FIG. 3y showing an electrical connection therebetween.

Figure 12:
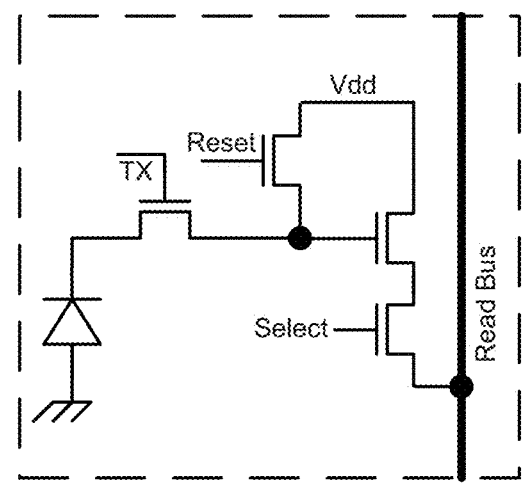
FIG. 12 illustrates an embodiment of pixel architecture, where each pixel column does not share a read bus with another pixel column.
Figure 13:
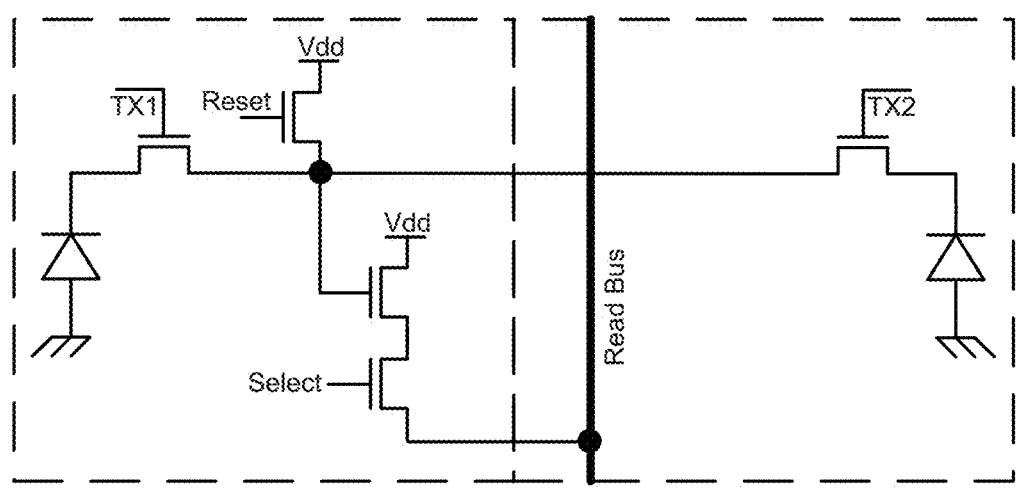
FIG. 13 illustrates an embodiment of pixel architecture, where there is a horizontal 2-way share of pixel columns with respect to a read bus, such that there is one read bus per two pixel columns.

It will be appreciated that each of the pixel columns may be shared or unshared with respect to a read bus, depending upon the conditions present that may affect pixel design and architecture. Illustrated in FIGS. 12 and 13 are two examples of pixel architecture. FIG. 12 illustrates a pixel architecture where each pixel column does not share a read bus with another pixel column. This example, when there is only one read bus per pixel column, illustrates an unshared pixel architecture. Conversely, illustrated in FIG. 13 is a horizontal 2-way pixel share. In FIG. 13, there is only one read bus per two pixel columns. Note that the number of read buses per pixel column may be an important consideration in embodiments where the pixel array 350 is optimized on a first substrate and separated from the majority of the supporting circuitry located on a second or supporting substrate in a three dimensional stacking embodiment as discussed herein.

It should be noted that it is within the scope of the disclosure to allow for a plurality of pixel columns to correspond to a set of support circuits in a circuit column. For example, because the processing power of some support circuits may be greater than what is required by the data generated by a pixel column, a plurality of pixel columns may correspond to a circuit column. The converse is also contemplated herein, wherein certain embodiments a plurality of circuit columns may correspond to a single pixel column in a pixel array.

In an embodiment of the specific process and implementation described above, the connection may be done though an interconnect, such as a ubump, located between the two substrates/chips. Both metal layers of the two substrates/chips may face each other, therefore back side illumination may be needed on the CMOS image sensor chip comprising the pixel array (front-side of the first chip may be bonded to front-side of the second chip). In an embodiment, there may be only one interconnect used per column 352, 356 between the first substrate/chip and the second substrate/chip. In an embodiment, two or more interconnects may be used per column 352, 356 and may be used for redundancy purposes (process yield). Compared to conventional technology (monolithic CMOS image sensor as shown in FIGS. 3a through 3f), the read bus may be broken at the edge of the pixel array and may be replicated in the second substrate/chip. A bump may then connect the two buses anywhere within the column. It will be appreciated that more interconnects, such as ubumps, may be needed for power distribution between the two or more substrates/chips or for other signals (e.g., vertical decoder).

Figure 9:
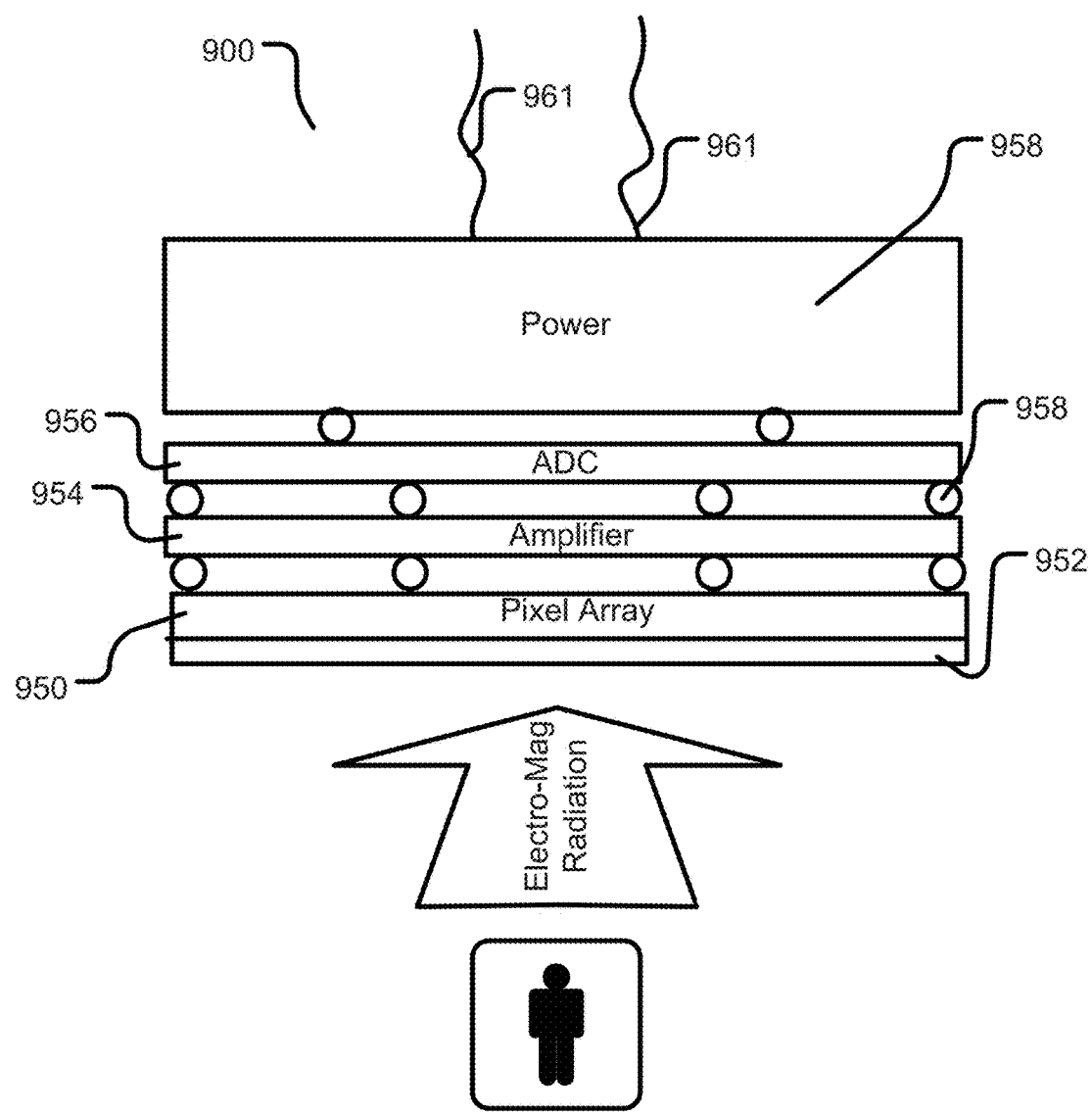
FIG. 9 illustrates a backside illuminated embodiment of an image sensor with an optimized pixel array and related or supporting circuitry being stacked in accordance with the teachings and principles of the disclosure.

Referring now to FIG. 4, an embodiment of an image sensor with its pixel array and supporting circuitry built on a plurality of substrates is illustrated using backside illumination. As can be seen in the figure, a pixel array 450 may be disposed on a first substrate 452. The first substrate 452 may be made of silicon or of another material in order to control light transmission characteristics. Solder balls, bumps or vias 421 may be used to electrically connect one substrate to another. An embodiment of a stacked image sensor may comprise a pixel array 450 on a first substrate 452. The pixel array 450 may cover at least forty percent of a first surface 451 of the first substrate 452. In a backside illuminated configuration, a pixel array 950 may be disposed on the backside of said first substrate 952 as illustrated best in FIG. 9. Further, in a back side illumination configuration the substrate 452 may be thinned for controlling light transmission therethough. In an embodiment utilizing backside illumination, the first substrate may be made of primarily silicon material, or the first substrate may be made of primarily of AHigh-Z@ semiconductor material (Cadmium Telluride e.g.), or the first substrate may be made primarily of III-V semiconductor materials (Gallium Arsenide e.g.).

In an embodiment, a pixel array 450 may cover a majority of the first surface 451 of a first substrate 452. In such an embodiment the pixel array 450 may be situated or located on any portion of said first surface 451. The remaining space on the first surface 451 may be used for secondary circuit placement if desired. Situations may arise where a secondary circuit may be sized such that central placement of the pixel array is not practical.

Figure 5:
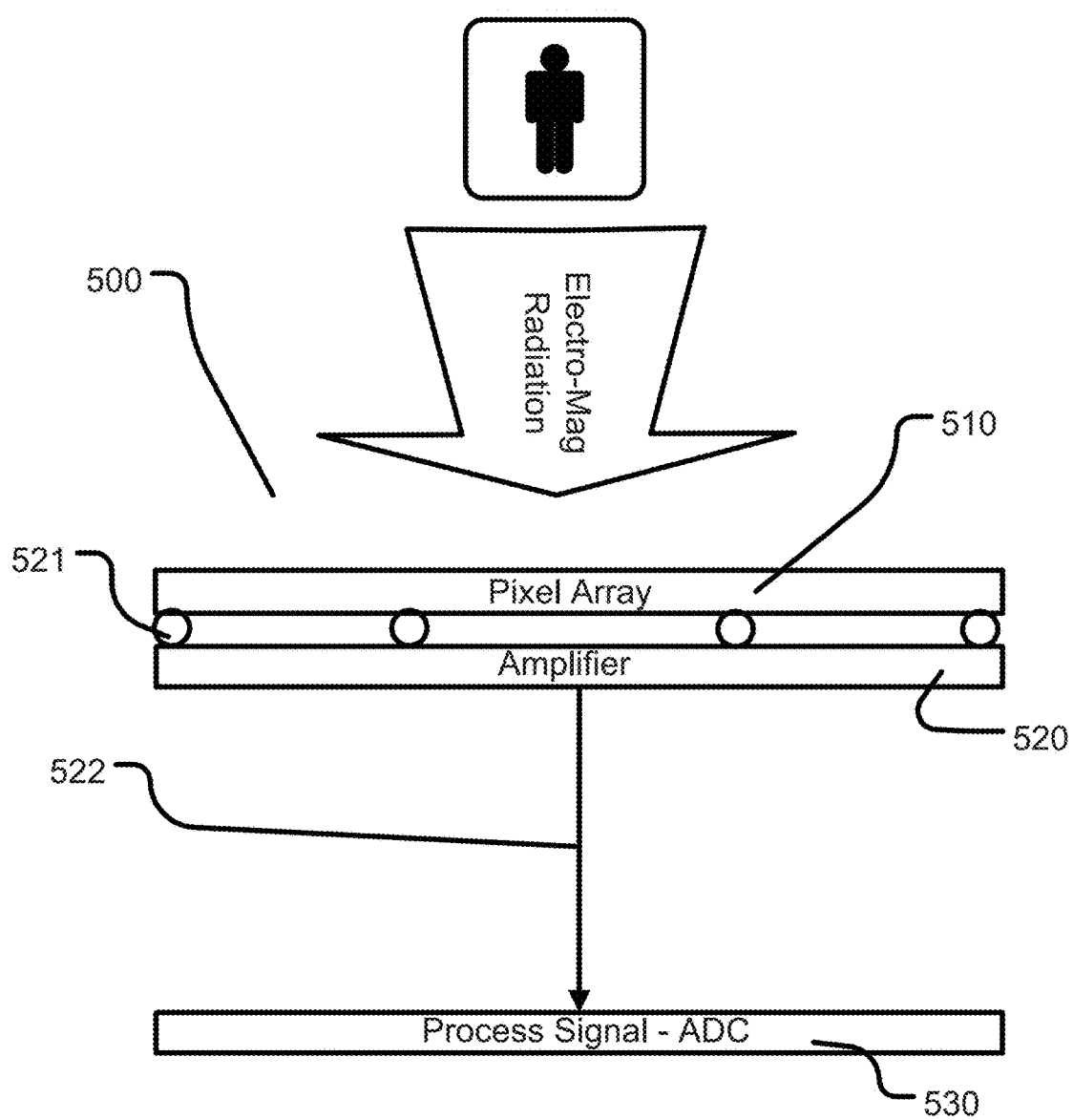
FIG. 5 illustrates an embodiment of an imaging sensor built on a plurality of substrates and also illustrating an embodiment of the specific placement of support circuits wherein some of the circuits are relatively remotely placed in accordance with the teachings and principles of the disclosure.

Referring now to FIG. 5, an embodiment will be discussed wherein at least some of the supporting circuitry and components are remotely located from other supporting circuitry and components in order to work for a predetermined purpose. For some applications, it may be desirous for certain secondary processors to be more remotely located from the pixel array. For example, in a medical scope such as an endoscope there may not be enough room around the pixel array to contain all of the needed support circuitry. In such cases, the pixel array containing substrate 510 may be remotely located a distance away from other supporting substrates within the image sensor 500.

In an embodiment, the pixel array containing substrate 510 may be adjacent to or near a support substrate 520 that is located remotely with respect to the pixel array containing substrate. The support substrate 520 may comprise an amplifier circuit thereon, while other supporting circuits may be more remotely located on another substrate 530 a distance that is farther away from the pixel array substrate 510 than the distance support substrate 520 is located away from the pixel array substrate 510. In an embodiment the more remotely located substrate 530 may be connected to the other substrates in the image sensor 500 by wire vias 522 or may communicate wirelessly with the other substrates and circuits. Adjacent substrates may be connected to each other by way of bumps or solder balls 521. As pixel arrays and other circuits become more efficient over time, it is within the scope of this disclosure to provide an image sensor wherein the pixel array containing substrate is more remote from all other support circuits. Such a circuit is pictured in FIG. 10, wherein a pixel array containing substrate 1010 is more remotely located by way of vias 1022 from support substrates 1020, 1030, 1040 each comprising support circuits such as signal processing circuits and power circuits.

Figure 6:
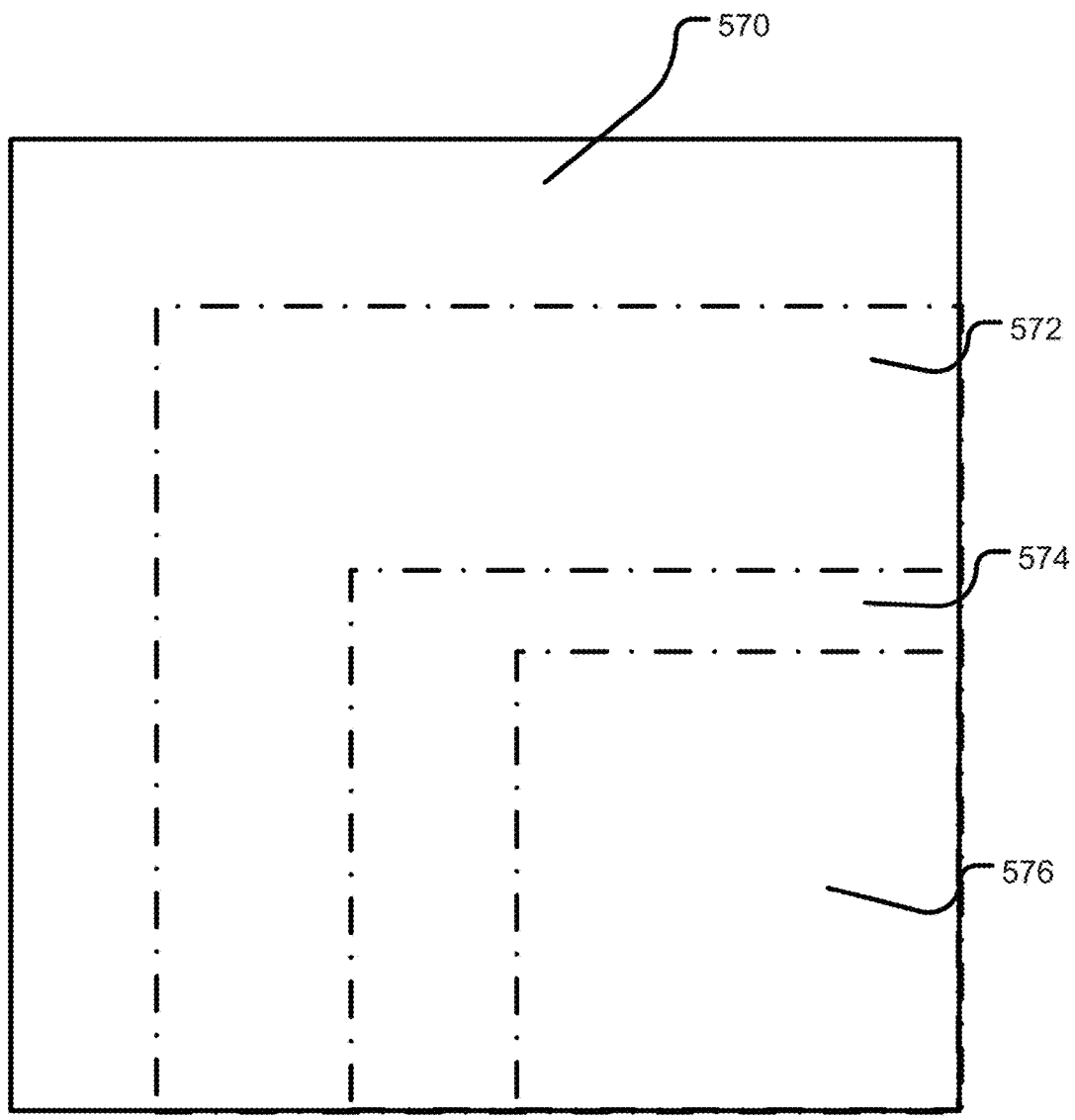
FIG. 6 illustrates an embodiment of a first substrate having various percentages of coverage by differing pixel arrays in accordance with the teachings and principles of the disclosure.

In an embodiment, the pixel array of an image sensor may dominate a large percentage of the available surface area of a first substrate 570. As can be seen in FIG. 6, various sized pixel arrays 572, 574, 576 (shown in dashed lines) are contemplated by the disclosure and fall within the scope of the design disclosed. Pixel array 576 schematically represents a configuration wherein the pixel array 576 covers a large percentage of a first substrate 570, but yet may not cover a majority of the substrate 570. Pixel array 576 may cover such a large percentage of the available area, even though not a majority of the area, such that at least some of the supporting circuitry may not be located on the first substrate 570.

Pixel array 574 schematically illustrates a separate configuration from pixel array 576 and 572, wherein the pixel array 574 covers approximately half of a first substrate 570. Pixel array 572 schematically illustrates a separate configuration from pixel array 576 and 574, wherein the pixel array covers a clear majority of the first substrate 570. It should be apparent from the discussion above that the optimization process may allow for finding a pixel array size that provides the best possible image and image quality while working within constraints dictated by an application, function or purpose. Accordingly, even in an application having an imaging sensor with a fixed first substrate size, the percentage of the surface area occupied by the pixel array located on the first substrate may differ and cover many different percentages of the total surface area available on the first substrate.

Thus, it will be appreciated that the surface area that the pixel array may occupy may fall within a range that is about 25% to about 99% of the total surface area of one of the surfaces of the first substrate, or may be within a range of about 40% to about 99% of the total surface area of one of the surfaces of the first substrate, or may be within a range of about 50% to about 99% of the total surface area of one of the surfaces of the first substrate, or may be within a range of about 60% to about 99% of the total surface area of one of the surfaces of the first substrate, or may be within a range of about 70% to about 99% of the total surface area of one of the surfaces of the first substrate, or may be within a range of about 80% to about 99% of the total surface area of one of the surfaces of the first substrate, or may be within a range of about 90% to about 99% of the total surface area of one of the surfaces of the first substrate. It will be appreciated that all percentages that fall within the stated ranges are intended to fall within the scope of the disclosure. It will further be appreciated that all sub-ranges falling within the range of about 25% to about 99% of the total surface area of one of the surfaces of the first substrate are intended to fall within the scope of the disclosure.

Because of the nature of a backside illuminated pixel array, the substrate surfaces discussed above may be extraneous to an image sensor comprising a backside illuminated pixel array. Thus, in backside illuminated applications, the substrate surface may be eliminated or formed integrally with the pixel array.

Pixel array coverage or surface area may be within a range of about 40% to about 70% of the total surface area of the substrate upon which the pixel array resides, and in such cases it may be possible to place some support circuitry thereon without diminishing from the design of the image sensor. In an embodiment, a light emitting circuit may occupy some space on the first substrate to provide light during use. For many applications, where dimensions are extremely tight and are the most tightly constrained, an optimized imaging sensor may cover 90% or more, up to substantially all of a surface area of a first substrate. It should be noted that it is within the scope of this disclosure to contemplate a pixel array having an integrated substrate therein rather than being added to a substrate.

Figure 7:
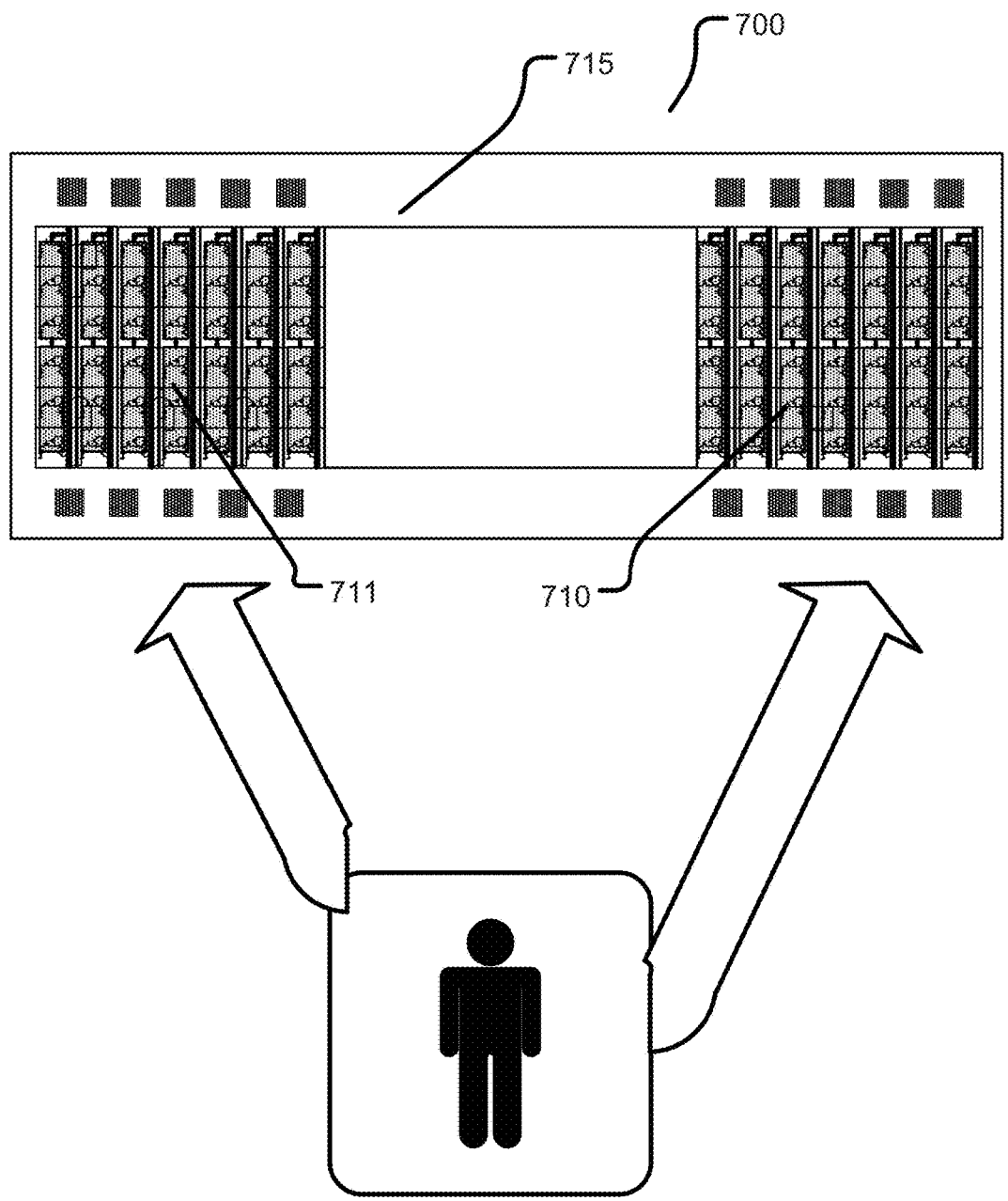
FIG. 7 illustrates an embodiment having a plurality of pixel arrays in accordance with the teachings and principles of the disclosure.
Figure 8:
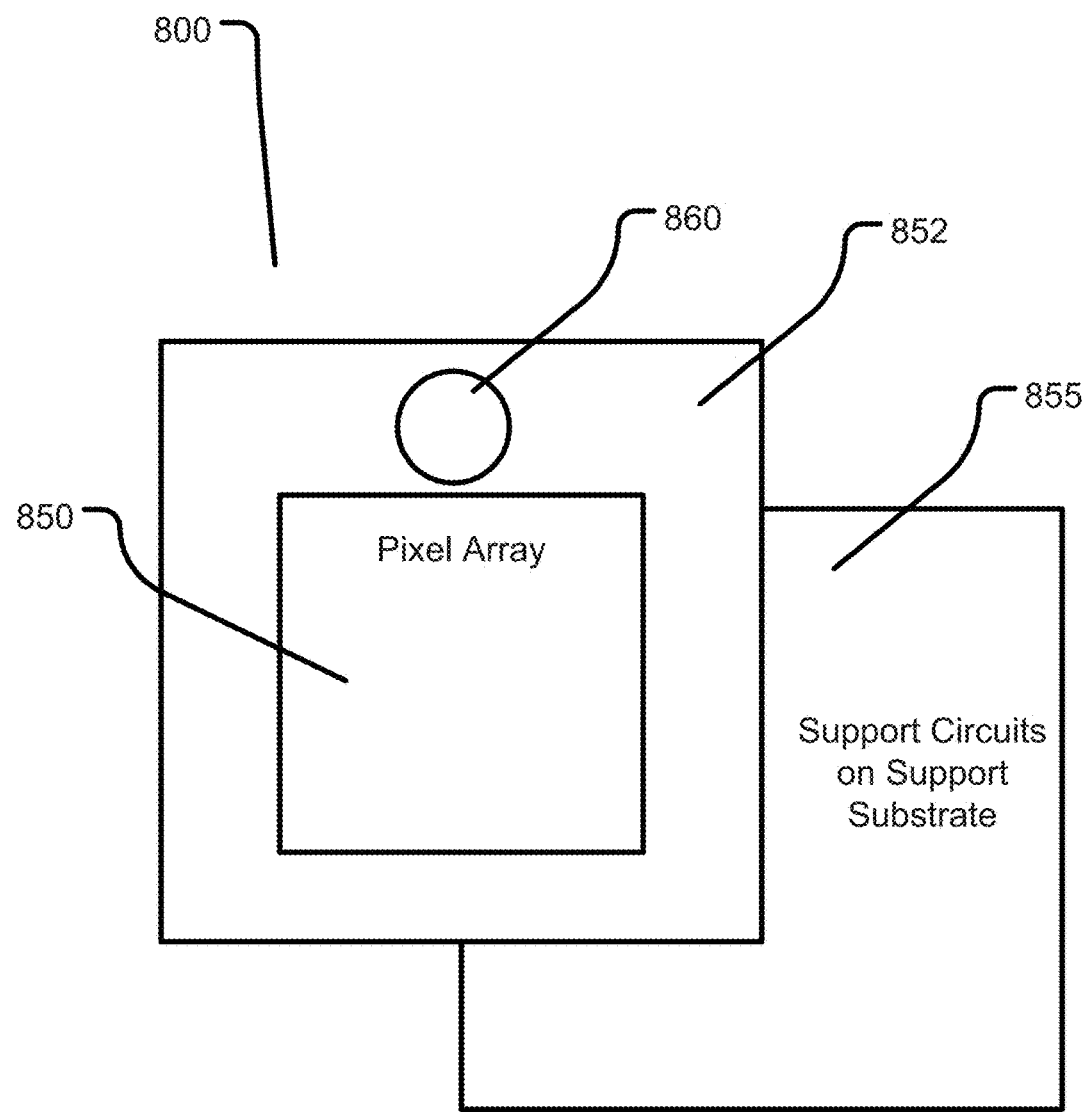
FIG. 8 illustrates an embodiment of an image sensor with an optimized pixel array and related or supporting circuitry being stacked and illustrating a light source in accordance with the teachings and principles of the disclosure.

Illustrated in FIG. 7 is an embodiment of an imaging sensor having a plurality of pixel arrays. As can be seen in the figure, an image sensor 700 may comprise a first image sensor 710 and a second image sensor 711, which are in electrical communication with a substrate 715 or a plurality of substrates that may be stacked vertically or otherwise with respect to an object to be imaged. In an embodiment, supporting circuits may be remotely located on subsequent or supporting substrates as discussed above. Such a configuration may be desirable for three dimensional image capture, wherein the two pixel arrays may be off set during use. In another embodiment, a first pixel array and a second pixel array may be dedicated to receiving a predetermined range of wave lengths of electromagnetic radiation, wherein the first pixel array is dedicated to a different range of wave length electromagnetic radiation than the second pixel array.

Illustrated in FIGS. 14 and 15 is an embodiment for retrieving data from a pixel array 1510 that has been optimized on a first substrate 1552 (see FIG. 15) with supporting circuitry 1520 for an image sensor 1500 located on one or more second, or supporting, substrates 1554 (see FIG. 14), which may be configured in a stacked configuration (FIGS. 14 and 15 combined). As can be seen in the figures, a pixel array 1510 may be located on the first substrate 1552 and may be electrically connected to support circuits 1520 that may reside on one or more subsequent or supporting substrates 1554 (FIG. 14) with one or more interconnects 1521. In the embodiment illustrated in FIGS. 14 and 15, the pixel array 1510 may be comprised of a plurality of pixel columns 1550a-f. Each of the pixel columns 1550a-f may be comprised of a plurality of individual pixels and the pixel columns 1550a-f may be read through corresponding pixel column buses 1551. It will be appreciated that there may be one read bus 1551 per pixel column 1550 within the entire pixel array 1510. It should be noted that the plurality of individual pixels 1526 may be formed in columns (y axis) and rows (x-axis) that denote or define the position of the individual pixel 1526 within the pixel array 1510.

As illustrated in the figures, each of the plurality of pixel column read buses 1551 may provide an electrical connection for a predetermined or defined pixel column 1550, such as 1550a, 1550b, 1550c, 1550d, 1550e, and 1550f in FIG. 15. In such an embodiment, data collected from the pixels 1526 within the predetermined or defined pixel column, for example 1550a, may be transmitted to support circuits 1520 located on one or more second, subsequent or supporting substrates 1554 via the circuit column read bus 1516 (see FIG. 14) and/or through one or more interconnects 1521. Circuits 1520 may be located on either side of the support substrate 1554 and electrical contact may be facilitated through vias disposed in the substrate material and running through the substrate. The subsequent substrate 1554 may comprise a plurality of circuit columns, each circuit column comprising a plurality of circuits 1520 and a bus 1516 for electrically connecting the various circuits 1520 within the circuit column within the image sensor 1500. It should be noted that the spacing between interconnects 1521, which may be used to connect the pixel column buses 1551 to the circuit column buses 1516, has been increased in the figure by staggering the interconnects 1521 relative to the pixel columns 1550a-f. The dashed lines illustrated on substrate 1554 illustrate an area on the substrate that corresponds to the area consumed by the pixel column 1550 on the first substrate 1552.

In an embodiment, it may be desirable to design an image sensor 1500 where support circuits 1520 for any given pixel column 1550 are placed within a corresponding area located on a second substrate. It should be noted that in an embodiment, one or more dedicated support circuits 1520 may be used per pixel column or area 1550, such that each pixel area 1550a-1550f has at least one support circuit 1520 dedicated to processing only the data produced by the pixels 1526 within that predetermined or defined pixel column represented by pixel columns 1550a-1550f to which the support circuit is dedicated. For example, each pixel column area 1550a-1550f may have a dedicated analog-to-digital conversion circuit dedicated to converting the analog data read from the associated pixels 1526 from within the associated pixel column 1550. This close and direct association of dedicated circuits can be used to simplify the digital signal processing within the image sensor 1500 thereby greatly simplifying the timing and serializing processes within the image sensor 1500. Such a feature can also be used to control heat production and energy consumption within the image sensor 1500.

Figure 16:
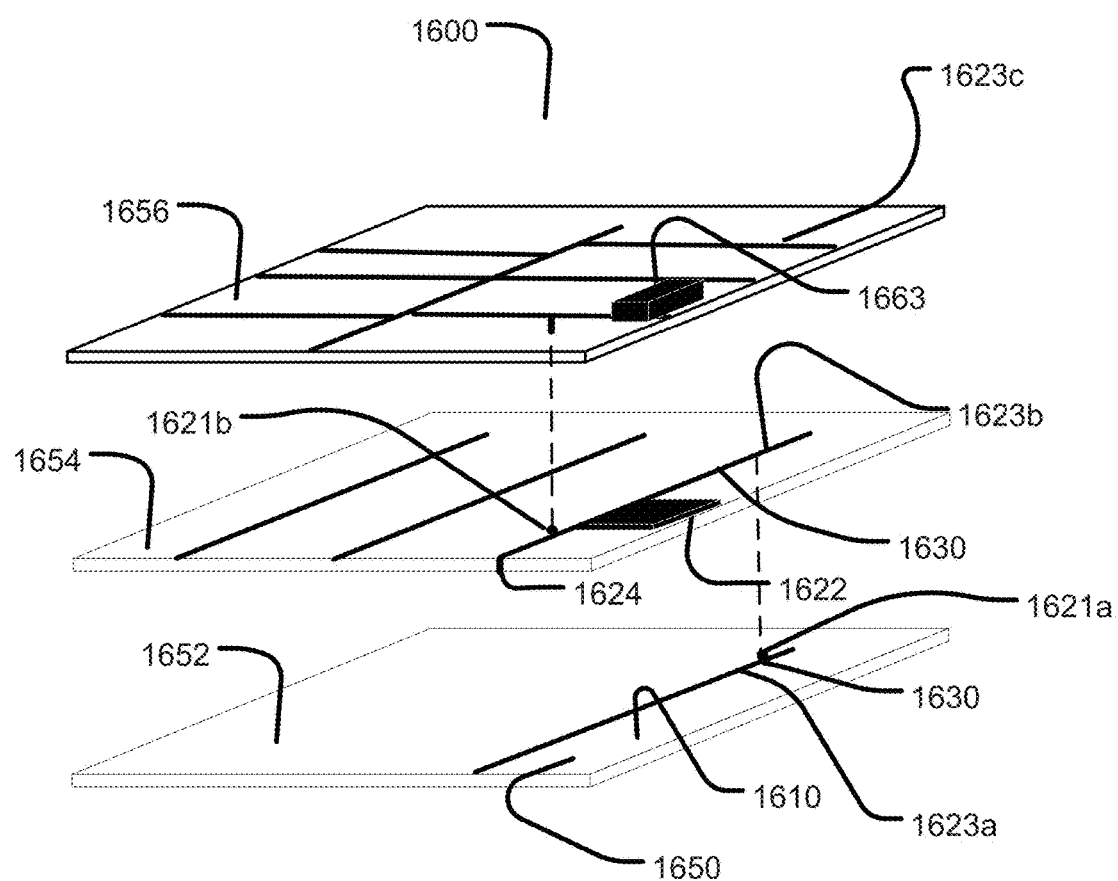
FIG. 16 illustrates an embodiment of an imaging sensor having a plurality of substrates and the connection of a plurality of buses for accessing data from a pixel array divided into read areas containing a plurality of pixels.

Referring primarily to FIG. 16, a multi-substrate image sensor 1600 having a read bus configuration therein is illustrated. As can be seen in the figure, a substrate 1652 may contain a pixel array 1610 and may be electrically connected to support substrates 1654 and 1656 through a plurality of pixel column read buses. Image sensor architecture can be greatly simplified by locating the support circuits on one or more subsequent substrates 1654 and 1656. The subsequent substrates 1654 and 1656 may be in close proximity to, but behind, the first substrate 1652. Support circuits 1622 and 1663 may be placed on the subsequent substrates 1654 and 1656 in order to allow for the stacking of the substrates in a vertical configuration as illustrated. Through substrate vias may be used to enable front to back communication through any of the substrates. The second substrate 1654 in the stack may comprise secondary circuits that are dedicated to pixel columns 1650 located on the first substrate 1652 and electrically connected therewith. The third substrate 1654 may comprise additional data processing circuits 1663 that may be dedicated to support circuits 1622 on the second substrate, and may be purposed to process data from a plurality of support circuits from the second substrate. It should be noted that circuits 1663 on the third substrate 1656 may be dedicated to a specific pixel column 1650 on the first substrate 1652, or may be dedicated to process data from a plurality of pixel columns 1650. In other words, circuits 1663 located on the third substrate 1656 may directly correspond to specific circuits 1622 on the second substrate 1654 or specific pixel columns 1650 on the first substrate 1652. It should be noted that each substrate may comprise at least one bus that electronically connects circuitry on all of the substrates. Accordingly, the buses 1623a-1623c of each of the substrates may be superimposed such that interconnects 1621 disposed between the substrates cause electrical connection between the buses 1623a-1623c.

As can be seen in the figure, a column of pixels 1650 located on the first substrate 1652 may be electrically connected to support circuits located on one or more supporting substrates 1654, 1656 through direct pixel column reading by placement of one or more strategically located interconnects 1621 within the pixel column 1650 or the bus system 1623a-1623c. Each of the plurality of substrates 1652, 1654, and 1656 that make up the image sensor 1600 may comprise its own bus or bus system 1623a, 1623b, and 1623c, respectively. Accordingly, it may be advantageous to connect each of the buses 1623 together to form a bus skeletal system 1630 from one layer of substrate to the next. For example, the first substrate 1652 comprising the optimized pixel array 1610 as disclosed herein may be connected to support circuits 1622, which reside on the second, subsequent substrate 1654 through the use of interconnects 1621 located within the predetermined or defined pixel column 1650 and interconnect 1621, which may be located anywhere along the path of the superimposed bus system 1623.

As illustrated, the first interconnect 1621a may be used to connect the first pixel column 1650 and pixel column bus 1623a directly to the second bus or bus system 1623b and support circuits 1622 located on the second substrate 1654, while the second interconnect 1621b may be used to connect the second bus or bus system 1623b residing on the second substrate 1654 to a third bus 1623c residing on the third substrate 1656. Additionally as illustrated in FIG. 16, the bus skeletal system 1630 may be extended beyond the first and second substrates 1652 and 1654 and may continue and electrically connect the second substrate 1654 to the third substrate 1656 and so on until all substrates have been electrically connected through the bus skeletal system 1630. The bus 1623b located on the second substrate 1654 may be connected to the third bus 1623c that may be located on the third substrate 1656 and so on until all substrates have been electrically connected together. Thus, the predetermined or defined pixel column 1650 may be in electrical communication with a support circuit 1622 that may reside remotely on the second substrate 1654 or a support circuit 1663 that may reside remotely on the third substrate 1656 through the respective buses 1623a-1623c located on the plurality of substrates.

It should be noted that because a single interconnect 1621 may be used to read a column 1650 containing a plurality of pixels, the interconnect spacing or pitch may be considerably larger than the pixel pitch of the pixel array 1610.

Figure 17A:
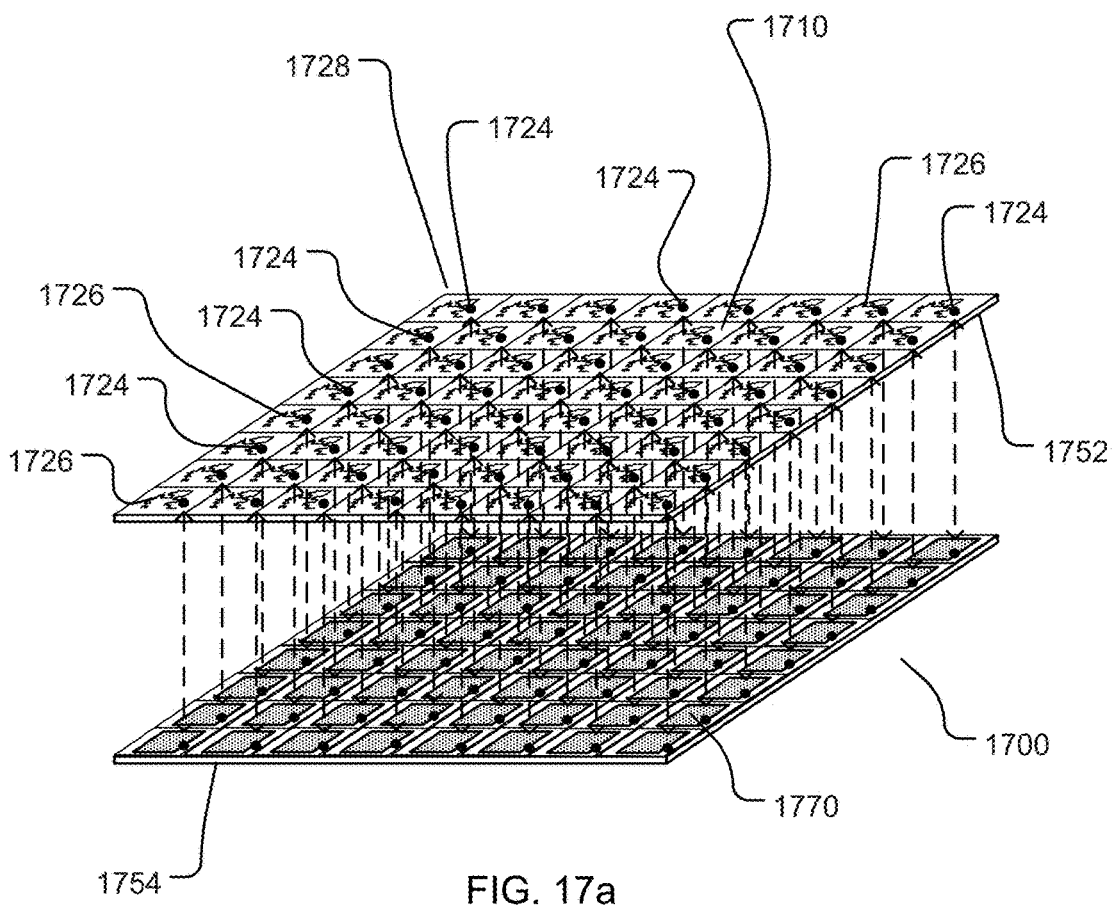
FIG. 17a illustrates an embodiment of a pixel array wherein interconnects are spaced relative to pixels within the pixel array in accordance with the teachings and principles of the disclosure.
Figure 17B:
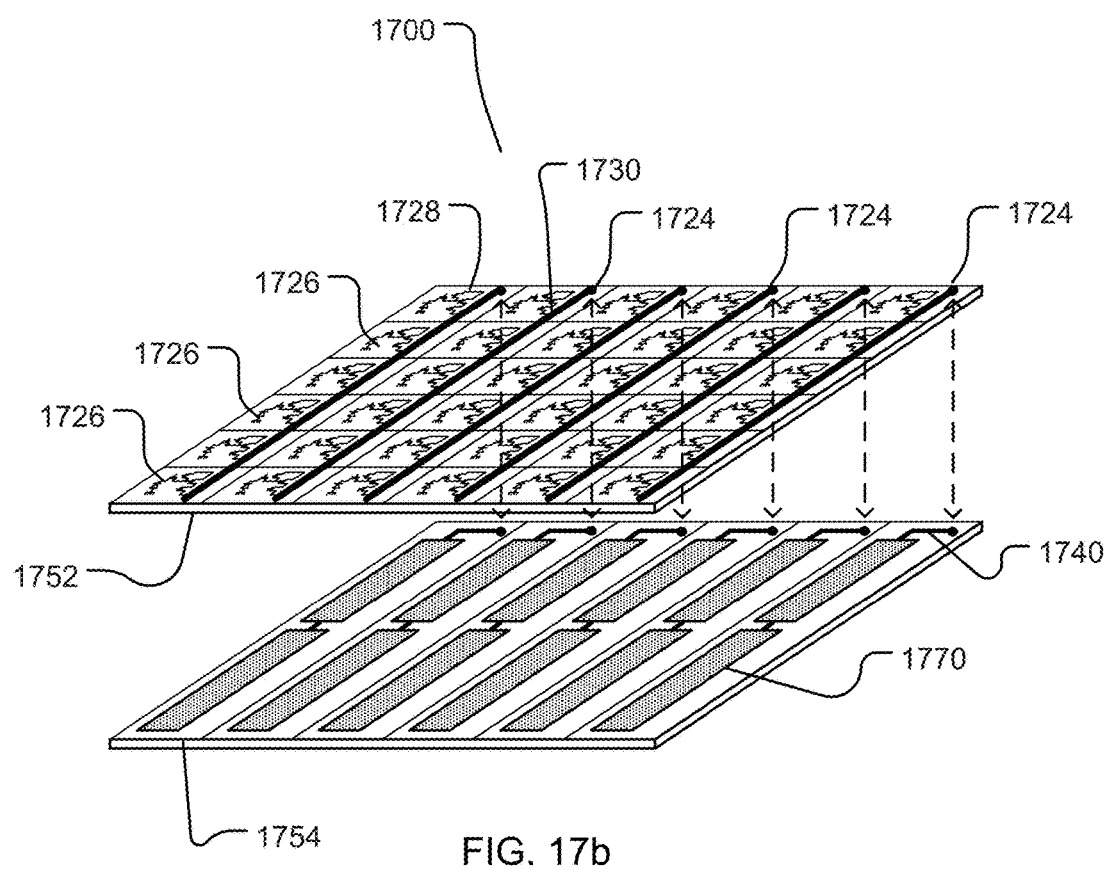
FIG. 17b illustrates an embodiment of a pixel array wherein interconnects are spaced relative to columns within the pixel array in accordance with the teachings and principles of the disclosure.

During use, data created by individual pixels on the pixel array must be processed by supporting circuitry, as such each pixel 1726 must be electronically connected to the supporting circuits 1770 on the second substrate 1754. Ideally each pixel could be read simultaneously thereby creating a global shutter. Referring now to FIG. 17a, it will be appreciated that the ability to read data from an imaging device as a global shutter requires that there be one interconnect 1724 per pixel 1726, which is very difficult to achieve in practice because of the bumping pitch in manufacturing tolerances. FIG. 17b illustrates a situation where the pixels 1726 have been formed in columns 1728, where the bump pitch requirements remain the same in the horizontal direction. A bump pitch of about 5 μm is required for pixels near that size, whereas utilizing three dimensional stacking technology and interconnect staggering disclosed herein may allow for a bump pitch of about 20 μm to about 200 μm in actual production. Therefore, a very high frame rate rolling type shutter that also uses the stacking technology in three dimensions may be considered a substantial improvement. In the case of a rolling shutter, only one interconnect/bump 1724 per pixel column 1728 is required instead of one interconnect/bump 1724 per pixel 1726.

FIG. 17a illustrates a bumping configuration or scheme using one bump 1724 per pixel 1726, which approximates a global shutter operation. In this configuration, the bump pitch equals or substantially equals the pixel pitch in both the X and Y axes or directions.

FIG. 17b illustrates a bumping configuration or scheme using one interconnect/bump 1724 per pixel column 1728. This configuration may be used in a rolling shutter operation. This bump pitch configuration or scheme is more relaxed as compared to the bump pitch of FIG. 17a in the vertical direction only. However, it should be noted that in this configuration the bump pitch is still required to be at least the same in one direction or dimension as the pixel pitch. FIG. 17b illustrates a plurality of columns 1728, where each column 1728 is comprised of a plurality of pixels 1726. Each column of pixels may run in the Y direction (y-axis) for a distance and may be one pixel in width as illustrated. Each column of pixels may be read through a single connection point at one end of each column 1728. Although such a configuration simplifies chip architecture, tight tolerances must still be maintained because the distance between pixels laterally (horizontally) continues to limit bump (interconnect) pitch because the interconnect must not make contact with a neighboring interconnect and must be sized accordingly.

Figure 17C:
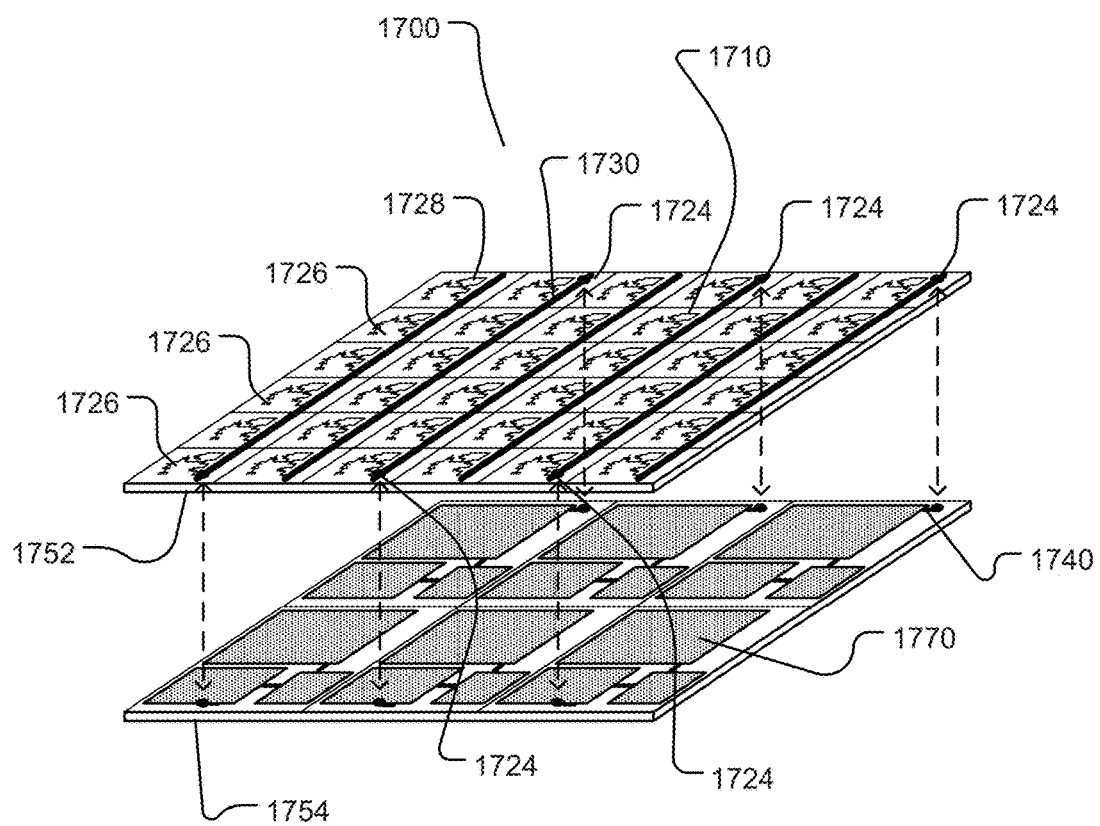
FIG. 17c illustrates an embodiment of a pixel array wherein a interconnects are spaced relative to areas within the pixel array in accordance with the teachings and principles of the disclosure.

FIG. 17c, illustrates a bumping configuration that is even further relaxed than that shown in FIG. 17a or 17b. In this figure, the bump pitch is relaxed and half of the interconnects/bumps 1724 can be processed at each side of the pixel array 1710 by adding or introducing a second set of interconnects 1724 at alternating and opposing ends of the columns 1728. As can be seen in FIG. 17c, the second set of interconnects may be used in combination with the first set of interconnects and may be employed to allow half of the data to be processed or read at each side of the pixel array 1710. Such a configuration may allow for nearly double the size of bump pitch (interconnect) as compared to the pixel pitch in at least one dimension, which would greatly decrease the cost of producing image sensors 1700. In an embodiment, more than one interconnect or bump 1724 per pixel column 1728 may be utilized, such that data may be read from either end of the pixel column 1728.

FIGS. 18a-18f illustrate embodiments and configurations of a pixel array 1810 having staggered interconnect or bump 1824 positioning on a substrate/chip. As noted above, because there is one read bus per pixel column 1828 and one read bus per circuit column, and because the read buses run from the top of the column to the bottom of the column, the interconnect/bump 1824 may be placed anywhere along the superimposed path of the buses within the column. In order to relax the bumping pitch, the bump distance may be increased from column to column by shifting the next column bump 1824 either up or down (in the Y direction) in the next column.

By way of example, it will be appreciated that pixel pitch may be about 5 μm and pixel column may be any length, for example between about 2 mm and about 15 mm long. It should be noted that bump pitch is a function of pixel pitch, such that the pixel pitch will be determinative of an ideal bump pitch. For example, assuming there is a desired bump pitch of approximately 100 μm, placing a first interconnect or bump 1824 may then be accomplished by starting at the top of the first column and shifting down the next column interconnect or bump by 100 μm. All other bumps are similarly positioned until the interconnect or bump in the 20th column of the line will be located at the bottom of the pixel column. At that point, the interconnect or bump in the 21st column may again be placed at the top of the pixel column. This same pattern may then be repeated until the end of the pixel array. Horizontally, the interconnects or bumps may be separated by 20 columns×5 μm=100 μm. In this example, all bumps will then be separated by more than 100 μm, even though the pixel pitch is about 5 μm. Redundancy can then be introduced in the pixel column for yield purposes. For example, bumps in all columns can be doubled (i.e., the two read buses are attached by 2 interconnects or bumps). This technique would significantly increase stacking yield and lower the cost of the overall process.

Figure 18A:
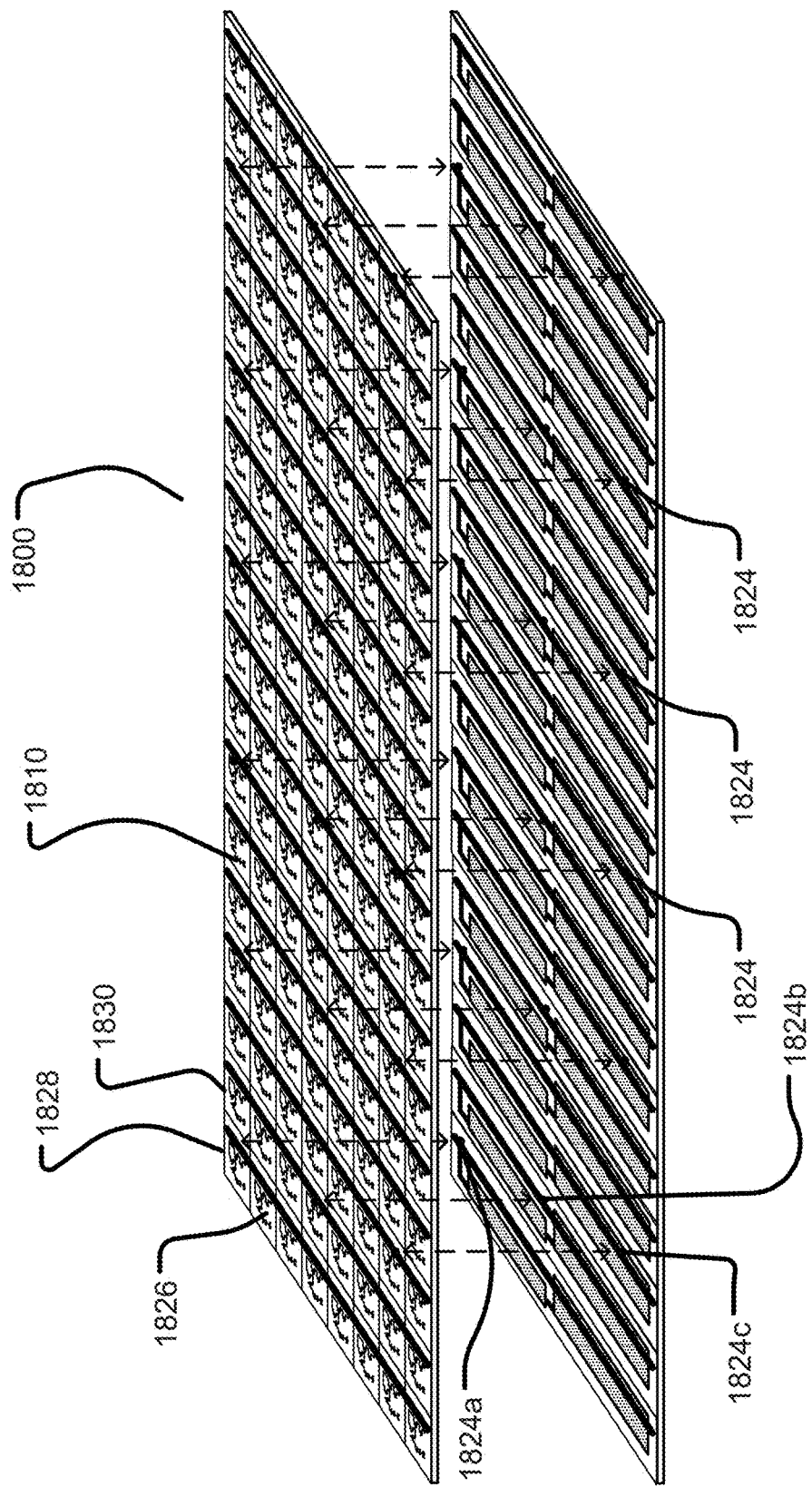
FIGS. 18a-18f illustrate embodiments of a pixel array, wherein interconnects may be spaced relative to defined pixel areas within the pixel array in accordance with the teachings and principles of the disclosure.

As can be seen in FIG. 18a, a first column 1828 of pixels 1826 may be electrically accessed via a first interconnect 1824a. In the embodiment, a second pixel column 1830 may be electrically accessed through a second interconnect 1824b, which has been positioned during manufacture in a staggered configuration relative to said first interconnect 1824a. As illustrated, the location or position of the second interconnect 1824b may be at least two pixel widths away from the position of the first interconnect 1824b (and from any other interconnect 1824) in both the X and Y dimensions or directions. A third interconnect 1824c may then be positioned in like manner in a third pixel column and so on for N-number of interconnects 1824 across the pixel array 1810. Such a configuration provides for an interconnect pitch that is at least three times that of the pixel pitch. It will be appreciated that the gain in interconnect pitch may be much greater than three times that of the pixel pitch under standard conditions. However, it will be appreciated that the gain in interconnect pitch may be at least three times the pixel pitch as noted above.

Likewise, greater interconnect gains may be made with area based spacing rather than column-by-column based connectivity (see figures and discussion relating to FIGS. 3m, 3n and 3u, which illustrate a pixel column aspect ratio of 6/1 and circuit column aspect ratio of 6/1 (for FIG. 3m) and 3/2 (for FIG. 3n), and a pixel column aspect ratio of 8/1 and circuit column aspect ratio of 2/4 (for FIG. 3u)). This can be accomplished with the addition of more bus structures or use of direct reading to a subsequent substrate. In either configuration, the interconnect pitch may be described thusly:

$$\text{Interconnect\_Pitch} = \sqrt{(N^*\text{PixelPitch}_x)^2 + (M^*\text{PixelPitch}_y)^2}$$

where N is the number of pixels between two adjacent interconnects in the X-direction and M is the number of pixels between two adjacent interconnects in the Y-direction. It will be appreciated that each of the plurality of interconnects may be a bump where the bump to bump distance may be greater than two pixels in width, or greater than four pixels in width, or greater than eight pixels in width.

Figure 18B:
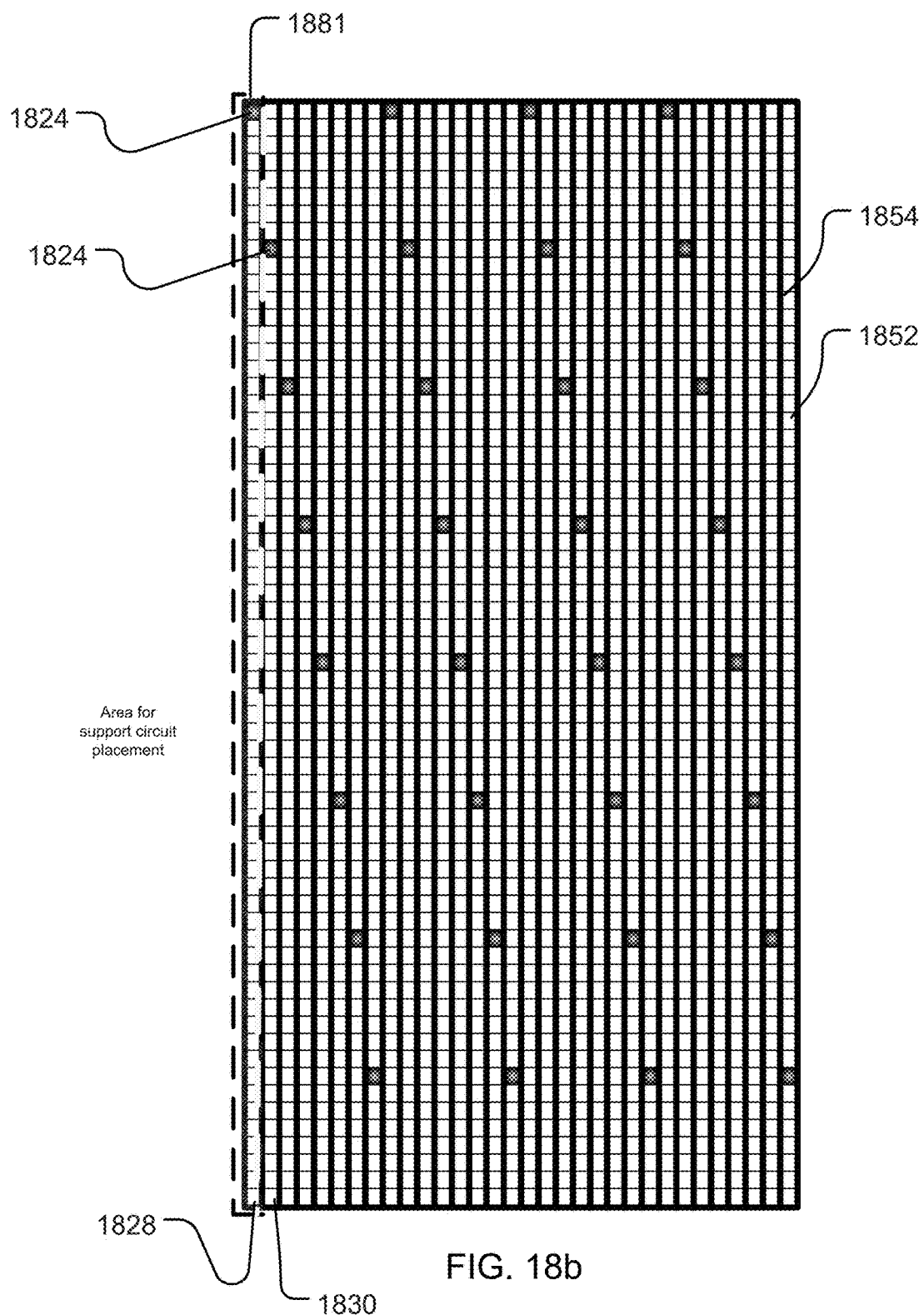

In many applications, the N×Pixel Pitch in the X direction will be equal to M×Pixel Pitch in the Y direction. As illustrated in FIGS. 18b-18f, larger pixel arrays 1810 may be accommodated or designed by extrapolating the above described process through additional iterations. FIG. 18b illustrates a superimposed silicon substrate stack. In the figure, a first substrate 1852 consisting of a pixel array is shown overlaid on top of a support substrate 1854 that comprises support circuits. The area available for locating support circuits for a first pixel column 1881 is outlined in dashed lines and labeled for the sake of simplicity and discussion. It will be appreciated that the actual area of the circuit column is not represented by the dashed lines, but may be greater than, less than or the same as the area of the pixel column. As discussed above, the support circuit area directly correlates to the area of a pixel column to which they correspond. Each pixel column may be one pixel wide and sixty-four pixels long and may have one read bus that runs from the top to the bottom of the pixel column. In FIG. 18b the area available for support circuit placement may be equal to one pixel unit wide by sixty-four pixel units long, which is shown as the heavier vertical lines in the figure. Therefore, the interconnect 1824 between the substrates in FIG. 18b must fall somewhere within the sixty-four pixel unit area in order to read that column, since the pixel column read bus and the column circuit read bus are superimposed along the path of the sixty-four pixels, such that the interconnect 1824 may be placed anywhere along those sixty-four pixels to connect the read buses.

Moreover, because the interconnect can happen only where the pixel column read bus and the support circuit read bus superimpose, the interconnect range in order to read the corresponding pixel column is 1 pixel wide and 64 pixels long (for this example), which is the intercept between the pixel column and the support circuit to be connected.

It should be noted that the exemplary aspect ratio of the support circuit area in FIG. 18b is illustrated as 1/64. There are many options to locate or place the interconnect 1824 within that area and the ultimate location may then be chosen by the designer so as to allow the desired spacing from interconnect to interconnect. For example, as illustrated best in FIGS. 18b-18f, it will be appreciated that in an embodiment in which the interconnects or bumps 1824 are in a staggered configuration, there may be one interconnect or bump 1824 per group of pixels 1826.

Additionally, it should be noted that various read bus architectures may be utilized depending on the desired application. As discussed above, larger dedicated support circuits may be employed to process the data read through each interconnect 1824. The staggering of the position of each interconnect/bump 1824 may also provide even greater space for support circuits relative to each area or group of pixels within the pixel array 1810.

It should also be noted that many optimum staggering configurations have been found for the same base sensor with different support circuit aspect ratios as illustrated in FIGS. 18b to 18f. An optimum configuration can be found by varying the position of the interconnect within the range of the intercept between the pixel column and the support circuit and the pattern of the allocation of the support circuit to each pixel column. It should also be noted that all interconnects illustrated in FIGS. 18b to 18f are more than 7 pixels in distance away from each other.

Figure 18C:
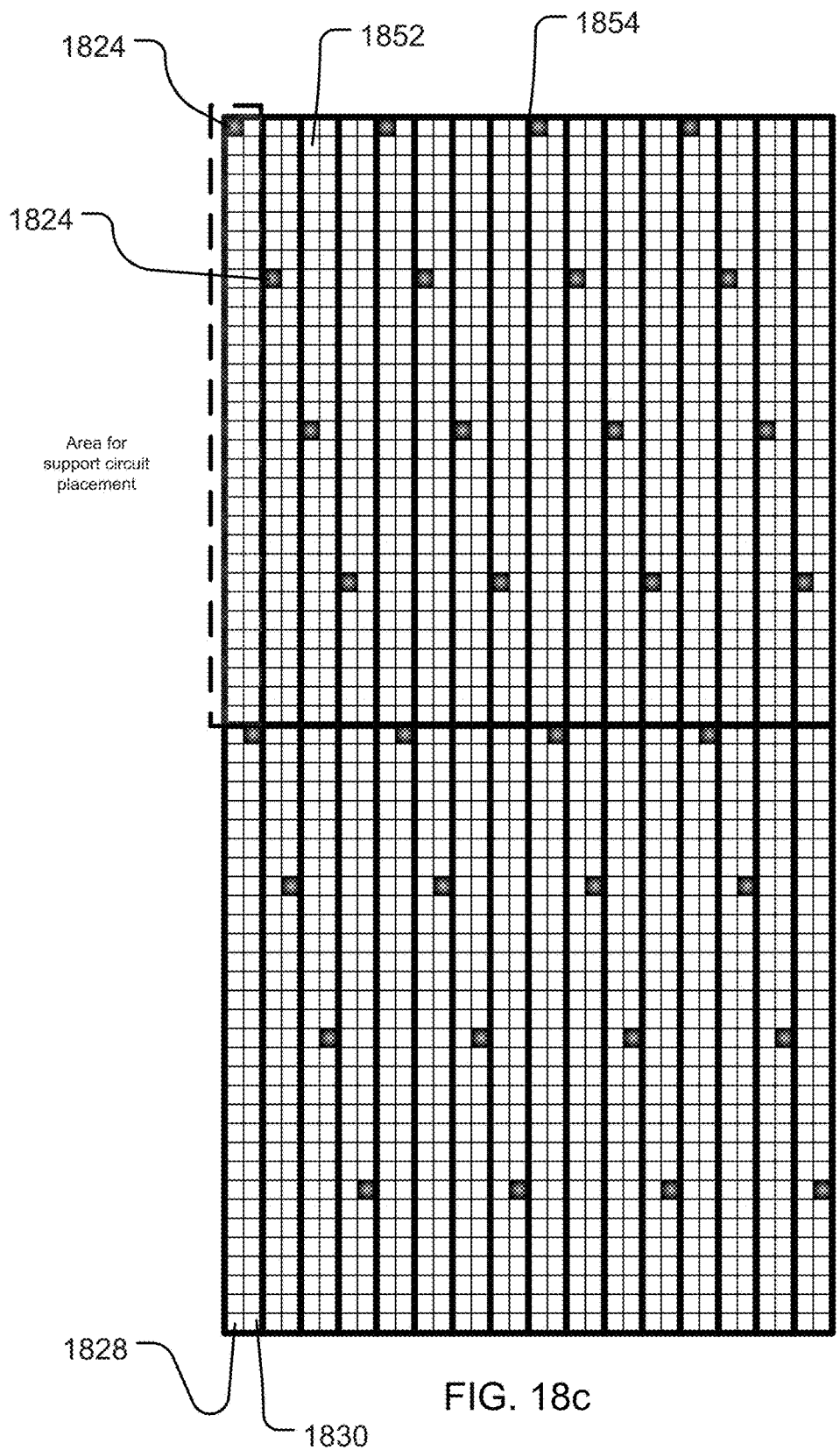

In FIG. 18c the area available for support circuit placement may be equal to two pixel units wide by thirty-two pixel units long, which is shown as the heavier vertical lines in the figure. Therefore, the interconnect between the substrates 1852 and 1854 must fall somewhere in the sixty-four pixel unit area in order to read that column. It should be noted that the aspect ratio of the support circuit area in this example is 2/32. Each pixel column is or may be one pixel wide and sixty-four pixels long and may have one read bus that runs from the top to the bottom of the pixel column. The choice of where to place the interconnect has many options within that area and could be chosen so as to allow the desired spacing from interconnect to interconnect. Moreover, because the interconnect can be located only where the pixel column read bus and the support circuit read bus superimpose, in order to read the corresponding pixel column the interconnect range may be one pixel wide and thirty-two pixels long (for this example), which is the intercept between the pixel column and the support circuit to be connected.

Figure 18D:
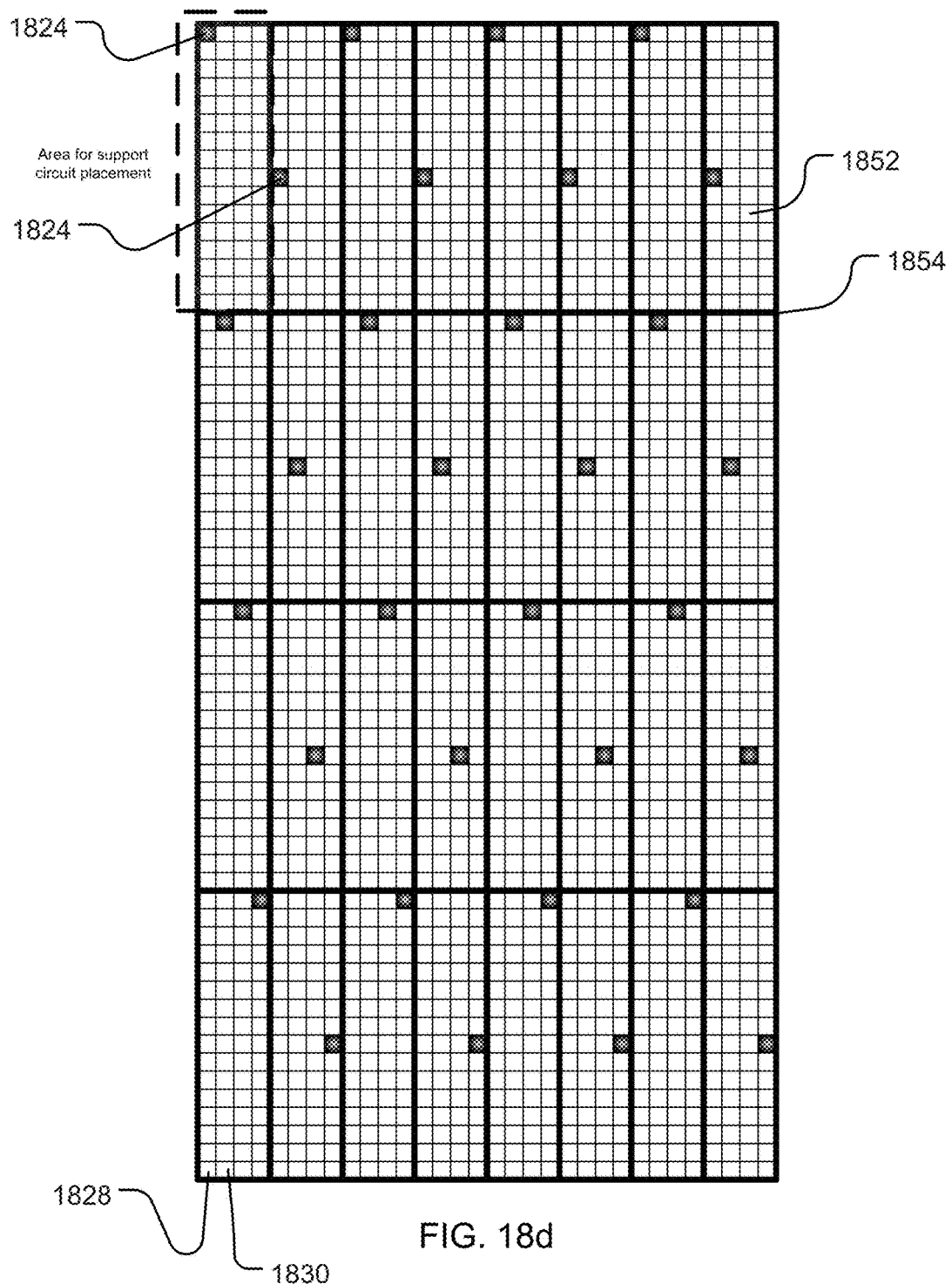

In FIG. 18d the area available for support circuit placement may be equal to four pixel units wide by sixteen pixel units long, which is shown as the heavier vertical lines in the figure. Therefore, the interconnect between the substrates must fall somewhere in the sixty-four pixel unit area in order to read the corresponding pixel column. It should be noted that the aspect ratio of the support circuit area in this example is 4/16. Each pixel column is or may be one pixel wide and sixty-four pixels long and may have one read bus that runs from the top to the bottom of the pixel column. The choice of where to place the interconnect has many options within that area and could be chosen so as to allow the desired spacing from interconnect to interconnect.

Moreover, because the interconnect can be located only where the pixel column read bus and the support circuit read bus superimpose, in order to read the corresponding pixel column the interconnect range may be one pixel wide and sixteen pixels long (for this example), which is the intercept between the pixel column and the support circuit to be connected.

Figure 18E:
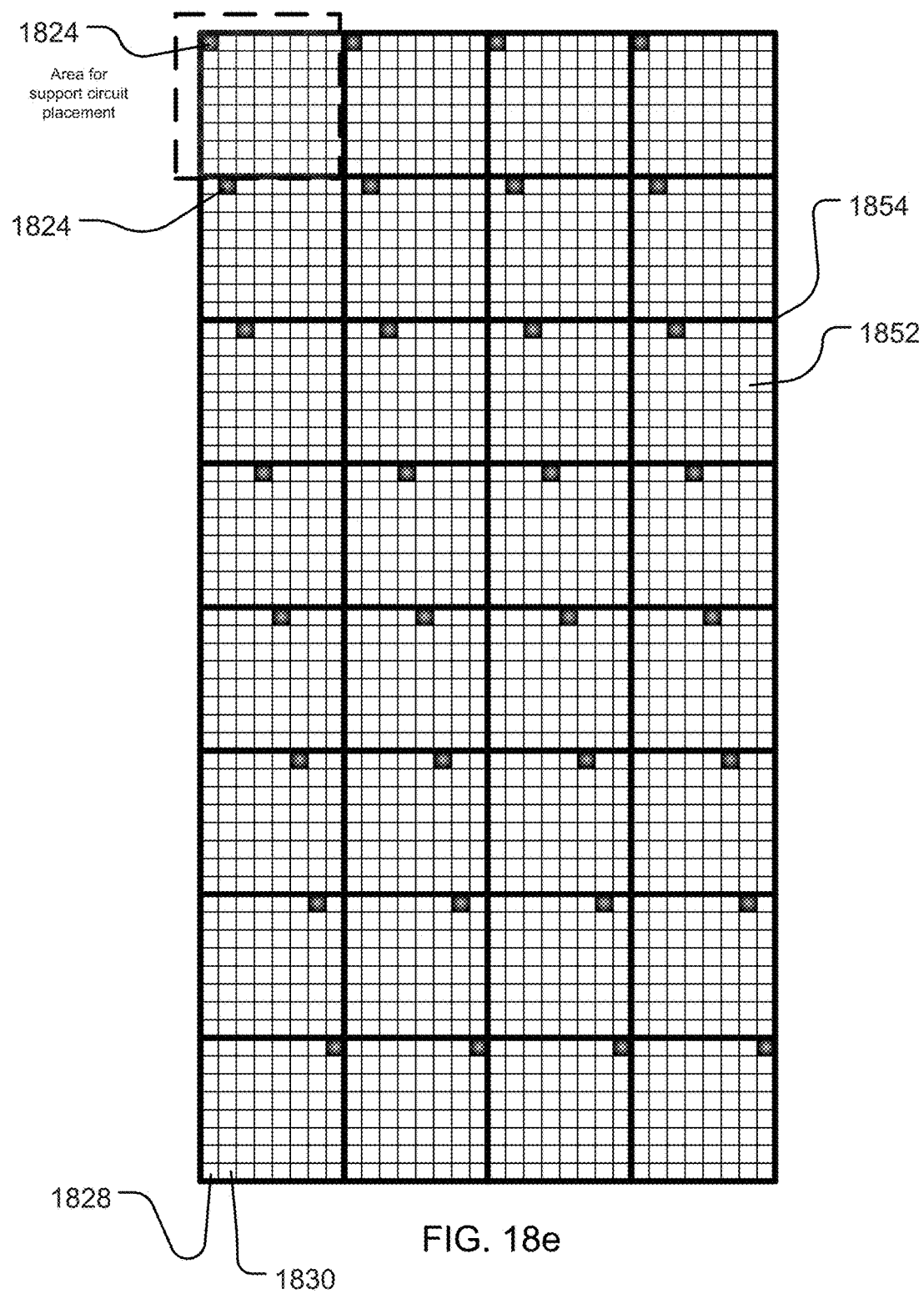

In FIG. 18e the area available for support circuit placement may be equal to eight pixel units wide by eight pixel units long, which is shown as the heavier vertical lines in the figure. Therefore, the interconnect 1824 between the substrates 1852 and 1854 must fall somewhere in the sixty-four pixel unit area in order to read the corresponding pixel column. It should be noted that the aspect ratio of the support circuit area in this example is 8/8. Each pixel column is or may be one pixel wide and sixty-four pixels long and may have one read bus that runs from the top to the bottom of the pixel column. The choice of where to place the interconnect has many options within that area and could be chosen so as to allow the desired spacing from interconnect to interconnect.

Moreover, because the interconnect can be located only where the pixel column read bus and the support circuit read bus superimpose, in order to read the corresponding pixel column the interconnect range may be one pixel wide and eight pixels long (for this example), which is the intercept between the pixel column and the support circuit to be connected.

Figure 18F:
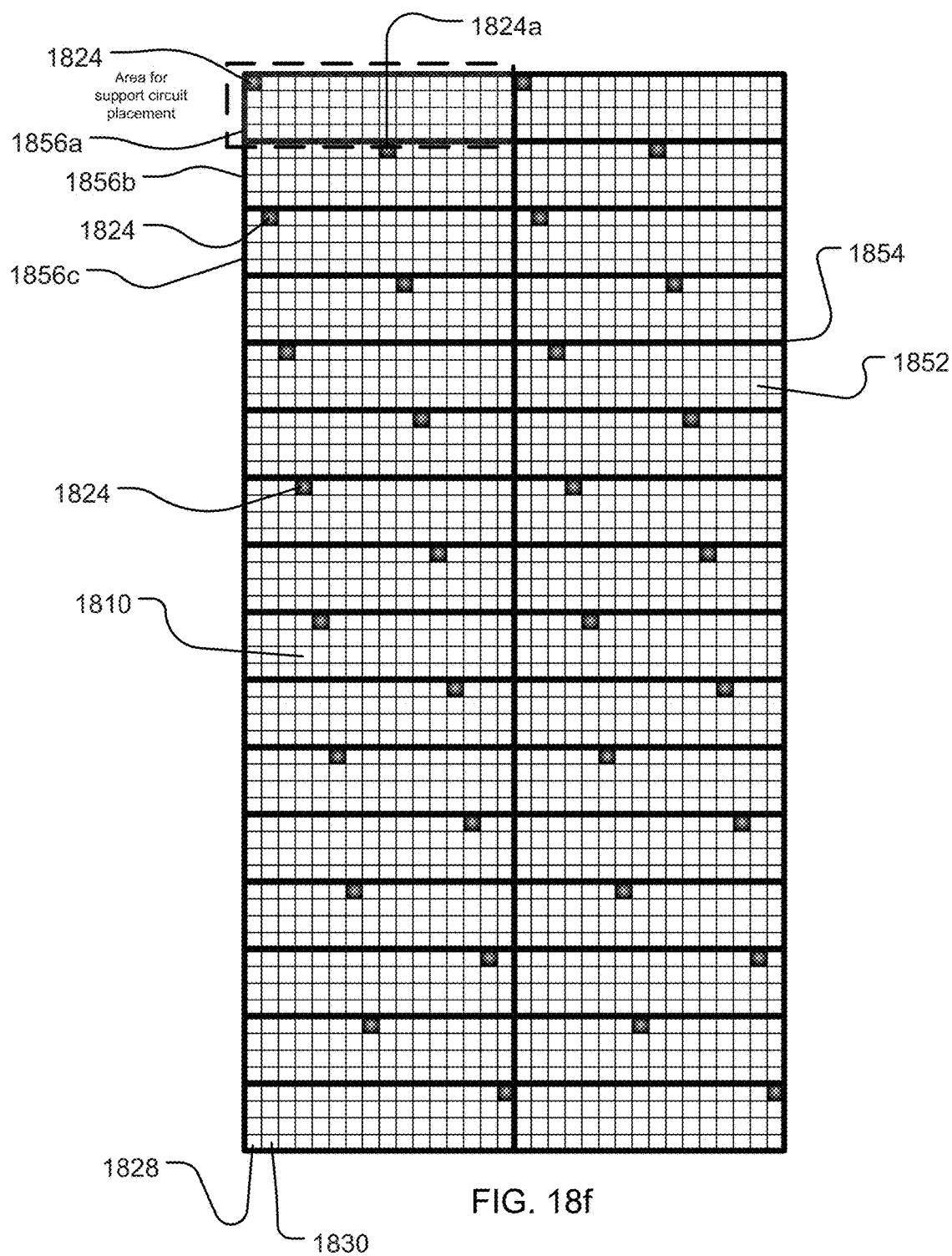

In FIG. 18f the area available for support circuit placement may be equal to sixteen pixel units wide by four pixel units long, which is shown as the heavier vertical lines in the figure. Therefore, the interconnect between the substrates must fall somewhere in the sixty-four pixel unit area in order to read the corresponding pixel column. It should be noted that the aspect ratio of the support circuit area in this example is 16/4, this example shows the flexibility that these methods and apparatuses disclosed herein can provide. Each pixel column is or may be one pixel wide and sixty-four pixels long and may have one read bus that runs from the top to the bottom of the pixel column. The choice of where to place the interconnect has many options within that area and could be chosen so as to allow the desired spacing from interconnect to interconnect.

Moreover, because the interconnect can be located only where the pixel column read bus and the support circuit read bus superimpose, in order to read the corresponding pixel column the interconnect range may be one pixel wide and four pixels long (for this example), which is the intercept between the pixel column and the support circuit to be connected.

It should also be noted that the pattern of the association of the support circuit to the pixel column may be different than that of FIGS. 18b through 18f and such association may ultimately provide the optimal distance of the interconnects away from each other. For example, the interconnects may be optimally placed at least two pixel widths apart, four pixel widths apart, eight pixel widths apart, or more from each other. A designer may optimally determine the distance that the interconnects may be placed apart from one another based on two degrees of freedom: (1) the number of pixels per column, and (2) the circuit aspect ratio and location. In the examples shown in FIGS. 18b-18f, the interconnects 1824 may be located about eight pixels away from each other. However, it will be understood that other designs may be implemented without departing from the spirit or scope of the disclosure.

For example, as illustrated in FIG. 18b, each of the interconnects 1824 may be located eight pixels in length and one pixel in width away from each other. Because the circuit columns each have an aspect ratio of one pixel in width and sixty-four pixels in length, the interconnects 1824 may then be located eight pixels away from each other in adjacent columns as illustrated in FIG. 18b, until the bottom of the circuit 1800 is reached, in which case the interconnects 1824 are then moved to the top of the next column and continue for the entire width of the pixel array 1810. Conversely, in FIG. 18f, the interconnects 1824 are still located eight pixels in length and one pixel in width away from each other. However, in this example, the circuit column aspect ratio is now four pixels in length and sixteen pixels in width. Thus, for the interconnects 1824 to be at least eight pixels away from each other, one circuit column 1856b must be skipped since the aspect ratio is only four pixels in length, such that the interconnects 1824 maintain optimal spacing. Thus, for example, placing an interconnect 1824 in the upper left corner of the pixel array 1810 in FIG. 18f (on the first pixel of the first column 1828) and then moving to the next pixel column 1830 and counting down eight pixels in length, the next interconnect 1824 may then be placed in the third circuit column 1856c, skipping the second circuit column 1856b altogether. This pattern may be used throughout the pixel array. The second, skipped circuit column 1856b is then connected to the pixel array by an interconnect 1824a that is placed in the ninth pixel column and the pattern is repeated for all skipped circuit columns. Thus, as illustrated, optimal interconnect spacing may be achieved and various circuit designs may be accommodated without departing from the scope of the disclosure.

Referring back to FIG. 7, in addition to the first image sensor 710 and the second image sensor 711, which are in electrical communication with a substrate 715 or a plurality of substrates, there is illustrated an embodiment of an imaging sensor having a plurality of pixel arrays that may be configured with staggered interconnects as discussed herein above. Such a configuration may be desirable for three dimensional image capture, wherein the two pixel arrays may be off set during use. In another embodiment, a first pixel array and a second pixel array may be dedicated to receiving a predetermined range of wave lengths of electromagnetic radiation, wherein the first pixel array is dedicated to a different range of wavelength electromagnetic radiation than the second pixel array.

Figure 19:
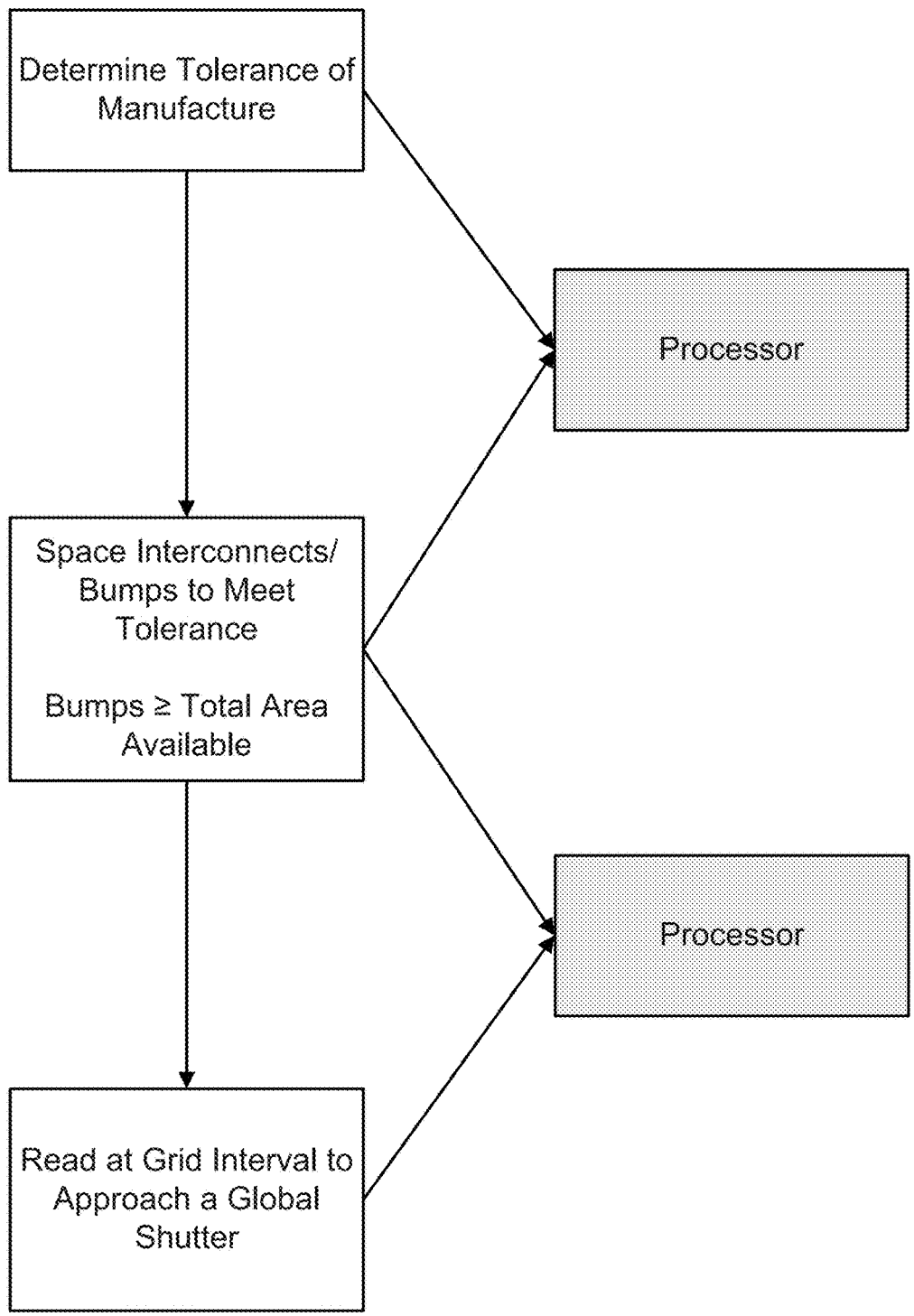
FIG. 19 illustrates a method of spacing interconnects/bumps in accordance with the principles and teachings of the disclosure.

FIG. 19 illustrates a design and testing methodology related to optimizing a pixel array on a first substrate. A step may be to decide on the available tolerancing differences for manufactures for an imaging sensor. A design may then be processed and bump pitch may be determined for a certain criteria. A simulated test sensor may then be tested and read and redesigned if desired.

Figure 20:
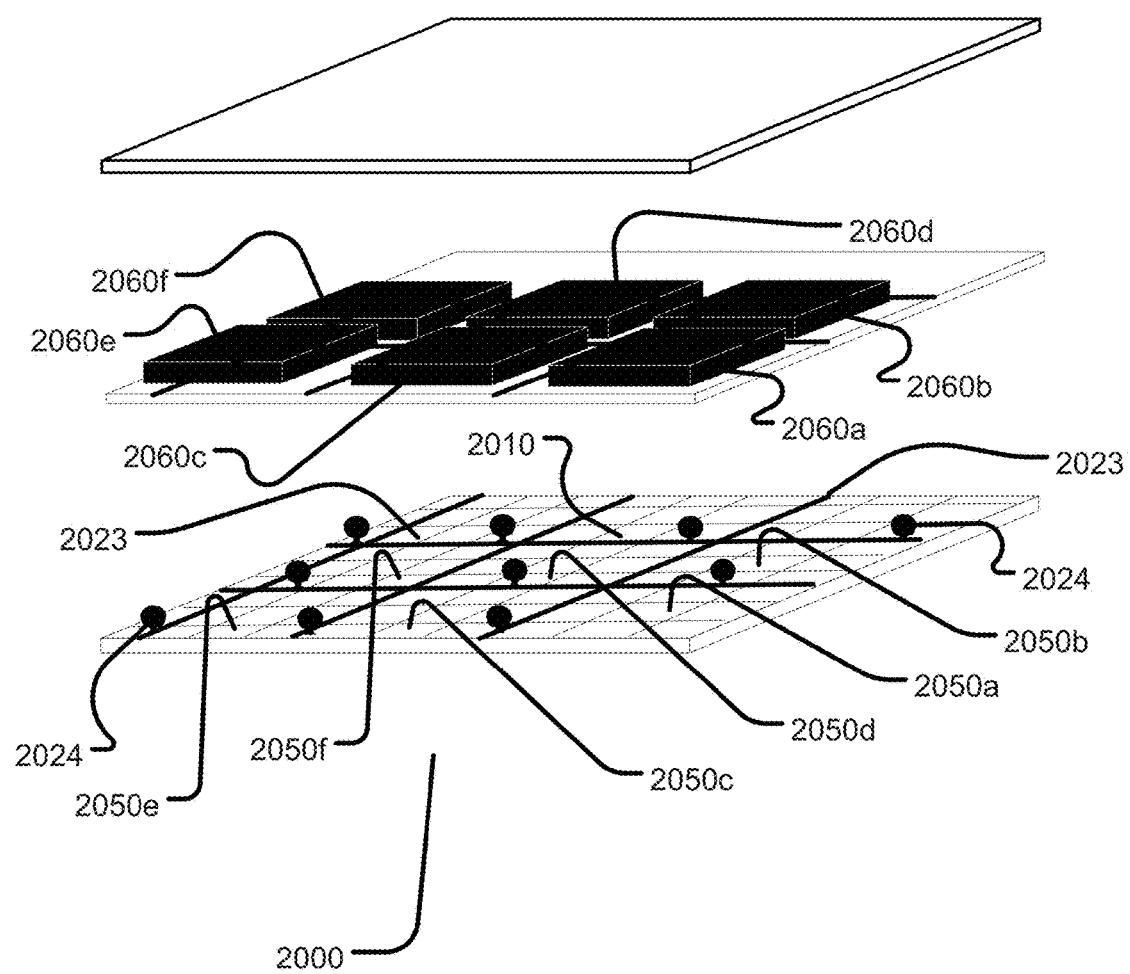
FIG. 20 illustrates an embodiment wherein pixel area dedicated support circuits may be used such that each pixel area may have at least a support circuit dedicated to processing only the data produced by pixels within the pixel area to which it is dedicated.

FIG. 20 illustrates an embodiment having at least one dedicated support circuit for a given pixel area. A plurality of dedicated support circuits 2060a-2060f may be used in an imaging device 2000 and may be stacked with respect to the pixel array 2010 according to the principles of the disclosure. The pixel array 2010 may comprise a plurality of pixel areas 2050. Each of the plurality of pixel areas, such as 2050a-2050f, may comprise at least one support circuit 2060 dedicated to processing only the data produced by the plurality of pixels 2026 within a given predetermined or defined pixel area 2050 to which the dedicated circuit 2060 is devoted. For example, each pixel area 2050 may have a dedicated analog to digital conversion circuit dedicated to converting the analog data read from the associated pixels 2026 from within the associated pixel area 2050. This close and direct association of dedicated circuits can be used to simplify the digital signal processing within the image sensor thereby greatly simplifying timing and serializing processes within the image sensor. Such a feature can be used to control heat production and energy consumption within the image sensor.

Figure 21:
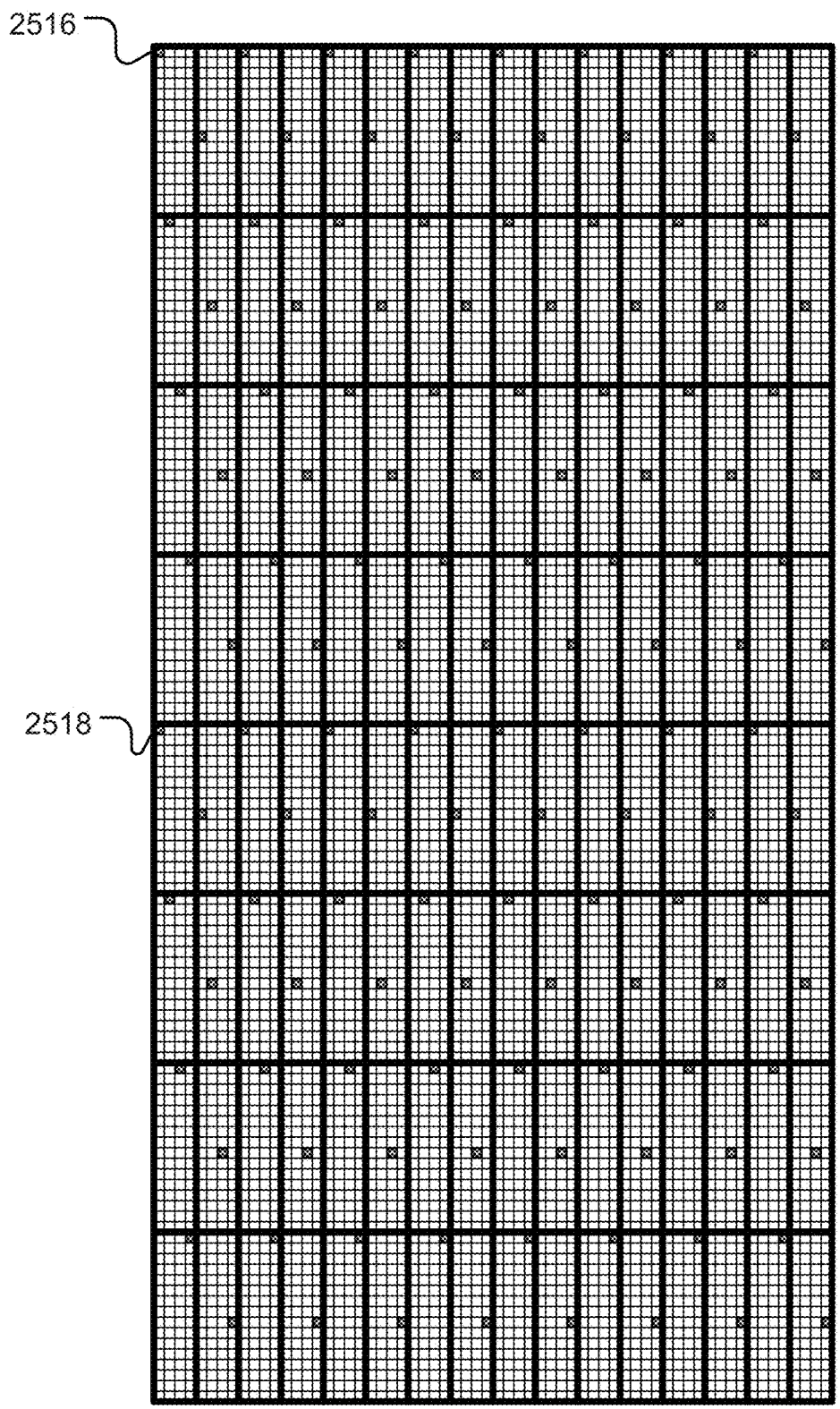
FIG. 21 illustrates an embodiment of a schematically large image sensor showing the scalability of the principles and teaching of the disclosure.

In FIG. 21 illustrates a schematically large image sensor showing the scalability of the principles and teaching of the disclosure. Each pixel column is or may be one pixel wide and one-hundred and twenty-eight pixels long. Note that this has been chosen as an example for representing the teaching of the disclosure, but it should be noted that any number of pixels for the column length is possible and may be used without departing from the scope of the disclosure. It should be further noted that the number of pixels for the column length may be an even or odd number and does not have to be a power of 2. As can be seen in the figure, the area available for support circuit placement may be equal to four pixel units wide by sixteen pixel units long, which is shown as the heavier vertical lines in the figure. Therefore, the interconnect between the substrates must fall somewhere in the sixty-four pixel unit area. Moreover, because the interconnect can be located only where the pixel column read bus and the support circuit read bus superimpose, in order to read the corresponding pixel column the interconnect range may be one pixel wide and sixteen pixels long (for this example), which is the intercept between the pixel column and the support circuit to be connected. It should be noted that the aspect ratio of the support circuit area in this example is 4/16. The choice of where to place the interconnect has many options within that area and could be chosen so as to allow the desired spacing from interconnect to interconnect. As the figure illustrates, by repeating the methods of this disclosure even the latest imaging sensor technology can be used with these methods. It should also be noted that there may be a plurality of interconnects (2516 and 2518) for any give pixel column so as to allow for more flexibility (pixel column parallel processing e.g.) for large array configurations.

Figure 22:
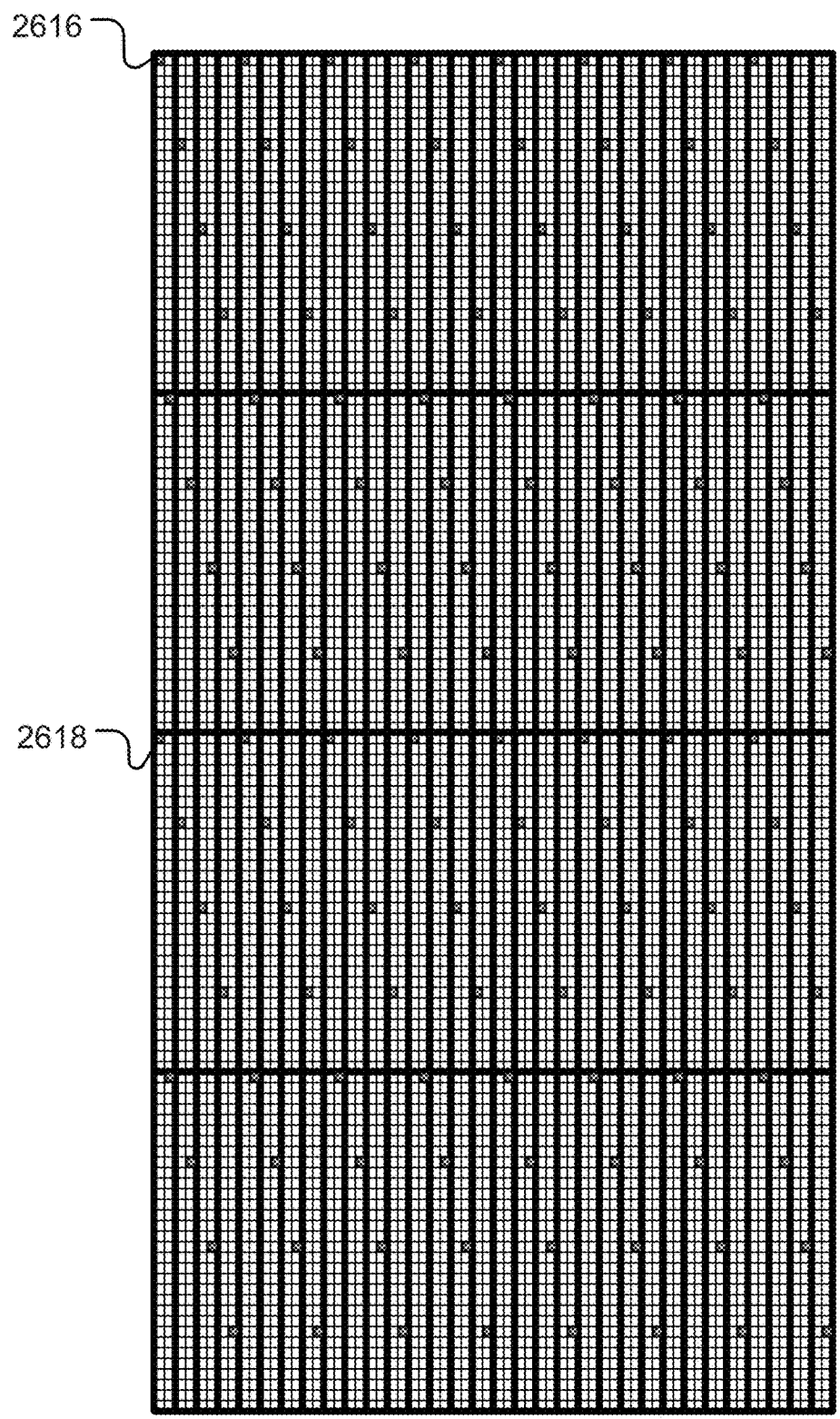
FIG. 22 illustrates an embodiment of a schematically large image sensor showing the scalability of the principles and teaching of the disclosure.

In FIG. 22 illustrates a schematically large image sensor showing the scalability of the principles and teaching of the disclosure. Each pixel column is or may be one pixel wide and one-hundred and twenty-eight pixels long. Note that this has been chosen as an example for representing the teaching of the disclosure, but it should be noted that any number of pixels for the column length is possible and may be used without departing from the scope of the disclosure. It should be further noted that the number of pixels for the column length may be an even or odd number and does not have to be a power of 2. As can be seen in the figure, the area available for support circuit placement may be equal to two pixel units wide by thirty-two pixel units long, which is shown as the heavier vertical lines in the figure. Therefore, the interconnect between the substrates must fall somewhere in the sixty-four pixel unit area. Moreover, because the interconnect can be located only where the pixel column read bus and the support circuit read bus superimpose, in order to read the corresponding pixel column the interconnect range may be one pixel wide and sixteen pixels long (for this example), which is the intercept between the pixel column and the support circuit to be connected. It should be noted that the aspect ratio of the support circuit area is 2/32. The choice of where to place the interconnect has many options within that area and could be chosen so as to allow the desired spacing from interconnect to interconnect. As the figure illustrates, by repeating the methods of this disclosure even the latest imaging sensor technology can be used with these methods. It should also be noted that there may be a plurality of interconnects (2616 and 2618) for any give pixel column so as to allow for more flexibility (pixel column parallel processing e.g.) for large array configurations. It should be noted that FIGS. 21 and 22 represent the same pixel array with the only difference between the two figures is the aspect ratio of the support circuitry has changed (i.e., 4/16 aspect ratio in FIG. 21 and 2/32 aspect ratio in FIG. 22).

It will be appreciated that the structures and apparatuses disclosed herein are merely exemplary for optimizing an imaging sensor, and it should be appreciated that any structure, apparatus or system for optimizing a pixel array on an image sensor using a three dimensional stacking technology and staggering the interconnects between substrates in the stack, which performs functions the same as, or equivalent to, those disclosed herein are intended to fall within the scope of this disclosure, including those structures, apparatuses or systems for imaging, which are presently known, or which may become available in the future. Anything which functions the same as, or equivalently to, a means for optimizing a pixel array on an image sensor using a three dimensional stacking technology and staggering the interconnects between substrates in the stack falls within the scope of this disclosure.

Those having ordinary skill in the relevant art will appreciate the advantages provide by the features of the disclosure. For example, it is a potential feature of the disclosure to provide an optimized pixel array on an imaging sensor, which is simple in design and manufacture. Another potential feature of the disclosure is to provide such an imaging sensor with larger pixels relative to overall size. Another potential feature is to provide an optimized pixel array on an image sensor using a three dimensional stacking technology and staggering the interconnects between substrates within the stack.

In the foregoing Detailed Description, various features of the disclosure are either grouped together in a single embodiment for the purpose of streamlining the disclosure or are discussed in different embodiments. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment and various inventive features disclosed in separate embodiments may be combined to form its own embodiment as claimed more fully below. Thus, the following claims are hereby incorporated into this Detailed Description by this reference, with each claim standing on its own as a separate embodiment of the disclosure.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements. Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. An imaging sensor comprising:
a plurality of substrates comprising a first substrate and at least one second, subsequent supporting substrate;
a pixel array;
a plurality of interconnects; and
a plurality of supporting circuits;
wherein the first substrate of the plurality of substrates comprises a plurality of pixel read buses and the pixel array, wherein the pixel array comprises a plurality of pixel groups, and wherein there is one pixel read bus per pixel group;
wherein the at least one second, subsequent supporting substrate comprises a plurality of circuit buses and the plurality of supporting circuits, including a plurality of readout supporting circuits, with one circuit bus per readout supporting circuit;
wherein said plurality of supporting circuits are electrically connected to, and in electrical communication with, said pixel array via the plurality of interconnects disposed between said first substrate and said at least one second, subsequent supporting substrate;
wherein each of the plurality of interconnects reads out a pixel group to one of the circuit buses;
wherein said at least one second, subsequent supporting substrate is disposed behind said first substrate relative to an object to be imaged;
wherein said plurality of interconnects are spaced relative to one another at a distance that is greater than a pixel pitch of said pixel array.

2. The imaging sensor of claim 1, wherein said imaging sensor is backside illuminated.

3. The imaging sensor of claim 1, wherein the plurality of substrates further comprise a plurality of second, subsequent supporting substrates.

4. The imaging sensor of claim 3, wherein said first substrate and said plurality of second, subsequent supporting substrates are stacked in alignment so that a plurality of communication columns are formed in a multi-layer stack.

5. The imaging sensor of claim 1, wherein said pixel array covers a substantial majority of a surface of said first substrate.

6. The imaging sensor of claim 1, wherein one of said supporting circuits is an analog to digital converter.

7. The imaging sensor of claim 1, wherein one of said supporting circuits is an amplifier circuit.

8. The imaging sensor of claim 1, wherein said at least one second, subsequent supporting substrate is aligned in the Z-dimension with said first substrate in a stacked configuration.

9. The imaging sensor of claim 1, wherein said second, subsequent supporting substrate is disposed behind said first substrate and displaced laterally therefrom.

10. The imaging sensor of claim 1, wherein each of the plurality of interconnects is a bump and comprises a bump to bump distance that is greater than two pixels in width.

11. The imaging sensor of claim 10, wherein the bump to bump distance is greater than four pixels in width.

12. The imaging sensor of claim 10, wherein the bump to bump distance is greater than eight pixels in width.

13. The imaging sensor of claim 10, wherein the bump pitch is greater than $\sqrt{(N*PixelPitch_x)^2+(M*PixelPitch_y)^2}$.

14. The imaging sensor of claim 1, wherein the pixel array is comprised of a plurality of pixel columns, wherein each pixel column comprises a plurality of pixels; wherein each of the plurality of pixel columns within the pixel array is read to a bus, starting from a first column that is read from a common origin, wherein a second column is read from a first row that is different from the pixel column that was previously read with respect to the second column and different from the pixel column that is read subsequent with respect to the second column.

15. The imaging sensor of claim 14, wherein said first row is spaced at least two row positions away from the row position of the previously read pixel column and the subsequently read pixel column.

16. The imaging sensor of claim 1, wherein the readout supporting circuits and the corresponding pixel groups have different aspect ratios.

17. The imaging sensor of claim 1, wherein each of the pixel groups is a column of pixels.

18. The imaging sensor of claim 17, wherein a column of pixels is 1 pixel wide from a top row to a bottom row; or wherein a column of pixels is 2 pixels wide from a top row to a bottom row; or wherein a column of pixels is 3 pixels wide from a top row to a bottom row; or wherein a column of pixels is 4 pixels wide from a top row to a bottom row.

19. The imaging sensor of claim 17, wherein a column of pixels is less than the entire column from a top row to a bottom row that is 1 pixel wide; or wherein a column of pixels is less than the entire column from a top row to a bottom row that is 2 pixels wide; or wherein a column of pixels is less than the entire column from a top row to a bottom row that is 3 pixels wide; or wherein a column of pixels is less than the entire column from a top row to a bottom row that is 4 pixels wide.

20. The imaging sensor of claim 1, wherein one pixel read bus reads out one pixel group to one circuit bus of the readout supporting circuit, wherein the readout supporting circuit has an area that is substantially the same as an area of the pixel group.

* * * * *